United States Patent
Cesaroni et al.

(10) Patent No.: US 12,009,079 B2
(45) Date of Patent: Jun. 11, 2024

(54) TYPE I INTERFERON SIGNATURES AND METHODS OF USE

(71) Applicant: Janssen Biotech, Inc., Horsham, PA (US)

(72) Inventors: Matteo Cesaroni, Philadelphia, PA (US); Marc Chevrier, Collegeville, PA (US); Jarrat Jordan, Norristown, PA (US); Jessica Schreiter, Macungie, PA (US)

(73) Assignee: Janssen Biotech, Inc., Horsham, PA (US)

( * ) Notice: Subject to any disclaimer, the term of this patent is extended or adjusted under 35 U.S.C. 154(b) by 1196 days.

(21) Appl. No.: 16/663,527

(22) Filed: Oct. 25, 2019

(65) Prior Publication Data

US 2020/0131241 A1     Apr. 30, 2020

Related U.S. Application Data

(60) Provisional application No. 62/751,019, filed on Oct. 26, 2018.

(51) Int. Cl.
| | |
|---|---|
| *C07K 14/56* | (2006.01) |
| *C12Q 1/6809* | (2018.01) |
| *G16H 20/10* | (2018.01) |
| *G16H 50/30* | (2018.01) |

(52) U.S. Cl.
CPC .............. *G16H 20/10* (2018.01); *C07K 14/56* (2013.01); *C12Q 1/6809* (2013.01); *G16H 50/30* (2018.01); *C07K 2317/565* (2013.01); *C12Q 2539/00* (2013.01); *C12Q 2545/114* (2013.01)

(58) Field of Classification Search
CPC .............. C07K 14/56; C07K 2317/565; C07K 2317/76; C07K 2317/94; C07K 16/249; C12Q 1/6809; C12Q 2539/00; C12Q 2545/114; C12Q 2600/106; C12Q 1/6883; A61K 2039/505; A61K 2039/54; A61K 2039/545; A61P 37/06
See application file for complete search history.

(56) References Cited

U.S. PATENT DOCUMENTS

| | | | | |
|---|---|---|---|---|
| 8,551,476 | B2 * | 10/2013 | Mi ........................... | A61P 25/14 424/134.1 |
| 10,640,563 | B2 * | 5/2020 | Benatuil ................ | A61P 43/00 |
| 10,689,441 | B2 * | 6/2020 | Monnet .................. | A61K 45/06 |
| 2010/0143372 | A1 | 6/2010 | Yao et al. | |
| 2013/0261018 | A1 * | 10/2013 | Pfeffer ................. | C12Q 1/6886 435/6.12 |
| 2014/0056889 | A1 * | 2/2014 | Morimoto ............... | A61P 19/02 435/6.12 |
| 2016/0312285 | A1 * | 10/2016 | Nick ...................... | G16B 25/20 |

FOREIGN PATENT DOCUMENTS

| | | | |
|---|---|---|---|
| WO | WO 2008/070137 | A2 | 6/2008 |
| WO | WO 2008/137838 | A2 | 11/2008 |
| WO | WO 2010/120759 | A1 | 10/2010 |
| WO | WO 2012/054284 | A2 | 4/2012 |
| WO | WO 2012/149228 | A1 | 11/2012 |
| WO | WO 2012/162367 | A1 | 11/2012 |
| WO | WO 2013/101771 | A2 | 7/2013 |
| WO | WO 2013/188494 | A1 | 12/2013 |
| WO | WO 2015/200165 | A1 | 12/2015 |
| WO | WO 2020/202106 | A1 | 10/2020 |

OTHER PUBLICATIONS

Livak, KJ and Schmittgen, TD. Analysis of Relative Gene Expression Data Using Real-Time Quantitative PCR and the 22DDCT Method. Methods 25: 402-408. (Year: 2001).*
Baechler et al., "Interferon-inducible gene expression signature in peripheral blood cells of patients with severe lupus," Proceedings of the National Academy of Science USA, 100:2610-2615 (2003).
Baldi et al., "Assessing the accuracy of prediction algorithms for classification: an overview," Bioinformatics Review, 16:412-424 (2000).
Bennett et al. Interferon and Granulopoieses Signatures in Systemic Lupus Erythematosus Blood, Journal of Experimental Medicine, 197:711-723 (2003).
Dall'era et al., "Type I Interferon correlates with serological and clinical manifestations of SLE," Annals of Rheumatic Disease, 64:1692-1697 (2005).
Furie et al., Anifrolumab, an Anti-Interferon-α Receptor Monoclonal Antibody, in Moderate-to-Severe Systemic Lupus Erythematosus, Arthritis & Rheumatology 69:376-386 (2017).
Karageorgas et al., "Activation of Tyype I Interferon Pathway in Systemic Lupus Erythematosus: Association with Distinct Clinical Phenotypes," Journal of Biomedicine and Biotechnolgy, 273907, 13 pages (2011).
Lu et al., J Autoimmun 74:182-93, 2016.
Medrano et al.,. Immunomodulatory and antitumor effects of type I interferons and their applicaion in cancer therapy, Oncotarget 8:71249-71284 (2017).
Muskardin, et al., "Type I Interferon in rheumatic diseases," Nature Reviews Rheumatology 14:214-228, (2018).
Niewold et al., "High serum IFN-α activity is a heritable risk factor for systemic lupus erythematosus," Genes Immun 8: 492-502 (2007).
Petri et al., "Derivation and Validation of the Systemic Lupus International Collaborating Clincis Classification Criteria for Systemic Lupus Erythematosus," Arthritis & Rheumatism, 64: 2677-2686 (2012).

(Continued)

*Primary Examiner* — Soren Harward
*Assistant Examiner* — Robert James Kallal
(74) *Attorney, Agent, or Firm* — Goodwin Procter LLP

(57) ABSTRACT

Type I interferon (IFN-I) signatures are useful in methods of diagnosing whether a subject (or patient) with IFN-I mediated disease will be responsive to treatment with an IFN-I inhibitor and treating or refraining from treating the subjects.

20 Claims, 10 Drawing Sheets

Specification includes a Sequence Listing.

(56) References Cited

OTHER PUBLICATIONS

Richardson et al., "Development of a Quantitative PCR Method to Determine Interferon Signature Metric Status in SLE Patients: Districitons and Clinical & Serological Assosication in Two Lupus Clinical Trials," ACR/ARHP 2012 Annual Meeting Abstract 620 (2012).

Tcherepanova et al., Annals of the Rheumatic Diseases 71(Suppl3) (2012).

Van Vollenhoven et al., "Efficacy and safety of ustekinumab, an IL-12 and IL-23 inhibitor, in patients with active systemic lupus erythematosus: results of a multicentre, double-blind, phase 2, randomised, controlled study," Lancet 392: 1330-1339 (2018).

Woo et al., "Alpha-interferonn treatment in hepatitis B," Annals of Translational Medicine 5:159 (2017).

Yao et al.,. "Development of Potential Pharmacodynamic and Diagnostic Markers for Anti-IFN-α Monoclonal Antibody Trials in Systemic Lupus Erythematosus," Human Genomics and Proteomics : HGP : 1-16 2009).

Zettl et al., Interferon β-1a and β-1b for patients with multiple sclerosis: updates to curent knowlgedge, Expert Review of Clinical Immunology 14:137-153 (2018).

Zhang et al., Genome Biol. 2015, 16:14.

EP Search Report for EP 19 87 4869 Date of completion Jun. 30, 2022.

PCT Written Opinion for PCT/IB19/59178 dated Feb. 19, 2020.

\* cited by examiner

TYPE I INTERFERON SIGNATURES AND METHODS OF USE

CROSS-REFERENCE TO RELATED APPLICATIONS

This application claims the benefit of the U.S. Provisional Application Ser. No. 62/751,019, filed 26 Oct. 2018, the entire contents of which is incorporated herein by reference.

SEQUENCE LISTING

The instant application contains a Sequence Listing which has been submitted electronically in ASCII format and is hereby incorporated by reference in its entirety. Said ASCII copy, created on Oct. 17, 2019, is named JBI6021USNP1ST25.txt and is 63 kilobytes in size.

FIELD

The disclosure is directed to Type I interferon signatures and methods of using them.

BACKGROUND

Type I interferon (IFN-I) may exhibit protective or deleterious effects depending on the disease setting. For example, recombinant IFN-I has been utilized as a treatment for a variety of cancers (Medrano et al. *Oncotarget* 8:71249-84, 2017), chronic hepatitis (Woo et al., *Annals of Translational Medicine* 5:159, 2017), and multiple sclerosis (Zettl et al., *Expert Review of Clinical Immunology* 14:137-53, 2018), while many autoimmune disorders may benefit from blockade of this pathway (Muskardin and Niewold, *Nature Reviews Rheumatology* 14:214-28, 2018). Evaluation of IFN-I inducible transcripts (e.g., IFN-I signature) can facilitate assessment of disease status and/or efficacy of treatment in established disease or preventive interventions within early onset diseases in which IFN-I plays a role. Therefore, there is a need to develop sensitive means to detect IFN-I signatures.

SUMMARY OF THE DISCLOSURE

The disclosure provides a method of diagnosing and treating a subject having a type I interferon (IFN-I) mediated disease that is responsive to treatment with an IFN-I inhibitor, comprising:
  providing a biological sample from the subject;
  assaying gene expression of genes DHX58, EIF2AK2, HERC5, IFI44, IFI44L, IF16, IRF7, PARP9, PLSCR1 and SAMD9L in the biological sample;
  determining a combined expression value of the genes DHX58, EIF2AK2, HERC5, IFI44, IFI44L, IFI6, IRF7, PARP9, PLSCR1 and SAMD9L in the biological sample;
  diagnosing the subject with the IFN-I mediated disease that is responsive to treatment with the IFN-I inhibitor when the combined expression value is equal to or higher than a threshold value; and administering the IFN-I inhibitor to the subject diagnosed as responsive to treatment with the IFN-I inhibitor.

The disclosure also provides a method of treating a subject suspected to have or having a type I interferon (IFN-I) mediated disease with an IFN-I inhibitor, comprising
  determining that the subject has an elevated IFN-I signature by
  providing a biological sample from the subject;
  assaying gene expression of genes DHX58, EIF2AK2, HERC5, IFI44, IFI44L, IFI6, IRF7, PARP9, PLSCR1 and SAMD9L in the biological sample;
  determining a combined expression value of the genes DHX58, EIF2AK2, HERC5, IFI44, IFI44L, IFI6, IRF7, PARP9, PLSCR1 and SAMD9L in the biological sample;
  determining that the subject has the elevated IFN-I signature when the combined expression value is equal to or higher than a threshold value; and
  administering the IFN-I inhibitor to the subject determined to have the elevated IFN-I signature to treat the IFN-I mediated disease.

The disclosure also provides a method of detecting an elevated type I interferon (IFN-I) signature in a subject, comprising:
  providing a biological sample from the subject;
  assaying gene expression of genes DHX58, EIF2AK2, HERC5, IFI44, IFI44L, IFI6, IRF7, PARP9, PLSCR1 and SAMD9L in the biological sample;
  determining a combined expression value of the genes DHX58, EIF2AK2, HERC5, IFI44, IFI44L, IFI6, IRF7, PARP9, PLSCR1 and SAMD9L in the biological sample; and
  detecting the elevated IFN-I signature in the subject when the combined expression value is equal to or higher than a threshold value.

The disclosure also provides a method of detecting a baseline type I interferon (IFN-I) signature in a subject, comprising:
  providing a biological sample from the subject;
  assaying gene expression of genes DHX58, EIF2AK2, HERC5, IFI44, IFI44L, IF16, IRF7, PARP9, PLSCR1 and SAMD9L in the biological sample;
  determining a combined expression value of the genes DHX58, EIF2AK2, HERC5, IFI44, IFI44L, IFI6, IRF7, PARP9, PLSCR1 and SAMD9L in the biological sample; and
  detecting the baseline IFN-I signature in the subject when the combined expression value is less than a threshold value.

The disclosure also provides a method of diagnosing and treating a subject having a type I interferon (IFN-I) mediated disease, comprising:
  obtaining a biological sample from a subject suspected to have or having a type I interferon (IFN-I) mediated disease;
  assaying gene expression of genes DHX58, EIF2AK2, HERC5, IFI44, IFI44L, IFI6, IRF7, PARP9, PLSCR1 and SAMD9L in the biological sample;
  determining a combined expression value of the genes DHX58, EIF2AK2, HERC5, IFI44, IFI44L, IFI6, IRF7, PARP9, PLSCR1 and SAMD9L in the biological sample;
  diagnosing the subject with IFN-I mediated disease when the combined expression value is equal to or higher than a threshold value; and
  treating the subject suspected to have or having IFN-I mediated disease by administering a therapeutically effective amount of an IFN-I inhibitor to the subject.

The disclosure also provides an in vitro method for predicting and/or diagnosing that a subject has an IFN-I mediated disease, comprising:

obtaining a biological sample from the subject;
assaying gene expression of genes DHX58, EIF2AK2, HERC5, IFI44, IFI44L, IFI6, IRF7, PARP9, PLSCR1 and SAMD9L in the biological sample;
determining a combined expression value of the genes DHX58, EIF2AK2, HERC5, IFI44, IFI44L, IFI6, IRF7, PARP9, PLSCR1 and SAMD9L in the biological sample; and
predicting and/or diagnosing that the subject has the IFN-I mediated disease when the combined expression value is equal to or higher than a threshold value.

The disclosure also provides a method of diagnosing and treating a subject with type I interferon (IFN-I) mediated disease that is responsive to treatment with an IFN-I inhibitor, comprising:
providing a biological sample from the subject;
assaying gene expression of genes DHX58, EIF2AK2, HERC5, IFI44, IFI44L, IFI6, IRF7, PARP9, PLSCR1 and SAMD9L in the biological sample;
determining
a sum of normalized threshold cycle (CT) values (SUMΔCT) of genes DHX58, EIF2AK2, HERC5, IFI44, IFI44L, IFI6, IRF7, PARP9, PLSCR1 and SAMD9L;
a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{-ddCT}$)); or
a POISE score calculated according to a formula I:
POISE Score=70−|43.7251664−SUMlog2($2^{-ddCT}$)| (Formula I); or any combination thereof;
diagnosing the subject with IFN-I mediated disease that is responsive to treatment with the IFN-I inhibitor when SUMΔCT is equal to or higher than a threshold SUMΔCT value of 57.474, the SUMlog2($2^{-ddCT}$) value is equal to or higher than a threshold SUMlog2($2^{-ddCT}$) value of 8.725 or the POISE score is equal to or higher than a threshold POISE score of 35; or any combination thereof; and
administering the IFN-I inhibitor to the subject diagnosed as responsive to treatment with the IFN-I inhibitor.

The disclosure also provides a method of determining whether a subject having a type I interferon (IFN-I) mediated disease is responsive to treatment with an IFN-I inhibitor and deciding whether to treat the subject, comprising:
providing a biological sample from the subject;
assaying gene expression of genes DHX58, EIF2AK2, HERC5, IFI44, IFI44L, IFI6, IRF7, PARP9, PLSCR1 and SAMD9L in the biological sample;
determining a combined expression value of the genes DHX58, EIF2AK2, HERC5, IFI44, IFI44L, IFI6, IRF7, PARP9, PLSCR1 and SAMD9L in the biological sample;
diagnosing the subject with the IFN-I mediated disease as responsive to treatment with the IFN-I inhibitor when the combined expression value is equal to or higher than a threshold value or diagnosing the subject with the IFN-I mediated disease as non-responsive to treatment with the IFN-I inhibitor when the combined expression value is less than a threshold value; and
administering the IFN-I inhibitor to the subject diagnosed as responsive to treatment with the IFN-I inhibitor or refraining from administering the IFN-I inhibitor to the subject diagnosed as non-responsive to treatment with the IFN-I inhibitor.

DETAILED DESCRIPTION OF THE DISCLOSURE

Figure 1A:
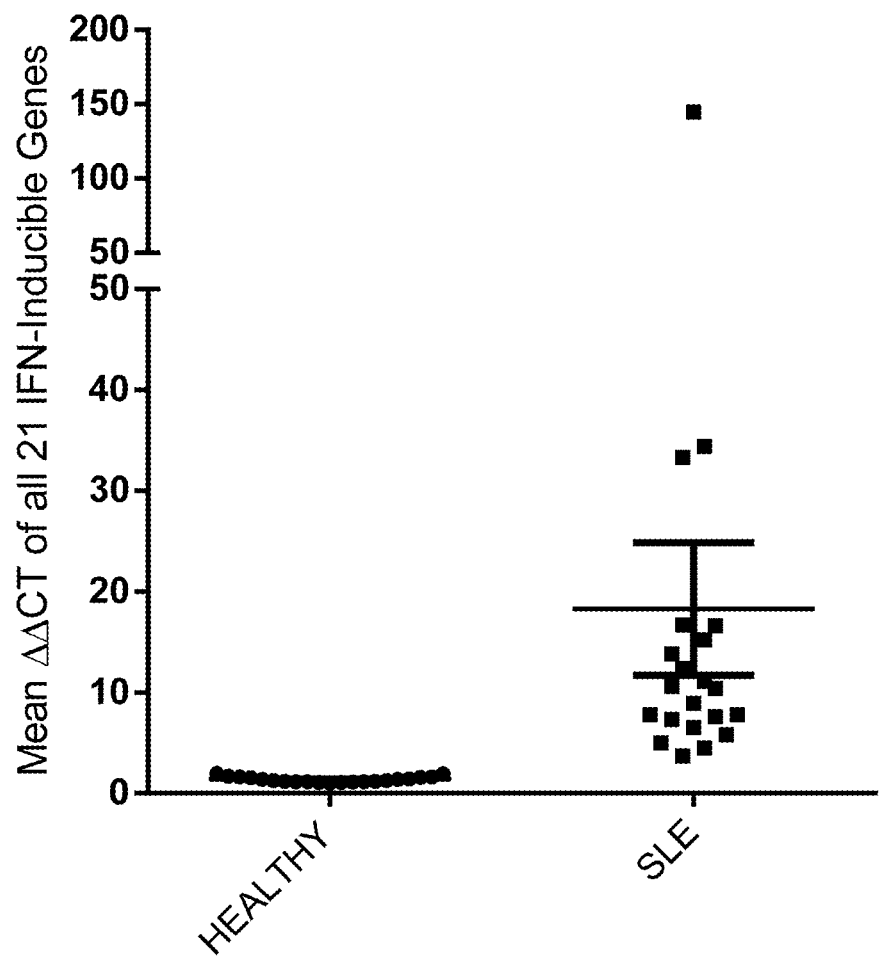
FIG. 1A shows comparison of the mean fold change (ΔΔCT) and standard error of the mean (SEM) of 21 IFN-inducible genes in blood from a healthy and SLE cohort.

All publications, including but not limited to patents and patent applications cited in this specification are herein incorporated by reference as though fully set forth.

It is to be understood that the terminology used herein is for the purpose of describing embodiments only and is not intended to be limiting. Unless defined otherwise, all technical and scientific terms used herein have the same meaning as commonly understood by one of ordinary skill in the art to which the disclosure pertains.

Although any methods and materials similar or equivalent to those described herein may be used in the practice for testing of the present disclosure, exemplary materials and methods are described herein. In describing and claiming the present disclosure, the following terminology will be used.

As used herein and in the claims, the singular forms "a," "and," and "the" include plural reference unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"Diagnosing" or "diagnosis" refers to methods to determine if a subject is suffering from a given disease or condition or may develop a given disease or condition in the future. Diagnosis is typically performed by a physician based on the general guidelines for the disease to be diagnosed.

"Treat" or "treatment" refers to both therapeutic treatment and prophylactic or preventative measures, wherein the object is to prevent or slow down (lessen) an undesired physiological change or disorder, such as complications due to a chronic inflammatory disease or an autoimmune disease. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the condition or disorder is to be prevented.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Type I interferon" or "IFN-I" refers to all native subtypes of human interferon-α (IFNα) and one subtype of interferon-β(IFNβ), interferon-ε (IFNε), interferon-ω (IFNω) and interferon-κ (IFNκ) which bind to a common heterodimeric interferon receptor IFNAR comprising of IFNAR1 and IFNAR2. The amino acid sequences of the various IFN-I proteins, IFNAR1 and IFNAR2 are well known are retrievable from example UNIPROT or Genbank. An exemplary amino acid sequence if IFN-I is that of human IFNω of SEQ ID NO: 15.

```
                                          SEQ ID NO: 15
CDLPQNHGLLSRNTLVLLHQMRRISPFLCLKDRRDFRFPQEMVKGSQLQK

AHVMSVLHEMLQQIFSLFHTERSSAAWNMTLLDQLHTGLHQQLQHLETCL

LQVVGEGESAGAISSPALTLRRYFQGIRVYLKEKKYSDCAWEVVRMEIMK

SLFLSTNMQERLRSKDRDLGSS
```

"Type I interferon (IFN-I) mediated disease" refers to a disease that is at least partially characterized by overexpression of IFN-I inducible gene transcripts and/or elevated IFN-I in blood or tissue.

"Responsive", "responsiveness" or "likely to respond" refers to any kind of improvement or positive response, such as alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

"IFN-I inhibitor", "inhibitor" or "antagonist" is a molecule having the ability to inhibit IFN-I biological activity or reduce IFN-I signature in blood or tissue, or both. Inhibition may be 10%, 20%, 30%, 40%, 50%, 60%, 70%, 75%, 80%, 85%, 90%, 95%, 96%, 97%, 98%, 99% or 100%, or a statistically significant inhibition when compared to a control. Upon receptor binding, IFN-I initiates a signaling cascade through activation of JAK1 and TYK2 leading to the phosphorylation of several STAT family members including STATs 1-6. STAT1 and STAT2 activation leads to the formation of a complex with IFN-regulatory factor 9 (IRF9) and this complex, also known as the IFN-stimulated gene factor 3 (ISGF3) complex, binds to IFN-stimulated response elements (ISREs) in the nucleus resulting in the transcription of many interferon-stimulated genes (ISGs) including IRF7 and CXCL10 (IP-10). IFN-I also modulates cellular function through other pathways including the v-crk sarcoma virus CT10 oncogene homolog (avian)-like (CRKL), mitogen-activated protein kinase (MAPK), phosphoinositide 3-kinase (PI3K), and through nuclear factor kappa-light-chain-enhancer of activated B cells (NF-Kβ). IFN-I inhibitor, for example Jak1 or Tyk2 inhibitor, may inhibit one or more of the above mentioned signaling cascades. IFN-I inhibitor may also reduce disease characteristics in animal models of autoimmune disease, such as NZB/NZW F1 mice that exhibit a time-dependent and female-biased disease with several features of human lupus including glomerulonephritis. Inhibitors of IFN-I also encompass modulators of plasmacytoid dendritic cell survival or function and modulators of innate immune sentinels capable of triggering IFN-I production such as Toll-like receptors TLR3, TLR7, TLR8, TLR9 or modulators of the cGAS-cGAMP-STING pathway.

"IFN-I inducer", "inducer" or "agonist" is a molecule having the ability to potentiate IFN-I biological activity or elevate IFN-I signature in blood or tissue, or both. Potentiation may be 10%, 20%, 30%, 40%, 50%, 60%, 70%, 75%, 80%, 85%, 90%, 95%, 96%, 97%, 98%, 99% or 100%, or a statistically significant inhibition when compared to a control. Such agonists may be Jak1 or Tyk2 agonists.

"Type I interferon signature" or "IFN-I signature" refers to the upregulation of a subset of genes that are modulated by IFN-I. Various IFN-I signatures are known, ranging from a handful to several hundred genes and including the gene set described herein. These signatures may be utilized for example as pharmacodynamic markers to assess target engagement of IFN-I inhibitors for treatment of IFN-I mediated diseases such as Systemic Lupus Erythematosus (SLE) and for purpose of SLE patient stratification or to assess disease activity or progression in any disease or therapeutic efficacy of drugs in which IFN-I may play a role, such as type 1 diabetes, multiple sclerosis, cancers or infectious diseases.

"Baseline IFN-I signature" refers to a signature of interferon inducible genes having the mean fold change across the entire population equal or less than 1.5.

"Gene expression signature" or "signature" as used herein refers to a group of genes, the expression of which indicates a particular status of a cell, tissue, organ, organism or tumor. The genes making up this signature can be expressed, for example, in a specific cell lineage, stage of differentiation, during a particular biological response or in a disease or particular subtype thereof. "IFN-I signature" is encompassed within "gene expression signature".

"Biological sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium, lavage fluids and the like, tissue biopsies, fine needle aspirations, surgically resected tissue, organ cultures or cell cultures.

"Gene expression" refers to translation of information encoded in a gene into a gene product (e.g., RNA, protein). Expressed genes include genes that are transcribed into RNA (e.g., mRNA) that is subsequently translated into protein as well as genes that are transcribed into non-coding functional RNAs that are not translated into protein (e.g., miRNA, tRNA, rRNA, ribozymes etc.).

"Combined expression value" refers to a value or mathematical representation of the level of expression of a combination of test genes, such as a combination of genes DHX58, EIF2AK2, HERC5, IFI44, IFI44L, IFI6, IRF7, PARP9, PLSCR1 and SAMD9L.

"Level of gene expression" or "expression level" refers to the level (e.g., amount) of one or more products (e.g. RNA, protein) encoded by a given gene in a sample or reference standard. The expression level can be relative or absolute.

"Overexpression", "overexpressed", "upregulation", "upregulated", "increased", "increase", "enhance", "enhanced" and "elevated" are all used herein to generally mean an increased expression of one or more genes or a combination of genes (e.g. gene expression signature) in a test sample vs a reference sample by a statically significant amount, or above a pre-identified threshold value. A 1.5-fold increase in the expression level of a gene is indicative of "overexpression".

"Threshold value" refers to a value obtained for the combined expression of genes DHX58, EIF2AK2, HERC5, IFI44, IFI44L, IFI6, IRF7, PARP9, PLSCR1 and SAMD9L that differentiates subjects having elevated IFN-I signature vs. subjects having baseline IFN-I signature with high accuracy. Threshold value may be expressed by various ways depending on the methods of analyzing gene expression. The threshold value may for example be obtained from a population of subjects that are substantially healthy (e.g. subjects who display a baseline IFN-I signature). The threshold value may be stored as a value(s) on a computer or PDA device to permit comparison with a value obtained from a subject using the methods described herein. The threshold value may also be obtained from the same subject e.g., at an earlier time point prior to onset of an IFN-I mediated disease, or prior to initiation of treatment with an IFN-I inhibitor. One of skill in the art can determine an appropriate reference sample for use with the methods described herein.

"Normalizing" refers to a manipulation of discrete expression level data wherein the expression level of one or more test genes is expressed relative to the expression level of one or more control genes, such as one or more housekeeping genes. For example, numerical expression level value one or more housekeeping genes may be deducted from the numerical expression level value of one or more test genes thereby permitting comparison of normalized marker values among a plurality of samples or to a reference.

"Housekeeping gene" refers to a gene encoding a transcript and/or protein that is constitutively expressed and is necessary for basic maintenance and essential cellular functions. A housekeeping gene generally is not expressed in a cell- or tissue-dependent manner, most often being expressed by all cells in a given organism. Some examples of housekeeping proteins include B2M, TFRC, YWHAZ, RPLO, 18S, GUSB, UBC, TBP, GAPDH, PPIA, POLR2A, ACTB, PGK1, HPRT1, IPO8 or HMBS, among others.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient or reduction of IFN-I signature in a subject.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Polynucleotide" refers to a synthetic molecule comprising a chain of nucleotides covalently linked by a sugar-phosphate backbone or other equivalent covalent chemistry. cDNA is an exemplary synthetic polynucleotide.

"Differential expression" refers to a change in expression level of one or more genes or a combination of genes (e.g. gene expression signature) in a test sample vs a reference sample by a statistically significant amount, or above a pre-identified threshold value. A 1.5-fold change in the expression level of a gene is indicative of "differential expression".

"Blocks" or "blocking" refers to a molecule that inhibits interaction of IFN-I and IFNAR. The inhibition may be 60%, 70%, 75%, 80%, 85%, 90%, 95%, 96%, 97%, 98%, 99% or 100%, or a statistically significant inhibition when compared to a control.

"Placebo effect" refers to an improvement in a disease state, such as alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable in a subject who is enrolled into a clinical trial and is not receiving the study drug.

"Once in two weeks" refers to an approximate number, and can include once every 14 days±two days, i.e., every 12 days to every 16 days.

"DHX58" refers to human DExH-box helicase 58 gene that produces a transcript comprising the polynucleotide sequence of NM_024119 (SEQ ID NO: 1). In the sequence, thymine (t) may be substituted for uracil (u).

SEQ ID NO: 1 agtttcagtttccatttctgatttctgctctctgcgctgagcacagcggcaccaggctgagctaagcagggccgccttgggcaggcctacgtggtg gtgcaggcgagacccaggctgggcaaggcgcagtttcagtttccatcttgggtctctgagctgagcagagtggcaccaggctgagttaagtggg -continued

```
actgccctgggcagacctacctactagagcagaatggagcttcggtcctaccaatgggaggtgatcatgcctgccctggagggcaagaatatcat
catctggctgcccacgggtgccggaagacccggcggctgcttatgtggccaagcggcacctagagactgtggatggagccaaggtggttgt
attggtcaacagggtgcacctggtgacccagcatggtgaagagttcaggcgcatgctggatggacgctggaccgtgacaaccctgagtgggga
catgggaccacgtgctggctttggccacctggcccggtgccatgacctgctcatctgcacagcagagcttctgcagatggcactgaccagcccc
gaggaggaggagcacgtggagctcactgtcttctccctgatcgtggtggatgagtgccaccacacgcacaaggacaccgtctacaacgtcatca
tgagccagtacctagaacttaaactccagagggcacagccgctaccccaggtgctgggtctcacagcctccccaggcactgggggggcctcca
aactcgatggggccatcaaccacgtcctgcagctctgtgccaacttggacacgtggtgcatcatgtcacccagaactgctgccccagctgcag
gagcacagccaacagccttgcaaacagtacaacctctgccacaggcgcagccaggatccgtttggggacttgctgaagaagctcatggaccaa
atccatgaccacctggagatgcctgagttgagccggaaatttgggacgcaaatgtatgagcagcaggtggtgaagctgagtgaggctgcggcttt
ggctgggcttcaggagcaacggtgtatgcgcttcacctgaggcgctacaatgacgcgctgctcatccatgacaccgtccgcgccgtggatgcc
ttggctgcgctgcaggatttctatcacagggagcacgtcactaaaacccagatcctgtgtgccgagcgccggctgctggccctgttcgatgaccg
caagaatgagctggcccacttggcaactcatggcccagagaatccaaaactggagatgctggaaaagatcctgcaaaggcagttcagtagctct
aacagccctcggggtatcatcttcacccgcacccgccaaagcgcacactccctcctgctctggctccagcagcagcagggcctgcagactgtgg
acatccgggcccagctactgattgggggctgggaacagcagccagagcacccacatgacccagagggaccagcaagaagtgatccagaagttc
caagatggaaccctgaaccttctggtggccacgagtgtggcggaggaggggctggacatcccacattgcaatgtggtggtgcgttatgggctctt
gaccaatgaaatctccatggtccaggccaggggccgtgcccgggccgatcagagtgtatacgcgtttgtagcaactgaaggtagccgggagct
gaagcgggagctgatcaacgaggcgctggagacgctgatggagcaggcagtggctgctgtgcagaaaatggaccaggccgagtaccaggc
caagatccgggatctgcagcaggcagccttgaccaagcgggggcccaggcagcccagcgggagaaccagcggcagcagttcccagtgga
gcacgtgcagctactctgcatcaactgcatggtggctgtgggccatggcagcgacctgcggaaggtggagggcacccaccatgtcaatgtgaa
ccccaacttctcgaactactataatgtctccaggatcctgtggtcatcaacaaagtcttcaaggactggaagcctgggggtgtcatcagctgcag
gaactgtggggaggtctggggtctgcagatgatctacaagtcagtgaagctgccagtgctcaaagtccgcagcatgctgctggagaccccctcag
gggcggatccaggccaaaaagtggtcccgcgtgcccttctccgtgcctgactttgacttcctgcagcattgtgccgagaacttgtcggacctctcc
ctggactgaccacctcattgctgcagtgcccggtttgggctgtagggggggagagtctgcagcagactccaggcccctccttcctgaatcatc
agctgtgggcatcaggcccaccagccacacaggagtcctgggcaccctggcttaggctcccgcaatgggaaaacaaccggaggggccagagc
ttagtccagacctaccttgtacgcacatagacattttcatatgcactggatggagttagggaaactgaggcaaaagaatttgccatactgtactcaga
atcacgacattccttccctaccaaggccacttctatttttttgaggctcctcataaaaataaatgaaaaaatgggatagaaaaaaaaaaaaaaaaa
```

"EIF2AK2" refers to human eukaryotic translation initiation factor 2 alpha kinase 2 gene that that produces a transcript comprising the polynucleotide sequence of NM_001135651 (SEQ ID NO: 2). In the sequence, thymine (t) may be substituted for uracil (u).

SEQ ID NO: 2

```
agcagacgagggcttgtgcgagaggggccggcggctgcagggaaggcggagtccaaggggaaaacgaaactgagaaccagctctccc
gaagccgcgggtctccggccggcggcggcggcggcggcggcggcgcagtttctggagcaaattcagtttgccttcctggatttgtaaattg
taatgacctcaaaactttagcagttcttccatctgactcaggtttgcttctctggcggtcttcagaatcaacatccacttccgtgattatctgcgtgca
ttttggacaaagcttccaaccaggatacgggaagaagaaatggctggtgatctttcagcaggtttcttcatggaggaacttaatacataccgtcaga
agcagggagtagtacttaaatatcaagaactgcctaattcaggacctccacatgataggaggtttacatttcaagttataatagatggaagagaattt
ccagaaggtgaaggtagatcaaagaaggaagcaaaaaatgccgcagccaaattagctgttgagatacttaataaggaaaagaaggcagttagtc
ctttattattgacaacaacgaattcttcagaaggattatccatggggaattacataggcctttatcaatagaattgcccagaagaaaagactaactgtaa
attatgaacagtgtgcatcgggggtgcatgggccagaaggatttcattataaatgcaaaatgggacagaaagaatatagtattggtacaggttctac
taaacaggaagcaaaacaattggccgctaaacttgcatatcttcagatattatcagaagaaacctcagtgaaatctgactacctgtcctctggttcttttt
gctactacgtgtgagtcccaaagcaactctttagtgaccagcacactcgcttctgaatcatcatctgaaggtgacttctcagcagatacatcagagat
```

-continued

```
aaattctaacagtgacagtttaaacagttcttcgttgcttatgaatggtctcagaaataatcaaaggaaggcaaaaagatctttggcacccagatttga
ccttcctgacatgaaagaaacaaagtatactgtggacaagaggtttggcatggatttttaaagaaatagaattaattggctcaggtggatttggccaa
gttttcaaagcaaaacacagaattgacggaaagacttacgttattaaacgtgttaaatataataacgagaaggcggagcgtgaagtaaaagcattg
gcaaaacttgatcatgtaaatattgttcactacaatggctgttgggatggatttgattatgatcctgagaccagtgatgattctcttgagagcagtgatta
tgatcctgagaacagcaaaaatagttcaaggtcaaagactaagtgccttttcatccaaatggaattctgtgataaagggaccttggaacaatggatt
gaaaaagaagaggcgagaaactagacaaagttttggctttggaactctttgaacaaataacaaaaggggtggattatatacattcaaaaaaattaa
ttcatagagatcttaagccaagtaatatattcttagtagatacaaaacaagtaaagattggagactttggacttgtaacatctctgaaaaatgatggaaa
gcgaacaaggagtaagggaactttgcgatacatgagcccagaacagatttcttcgcaagactatggaaaggaagtggacctctacgctttgggg
ctaattcttgctgaacttcttcatgtatgtgacactgcttttgaaacatcaaagttttttcacagacctacgggatggcatcatctcagatatatttgataaa
aaagaaaaaactcttctacagaaatactctcaaagaaacctgaggatcgacctaacacatctgaaatactaaggaccttgactgtgtggaagaaaa
gcccagagaaaaatgaacgacacacatgttagagcccttctgaaaaagtatcctgcttctgatatgcagttttccttaaattatctaaaatctgctagggaata
tcaatagatatttaccttttattttaatgtttcctttaattttttactattttttactaatctttctgcagaaacagaaaggttttcttcttttttgcttcaaaaa
cattcttacattttacttttttcctggctcatctctttattctttttttttttttaaagacagagtctcgctctgttgcccaggctggagtgcaatgacacagtc
gctcactgcaacttctgcctcttgggttcaagtgattctcctgcctcagcctcctgagtagctggattacaggcatgtgccacccacccaactaatttttt
gtgttttaataaagacaggggtttcaccatgttggccaggctggtctcaaactcctgacctcaagtaatccacctgcctcggcctcccaaagtgctgg
gattacagggatgagccaccgcgcccagcctcatctctttgttctaaagatggaaaaaccaccccccaaattttctttttatactattaatgaatcaatca
attcatatctatttattaaatttctaccgcttttaggccaaaaaatgtaagatcgttctctgcctcacatagcttacaagccagctggagaaatatggta
ctcattaaaaaaaaaaaaaaagtgatgtacaaccacttcggaaaacaatttggcattatctagtaaagttgaatccatgtatacccacatagctatca
attctattcctacatacgtgcttacaagaatgtccataaaaccctgtttataatagccaaaagaacagggaacaaccataatgcacatcaaaagaaga
atggattaaaaaaattatattcacacacaggagtactatatagtattgaaaacaattgaagtacagctaaatgtaataacgtaacacaatacaactctc
agaaacataatgttaagcgaacaaagcaggttttcagaaaatatatgcagaataattccatttatataaagttccagagcatgcaaaactaaatcattttt
gtataaaaaacccaacaaatgtgatgagacaataatgggaaggaagggaatgagaaatattaaattctggatggtggttatctttgagggaggggg
aatgatgtgattggggaaatggactttcaaaggtaatggtaacttccttaagctggatggtaggtccactagtgtttgctgcatagttataccttttatctt
aaatacattttgtatctattgtaacaaccactttaaagacaaccgtgctgtaaggcagtagctaaaaacagaaaatagtccatcgggaagggtaagat
ggctttctgctgagcacagggctagaagtgacagcccagtgggccttccaactatatgccagggtgttagatgagtagagaggagaccaccag
gaagtctggacaaggggtctggcatgagctctggagaagatatatttgaggaacatggggtatgctagtttgttgtcctgaattgctgtagagaaga
taatttaaattgcatcttagaagacgaccctgagggtgaatttcaacttagggcaattgttttagtttgtttcttattggtttaaatggatacttgaagctgg
ataatttataaggaaaagagatttatatgacttacagttctgcaggctgtacaagaaacatggcaccagcatctgcttcttcccggctgcttccactc
atggtggaaggtgaaggggagccggatgtgcagagatcatatggcaagagggaagcaagagagcgagggagaaggtgccaggctctttta
aataaccggctcttgagggaactaatagattgagaactccttgcttctcctccccagcacaccccaccccagggacggcattaatgtattcatgag
gggtcttcccccatgacccaaacacctcccatcaggccccacctccaacactgggatcaaatttcaacatgagattttggggacaaacatgcaaa
ctatagcagcaaccagctaccattctaaaactgccatatgattttaggatttttaaaaagggccaaatttaggttaagcaaaaaaaaaaaaaaaaaa
```

"HERC5" refers to human HECT and RLD domain containing E3 ubiquitin protein ligase 5) gene that produces a transcript comprising the polynucleotide sequence of NM_016323.3 (SEQ ID NO: 3). In the sequence, thymine (t) may be substituted for uracil (u).

SEQ ID NO: 3

```
tcagtagctgaggctgcggttccccgacgccacgcagctgcgcgcagctggttcccgctctgcagcgcaacgcctgaggcagtgggcgcgct
cagtcccgggaccaggcgttctctcctctcgcctctgggcctgggaccccgcaaagcggcgatggagcggaggtcgcggaggaagtcgcgg
cgcaacgggcgctcgaccgcgggcaaggccgccgcgacccagcccgcgaagtctccgggcgcacagctctggctctttcccagccgcg
ggcctccaccgcgcgctgctccggagggtggaggtgacgcgccaactctgctgctcgccggggcgcctcgcggtcttggaacgcggcgggg
cgggcgtccaggttcaccagctgctcgccgggagcggcggcgcccggacgccgaaatgcattaaattaggaaaaaacatgaagatacattccg
```

-continued

```
tggaccaaggagcagagcacatgctgattctctcatcagatggaaaaccatttgagtatgacaactatagcatgaaacatctaaggtttgaaagcat
tttacaagaaaaaaaaataattcagatcacatgtggagattaccattctcttgcactctcaaaaggtggtgagcttttgcctggggacagaacctgca
tgggcagcttggagttggaaggaaatttccctcaaccaccacaccacagattgtggagcacctcgcaggagtacccttggctcagatttctgccg
gagaagcccacagcatggccttatccatgtctggcaacatttattcatgggaaaaaatgaatgtggacaactaggcctgggccacactgagagt
aaagatgatccatcccttattgaaggactagacaatcagaaagttgaatttgtcgcttgtggtggctctcacagtgccctactcacacaggatgggct
gctgtttactttcggtgctggaaaacatgggcaacttggtcataattcaacacagaatgagctaagaccctgtttggtggctgagcttgttgggtatag
agtgactcagatagcatgtggaaggtggcacacacttgcctatgtttctgatttgggaaaggtcttttcctttggttctggaaaagatggacaactgg
gaaatggtggaacacgtgaccagctgatgccgcttccagtgaaagtatcatcaagtgaagaactcaaacttgaaagccatacctcagaaaagga
gttaataatgattgctggagggaatcaaagcattttgctctggataaagaaagagaattcatatgttaatctgaagaggacaattcctactctgaatga
agggactgtaaagagatggattgctgatgtggagactaaacggtggcagagcacaaaagggaaatccaagagatattttcatctcctgcttgtct
aactggaagttttttaaggaaaagaagaactacagaaatgatgcctgtttatttggacttaaataaagcaagaaacatcttcaaggagttaacccaaa
aggactggattactaacatgataaccacctgcctcaaagataatctgctcaaaagacttccatttcattctccaccccaagaagctttagaaatttctt
ccttctcccagaatgtcctatgatgcatatttccaacaactgggagagccttgtggttccatttgcaaaggttgtttgtaaaatgagtgaccagtcttca
ctggttctggaagagtattgggcaactctgcaagaatccactttcagcaaactggtccagatgtttaaaacagccgtcatatgccagttggattactg
ggatgaaagtgctgaggagaatggtaatgttcaagctctcctagaaatgttgaagaagctgcacagggtaaaccaggtgaaatgtcaactacctg
aaagtattttccaagtagacgaactcttgcaccgtctcaattttttttgtagaagtatgcagaaggtacttgtggaaaatgactgtggacgcttcagaaa
atgtacaatgctgcgtcatattcagtcactttccatttatctttaataatctgtcgaaaattaaactactacatacagacacacttttaaaaatagagagta
aaaaacataaagcttatcttaggtcggcagcaattgaggaagaaagagagtctgaattcgctttgaggcccacgtttgatctaacagtcagaagga
atcacttgattgaggatgtttgaatcagctaagtcaatttgagaatgaagacctgaggaaagagttatgggtttcatttagtggagaaattgggtatg
acctcggaggagtcaagaaagagttcttctactgtctgtttgcagagatgatccagccggaatatgggatgttcatgtatcctgaagggcttcctg
catgtggtttcctgtcaagcctaaatttgagaagaaaagatacttctttttttggggttctatgtggactttccctgttcaattgcaatgttgccaaccttcct
ttcccactggcactgtttaagaaacttttggaccaaatgccatcattggaagacttgaaagaactcagtcctgatttgggaaagaatttgcaaacactt
ctggatgatgaaggtgataactttgaggaagtattttacatccattttaatgtgcactgggacagaaacgacacaaacttaattcctaatggaagtagc
ataactgtcaaccagactaacaagagagactatgtttctaagtatatcaattacattttcaacgactctgtaaaggcggtttatgaagaatttcggaga
ggattttataaaatgtgcgacgaagacattatcaaattattccaccccgaagaactgaaggatgtgattgttggaaatacagattatgattggaaaac
atttgaaaagaatgcacgttatgaaccaggatataacagttcacatcccaccatagtgatgttttggaaggctttccacaaattgactctggaagaaa
agaaaaaattccttgtatttcttacaggaactgacagactacaaatgaaagatttaaataatatgaaaataacattttgctgtcctgaaagttggaatga
aagagaccctataagagcactgacatgtttcagtgtcctcttcctccctaaatattctacaatggaaacagttgaagaagcgcttcaagaagccatcaacaac
aacagaggatttggctgaccagcttcttgtccaacagccttattttgttgttgttatcgttgttgttgttgttgttgttgtttctctactttgttttg
ttttaggcttttagcagcctgaagccatggttttcatttctgtctctagtgataagcaggaaagagggatgaagaagagggtttactggccggttaga
acccgtgactgtattctctcccttggatacccctatgcctacatcatattccttacctcttttgggaaatattttttcaaaaataaaataaccgaaaaattaa
cataaaa
```

"IFI44" refers to interferon induced protein 44 gene that produces a transcript comprising the polynucleotide sequence of NM_006417.4 (SEQ ID NO: 4). In the sequence, thymine (t) may be substituted for uracil (u).

SEQ ID NO: 4

```
tctttgaagcttcaaggctgctgaataatttccttctcccatttttgtgcctgcctagctatccagacagagcagctaccctcagctctagctgatactac
agacagtacaacagatcaagaagtatggcagtgacaactcgtttgacatggttgcacgaaaagatcctgcaaaatcattttggagggaagcggctt
agccttctctataagggtagtgtccatggattccgtaatggagttttgcttgacagatgttgtaatcaagggcctactctaacagtgatttatagtgaag
atcatattattggagcatatgcagaagagagttaccaggaaggaaagtatgcttccatcatccttttttgcacttcaagatactaaaatttcagaatgga
aactaggactatgtacaccagaaacactgttttgttgtgatgttacaaaatataactccccaactaatttccagatagatggaagaaatagaaaagtga
```

-continued

```
ttatggacttaaagacaatggaaaatcttggacttgctcaaaattgtactatctctattcaggattatgaagttttcgatgcgaagattcactggatgaa
agaaagataaaaggggtcattgagctcaggaagagcttactgtctgccttgagaacttatgaaccatatggatcccctggttcaacaaatacgaattc
tgctgctgggtccaattggagctgggaagtccagcttttcaactcagtgaggtctgttttccaagggcatgtaacgcatcaggctttggtggcact
aatacaactgggatatctgagaagtataggacatactctattagagacgggaaagatggcaaatacctgccgtttattctgtgtgactcactgggc
tgagtgagaaagaaggcggcctgtgcagggatgacatattctatatcttgaacggtaacattcgtgatagataccagtttaatcccatggaatcaatc
aaattaaatcatcatgactacattgattccccatcgctgaaggacagaattcattgtgtggcatttgtatttgatgccagctctattcaatacttctcctct
cagatgatagtaaagatcaaaagaattcgaagggagttggtaaacgctggtgtggtacatgtggctttgctcactcatgtggatagcatggatttgat
tacaaaaggtgaccttatagaaatagagagatgtgagcctgtgaggtccaagctagaggaagtccaaagaaaacttggatttgctctttctgacatc
tcggtggttagcaattattcctctgagtgggagctggaccctgtaaaggatgttctaattctttctgctctgagacgaatgctatgggctgcagatgac
ttcttagaggatttgccttttgagcaaatagggaatctaagggaggaaattatcaactgtgcacaaggaaaaaaatagatatgtgaaaggttcacgta
aatttcctcacatcacagaagattaaaattcagaaaggagaaaacacagaccaaagagaagtatctaagaccaaagggatgtgttttattaatgtct
aggatgaagaaatgcatagaacattgtagtacttgtaaataactagaaataacatgatttagtcataattgtgaaaaataataattttcttggattta
tgttctgtatctgtgaaaaataaatttcttataaaactcgggtctaaaaaaaaaaaaaaaaa
```

"IFI44L" refers to interferon induced protein 44 like gene that produces a transcript comprising the polynucleotide sequence of NM_006820.3 (SEQ ID NO: 5). In the sequence, thymine (t) may be substituted for uracil (u).

SEQ ID NO: 5
```
aaagttagtggcagttggcatgctgccagctgagttttttgctgctttgagtctcagttttcttctttcctagagtctctgaagccacagatctcttaaga
actttctgtctccaaaccgtggctgctcgataaatcagacagaacagttaatcctcaatttaagcctgatctaacccctagaaacagatatagaacaat
ggaagtgacaacaagattgacatggaatgatgaaaatcatctgcgcaagctgcttggaaatgtttctttgagtcttctctataagtctagtgttcatgg
aggtagcattgaagatatggttgaaagatgcagccgtcagggatgtactataacaatggcttacattgattacaatatgattgtagcctttatgcttgg
aaattatattaatttacatgaaagttctacagagccaaatgattccctatggttttcacttcaaaagaaaaatgacaccactgaaatagaaactttactctt
aaatacagcaccaaaaattattgatgagcaactggtgtgtcgtttatcgaaaacggatattttcattatatgtcgagataataaaatttatctagataaaa
tgataacaagaaacttgaaactaaggttttatggccaccgtcagtatttggaatgtgaagttttcgagttgaaggaattaaggataacctagacgac
ataaagaggataattaaagccagagagcacagaaataggcttctagcagacatcagagactataggccctatgcagacttggtttcagaaattcgt
attccttttggtgggtccagttgggtctggaaagtccagttttttcaattcagtcaagtctatttttcatggccatgtgactggccaagccgtagtggggtc
tgatatcaccagcataaccgagcggtataggatatattctgttaaagatggaaaaaatggaaaatctctgccatttatgttgtgtgacactatgggct
agatgggcagaaggagcaggactgtgcatggatgacattccccacatcttaaaaggttgtatgccagacagatatcagtttaattcccgtaaacc
aattacacctgagcattctactttatcacctctccatctctgaaggacaggattcactgtgtggcttatgtcttagacatcaactctattgacaatctcta
ctctaaaatgttggcaaaagtgaagcaagttcacaaagaagtattaaactgtggtatagcatatgtggccttgcttactaaagtggatgattgcagtg
aggttcttcaagacaacttttttaaacatgagtagatctatgacttctcaaagccgggtcatgaatgtccataaaatgctaggcattcctatttccaatattt
tgatggttggaaattatgcttcagatttggaactggaccccatgaaggatattctcatcctctctgcactgaggcagatgctgcgggctgcagatgat
ttttttagaagatttgcctcttgaggaaactggtgcaattgagagagcgttacagcccgcatttgagataagttgccttgattctgacatttggcccagc
ctgtactggtgtgccgcaatgagagtcaatctctattgacagcctgcttcagattttgcttttgttcgttttgccttctgtccttggaacagtcatatctcaa
gttcaaaggccaaaacctgagaagcggtgggctaagataggtcctactgcaaaccacccctccatatttccgtaccatttacaattcagtttctgtga
catctttttaaaccactggaggaaaaatgagatattctctaatttattcttctataacactctatatagagctatgtgagtactaatcacattgaataatagtt
ataaaattattgtatagacatctgcttcttaaacagattgtgagttcttgagaaacagcgtggatttacttatctgtgtattcacagagcttagcacagt
gcctggtaatgagcaagcatacttgccattacttttccttcccactctctccaacatcacattcactttaaattttctgtatatagaaaggaaactagcc
tgggcaacatgatgaaacccatctccactgcaaaaaaaaaaaaaaaaataagaaagaacaaaacaaacccacaaaaattagctgggtatga
tggcacgtgcctgtagtcccagttactcaggatgattgattgagcctggaggtggaggctacagtgagctgagattgtgccactgtactctagcca
gggagaaagagtgagatcctggctcaaaaaaaaccaaataaaacaaaacaaacaaacgaaaaacagaaaggaagactgaaagagaatgaaaa
```

-continued

```
gctggggagaggaaataaaaataaagaaggaagagtgtttcatttatatctgaatgaaaatatgaatgactctaagtaattgaattaattaaaatgagcca
acttttttttaacaatttacattttatttctatgggaaaaaataaatattcctcttctaacaaacccatgcttgattttcattaattgaattccaaatcatcct
agccatgtgtccttccatttaggttactggggcaaatcagtaagaaagttcttatatttatgctccaaataattctgaagtcctcttactagctgtgaaagc
tagtactattaagaaagaaaacaaaattcccaaaagatagctttcacttttttttttccttaaagacttcctaattctcttctccaaattcttagtcttcttca
aaataatatgctttggttcaatagttatccacattctgacagtctaatttagttttaatcagaattatactcatcttttgggtagtcatagatattaagaaagc
aagagtttcttatgtccagttatggaatatttcctaaagcaaggctgcaggtgaagttgtgctcaagtgaatgttcaggagacacaattcagtggaag
aaattaagtctttaaaaaagacctaggaataggagaaccatggaaattgaggaggtaggcctacaagtagatattgggaacaaaattagagaggc
aaccagaaaagttattttaggctcaccagagttgttcttattgcacagtaacacaccaatataccaaaacagcaggtattgcagtagagaaagagtt
taataattgaatggcagaaaaatgaggaaggttgaggaaacctcaaatctacctccctgctgagtctaagtttaggattttttaagagaaaggcaggt
aaggtgctgaaggtctggagctgctgatttgttggggtataggaatgaaatgaaacatacagagatgaaaactggaagttttttttttgtttgtttttgtttttt
ttttgttgttgttttttttttttttttttttgctgagtcaattccttggagggggtcttcagactgactggtgtcagcagacccatgggattccaagatct
ggaaacttttagatagaaacttgatgtttcttaacgttacatatattatcttatagaaataactaagggaagttagtgccttgtgaccacatctatgtga
cttttaggcagtaagaaactataaggaaaggagctaacagtcatgctgtaagtagctacagggaattggcttaaagggcaagttggttagtacttag
ctgtgttttattcaaagtctacattttatgtagtggttaatgtttgctgttcattaggatggtttcacagttaccatacaaatgtagaagcaacaggtccaa
aaagtagggcatgatttttctccatgtaatccaggagaaaacaagccatgaccattgttggttgggagactgaaggtgattgaaggttcaccatcat
cctcaccaacttttgggccataattcacccaaccctttggtggagcctgaaaaaaatctgggcagaatgtaggacttctttattttgtttaaagggggta
acacagagtgcccttatgaaggagttggagatcctgcaaggaagagaaggagtgaaggagagatcaagagagagaaacaatgaggaacattt
catttgacccaacatccttaggagcataaatgttgacactaagttatcccttttgtgctaaaatggacagtattggcaaaatgataccacaacttcttat
tctctggctctatattgctttggaaacacttaaacatcaaatggagttaaatacatatttgaaatttaggttaggaaatattggtgaggaggcctcaaaa
agggggaaacatcttttgtctgggaggatattttccattttgtggatttccctgatcttttctaccaccctgagggtggtgggaattatcattttgctac
attttagaggtcatccaggattttgaaactttacattcttacggttaagcaagatgtacagctcagtcaaagacactaaattcttcttagaaaaatagt
gctaaggagtatagcagatgacctatatgtgtgttggctgggagaatatcatcttaaagtgagagtgatgttgtggagacagttgaaatgtcaatgct
agagcctctgtggtgtgaatgggcacgttaggttgttgcattagaaagtgactgtttctgacagaaatttgtagctttgtgcaaactcacccaccatct
acctcaataaaatatagagaaaagaaaaatagagcagtttgagttctatgaggtatgcaggcccagagagacataagtatgttcctttagtcttgctt
cctgtgtgccacactgcccctccacaaccatagctgggggcaattgtttaaagtcattttgttcccgactagctgccttgcacattatcttcatttttcctg
gaatttgatacagagagcaatttatagccaattgatagcttatgctgtttcaatgtaaattcgtggtaaataacttaggaactgcctcttctttt
tctttgaaaacctacttataactgttgctaataagaatgtgtattgttcaggacaacttgtctccatacagttgggttgtaaccctcatgcttggcccaaat
aaactctctacttatatcagttttttcctacacttcttccttttaggtcaacaataccaagaggggttactgtgctgggtaatgtgtaaacttgtgtcttgttta
gaaagataaatttaaagactatcacattgcttttttcataaaacaagacaggtctacaattaattttatttttgacgcaaattgatagggggggccaagtaagc
cccatatgcttaatgatcagctgatgaataatcatctcctagcaacataactcaatctaatgctaaggtacccacaagatggcaaggctgatcaaagt
cgtcatggaatcctgcaaccaaaagccatgggaatttggaagccctcaaatcccattcctaatctgatgagtctatggaccaatttgtggaggacag
tagattaaatagatctgattttttgccatcaatgtaaggaggataaaaacttgcataccaattgtacacccttgcaaaatctttctctgatgttggagaaaa
tgggccagtgagatcatggatatagaagtacagtcaatgttcagctgtaccctcccacaatcccacttccttcctcaacacaattcaaacaaatagac
tcagactgtttcaggctccaggacaggaagtgcagtgtaggcaaaattgcaaaaattgagggcacaggggtggaggtgggggggttgaataac
aagctgtgctaaataattacgtgtaaatatattttttcattttaaaaattgatttcttttgcacattccatgacaatatatgtcacatttttaaaataaatg
caaagaagcatacatccaaaaaaaaaaaaaaaa
```

"IFI6" refers to interferon alpha inducible protein 6 gene that produces a transcript comprising the polynucleotide sequence of NM_022873.2 (SEQ ID NO: 6). In the sequence, thymine (t) may be substituted for uracil (u).

SEQ ID NO: 6

```
ccagccttcagccggagaaccgtttactcgctgctgtgcccatctatcagcaggctccgggctgaagattgcttctcttctctcctccaaggtctagt
gacggagcccgcgcggcggccaccatgcggcagaaggcggtatcgcttttcttgtgctacctgctgctcttcacttgcagtggggtggaggca
ggtgagaatgcgggtaaggatgcaggtaagaaaaagtgctcggagagctcggacagcggctccgggttctggaaggccctgaccttcatggc
cgtcggaggaggactcgcagtcgccgggctgcccgcgctgggcttcaccggcgccggcatgcgggccaactcggtggctgcctcgctgatg
agctggtctgcgatcctgaatgggggcggcgtgcccgccggggggctagtggccacgctgcagagcctcggggctggtggcagcagcgtcg
tcataggtaatattggtgccctgatgggctacgccacccacaagtatctcgatagtgaggaggatgaggagtagccagcagctcccagaacctcttcttc
cttcttggcctaactcttccagttaggatctagaactttgcctttttttttttttttttttttgagatgggttctcactatattgtccaggctagagtgca
gtggctattcacagatgcgaacatagtacactgcagcctccaactcctagcctcaagtgatcctcctgtctcaacctcccaagtaggattacaagca
tgcgccgacgatgcccagaatccagaactttgtctatcactctcccaacaacctagatgtgaaaacagaataaacttcacccagaaaacactt
```

"IRF7" refers to interferon regulatory factor 7 gene that produces a transcript comprising the polynucleotide sequence of NM_004031.3 (SEQ ID NO: 7). In the sequence, thymine (t) may be substituted for uracil (u).

SEQ ID NO: 7

```
gagacgaaacttcccgtcccggcggctctggcacccagggtccggcctgcgccttcccgccaggcctggacactggttcaacacctgtgacttc
atgtgtgcgcgccggccacacctgcagtcacacctgtagccccctctgccaagagatccataccgaggcagcgtcggtggctacaagccctca
gtccacacctgtggacacctgtgacacctggccacacgacctgtggccgcggcctggcgtctgctgcgacaggagcccttacctcccctgttata
acacctgaccgccacctaactgccctgcagaaggagcaatggccttggctcctgagaggtaagagcccggcccaccctctccagatgccagt
ccccgagcgccctgcagccggccctgactctccgcggccgggcacccgcagggcagcccacgcgtgctgttcggagagtggctccttgga
gagatcagcagcggctgctatgaggggctgcagtggctggacgaggcccgcacctgtttccgcgtgccctggaagcacttcgcgcgcaagga
cctgagcgaggccgacgcgcgcatcttcaaggcctgggctgtggcccgcggcaggtggccgcctagcagcaggggaggtggcccgccccc
cgaggctgagactgcggagcgcgccggctggaaaaccaacttccgctgcgcactgcgcagcacgcgtcgcttcgtgatgctgcgggataact
cggggacccggccgacccgcacaaggtgtacgcgctcagccgggagctgtgctggcgagaaggcccaggcacggaccagactgaggca
gaggcccccgcagctgtcccaccaccacagggggggccccagggccattcctggcacacacacatgctggactccaagccccaggccccc
tccctgccccagctggtgacaaggggggacctcctgctccaggcagtgcaacagagctgcctggcagaccatctgctgacagcgtcatggggg
gcagatccagtcccaaccaaggctcctggagagggacaagaagggcttcccctgactggggcctgtgc
tggaggcccagggctccctgctggggagctgtacggggggcagtagagacgaccccagccccgggcccagcccgcggcactaacgac
aggcgaggccgcggccccagagtccccgcaccaggcagagccgtacctgtcaccctcccaagcgcctgcaccgcggtgcaagagcccag
cccaggggcgctggacgtgaccatcatgtacaagggccgcacggtgctgcagaaggtggtgggacaccccgagctgcacgttcctatacggcc
ccccagacccagctgtccgggccacagaccccagcaggtagcattcccagccctgccgagctcccggaccagaagcagctgcgctacac
ggaggaactgctgcggcacgtggcccctgggttgcacctggagcttcggggccacagctgtgggcccggcgcatgggcaagtgcaaggtg
tactgggaggtgggcggaccccaggctccgccagcccctccaccccagcctgcctgctgcctcggaactgtgacaccccatcttcgacttca
gagtcttcttccaagagctggtggaattccgggcacggcagcgccgtggctcccacgctataccatctacctgggcttcgggcaggacctgtca
gctgggaggcccaaggagaagagcctggtcctggtgaagctggaaccctggctgtgccgagtgcacctagagggcacgcagcgtgagggtg
tgtcttccctggatagcagcagcctcagcctctgcctgtccagcgccaacagcctctatgacgacatcgagtgcttccttatggagctggagcagc
ccgcctagaacccagtctaatgagaactccagaaagctggagcagcccacctagagctggccgcggccgcccagtctaataaaaagaactcc
agaacacgta
```

"PARP9" refers to poly(ADP-ribose) polymerase family member 9 that produces a transcript comprising the polynucleotide sequence of NM_001146102.1 (SEQ ID NO: 8). In the sequence, thymine (t) may be substituted for uracil (u).

SEQ ID NO: 8 agagccgcttcccccctcctccctgtgctgtctgcaccgaggagagcggcctgccggaagtgggccaccatatctggaaactacagtctatgcttt gaagcgcaaaagggaataaacattttaaagactccccggggacctggaggatggacttttccatggtggccggagcagcagcttacaatgaaa aatcaggtaggattacctcgctctcactcttgtttcagaaagtctttgctcagatctttcctcagtggagaaaggggaatacagaagaatgtctcccct acaagtgctcagagactggtgctcttggagaaaactatagttggcaaattcccattaaccacaatgacttcaaaattttaaaaaataatgagcgtcag ctgtgtgaagtcctccagaataagtttggctgtatctctaccctggtctctccagttcaggaaggcaacagcaaatctctgcaagtgttcagaaaaat gctgactcctaggatagagttatcagtctggaaagatgacctcaccacacatgctgttgatgctgtggtgaatgcagccaatgaagatcttctgcat ggggaggcctggccctggccctggtaaaagctggtggatttgaaatccaagaagagagcaaacagtttgttgccagatatggtaaagtgtcag ctggtgagatagctgtcacgggagcagggaggcttccctgcaaacagatcatccatgctgttgggcctcggtggatggaatgggataaacagg gatgtactggaaagctgcagagggccattgtaagtattctgaattatgtcatctataaaaatactcacattaagacagtagcaattccagccttgagct ctgggattttcagttccctctgaatttgtgtacaaagactattgtagagactatccgggttagtttgcaagggaagccaatgatgagtaatttgaaag aaattcacctggtgagcaatgaggaccctactgttgctgcctttaaagctgcttcagaattcatcctagggaagagtgagctgggacaagaaacca ccccttctttcaatgcaatggtcgtgaacaacctgaccctccagattgtccagggccacattgaatggcagacggcagatgtaattgttaattctgta aacccacatgatattacagttggacctgtggcaaagtcaattctacaacaagcaggagttgaaatgaaatcggaatttcttgccacaaaggctaaa cagtttcaacggtcccagttggtactggtcacaaaaggatttaacttgttctgtaaatatatataccatgtactgtggcattcagaatttcctaaacctca gatattaaaacatgcaatgaaggagtgtttggaaaaatgcattgagcaaaatataacttccatttcctttcctgcccttgggactggaaacatggaaat aaagaaggaaacagcagcagagattttgtttgatgaagttttaacatttgccaaagaccatgtaaaacaccagttaactgtaaaatttgtgatctttcc aacagatttggagatatataaggctttcagttctgaaatggcaaagaggtccaagatgctgagtttgaacaattacagtgtccccagtcaaccaga gaggagaaaagagaaatgggcttgaagctagatctcctgccatcaatctgatgggattcaacgtggaagagatgtatgaggcccacgcatgga tccaaagaatcctgagtctccagaaccaccacatcattgagaataatcatattctgtaccttgggagaaaggaacatgacattttgtctcagcttcag aaaacttcaagtgtctccatcacagaaattatcagcccaggaaggacagagttagagattgaaggagcccgggctgacctcattgaggtggttat gaacattgaagatatgctttgtaaagtacaggaggaaatggcaaggaaaaaggagcgaggcctttggcgctcgttaggacagtggactattcag caacaaaaacccaagacgaaatgaaagaaaatatcatatttctgaaatgtcctgtgcctccaactcaagagcttctagatcaaaagaaacagtttg aaaaatgtggtttgcaggttctaaaggtggagaagatagacaatgaggtccttatggctgccttcaaagaaagaagaaaatgatggaagaaaaa ctgcacaggcaacctgtgagccataggctgtttcagcaagtcccataccagttctgcaatgtggtatgcagagttggctttcaaagaatgtactcga caccttgcgatccaaaatacggagctggcatatacttcaccaagaacctcaaaaacctggcagagaaggccaagaaaatctctgctgcagataa gctgatctatgtgtttgaggctgaagtactcacaggcttcttctgccagggacatccgttaaatattgttccccaccactgagtcctggagctataga tggtcatgacagtgtggttgacaatgtctccagccctgaaacctttgttatttttagtggcatgcaggctataccctcagtatttgtggacatgcacccag gaatatgtacagtcacaagattactcatcaggaccaatgagacccttgcacagcatccttggaggggattcgcaagtggcagccctgttgattaat ctctacatcattttaacagctggtatggccttacctgggtgaactaaccaaataatgaccatcgatggctcaaagagtggcttgaatatatcccatgg gttatctgtatggactgactgggttattgaaggactagccacatactagcatcttagtgcctttatctgtctttatgtcttgggggttgggtaggtagat accaaatgaaacactttcaggaccttccttcctcttgcagttgttctttaatctcctttactagaggagataaatattttgcatataatgaagaaattttcta gtatataacgcaggccttttattttctaaaatgatgatagtataaaaatgttaggataacagaatgattttagattttccagagaatattataaagtgcttta ggtatgaaaataaatcatctttgtctgattaactggctctgaaaaaaaaaaaaaaaa "PLSCR1" refers to phospholipid scramblase 1 gene that produces a transcript comprising the polynucleotide sequence of NM_021105.2 (SEQ ID NO: 9). In the sequence, thymine (t) may be substituted for uracil (u).

SEQ ID NO: 9

```
caccggacaaacgtctctggagtctctccaatgagcaagaaagcaagtcgggggtaggggagggggcctcacaccaggggggggcgcagtc
cctcctccagctccttcaccctccagtagtctcgtgggtccccgagcgccagcgcgggaaccgggaaaaggaaaccgtgttgtgtacgtaagat
tcaggaaacgaaaccaggagccgcgggtgttggcgcaaaggttactcccagacccttttccggctgacttctgagaaggttgcgcagcagctgt
gcccggcagtctagaggcgcagaagaggaagccatcgcctggccccggctctctggaccttgtctcgctcgggagcggaaacagcggcagc
cagagaactgttttaatcatggacaaacaaaactcacagatgaatgcttctcacccgaaacaaacttgccagttgggtatcctcctcagtatccac
cgacagcattccaaggacctccaggatatagtggctaccctgggccccaggtcagctacccaccccaccagccggccattcaggtcctggcc
cagctggctttcctgtcccaaatcagccagtgtataatcagccagtatataatcagccagttggagctgcaggggtaccatggatgccagcgcca
cagcctccattaaactgtccacctggattagaatatttaagtcagatagatcagatactgattcatcagcaaattgaacttctggaagttttaacaggtt
ttgaaactaataacaaatatgaaattaagaacagctttggacagagggtttactttgcagcggaagatactgattgctgtacccgaaattgctgtggg
ccatctagaccttttaccttgaggattattgataatatgggtcaagaagtcataactctggagagaccactaagatgtagcagctgttgttgtccctgc
tgccttcaggagatagaaatccaagctcctcctggtgtaccaataggttatgttattcagacttggcacccatgtctaccaaagtttacaattcaaaat
gagaaaagagaggatgtactaaaaataagtggtccatgtgttgtgtgcagctgttgtggagatgttgattttgagattaaatctcttgatgaacagtgt
gtggttggcaaaatttccaagcactggactggaattttgagagaggcatttacagacgctgataactttggaatccagttcccttttagaccttgatgtt
aaaatgaaagctgtaatgattggtgcctgtttcctcattgacttcatgttttttgaaagcactggcagccaggaacaaaaatcaggagtgtggtagtg
gattagtgaaagtctcctcaggaaatctgaagtctgtatattgattgagactatctaaactcatacctgtatgaattaagctgtaaggcctgtagctctggttg
tatacttttgcttttcaaattatagtttatcttctgtataactgatttataaaggtttttgtacattttttaatactcattgtcaatttgagaaaaaggacata
tgagttttttgcatttattaatgaaacttcctttgaaaaactgctttgaattatgatctctgattcattgtccatttttactaccaaatattaactaaggccttat
taattttatataaattatatcttgtcctattaaatctagttacaatttatttcatgcataagagctaatgttattttgcaaatgccatatattcaaaaaagct
caaagataattttctttactattatgttcaaataatattcaatgcatattatctttaaaaagttaaatgtttttttaatcttcaagaaatcatgctacactt
aacttctcctagaagctaatctataccataatattttcatattcacaagatattaaattaccaattttcaaattattgttagtaaagaacaaaatgattctctc
ccaaagaaagacacattttaaatactccttcactctaaaactctggtattataacttttgaaagttaatatttctacatgaaatgtttagctcttacactctat
ccttcctagaaaatggtaattgagattactcagatattaattaaatacaatatcatatatatattcacagagtataaacctaaataatgatctattagattcaa
atatttgaaataaaaacttgattttttgtaaaaaaaaaaaaaaaaaaaa
```

"SAMD9L" refers to sterile alpha motif domain containing 9 like gene that produces a transcript comprising the polynucleotide sequence of NM_152703.4 (SEQ ID NO: 10). In the sequence, thymine (t) may be substituted for uracil (u).

SEQ ID NO: 10

```
gcttctcaactggcactctgacacaccctcagaaagtcagagtactgggagaacagaagacttcacaatttaatgcctcagttttttaaaaaaggatc
cttacacttcatgtctcctagccatcagaagaggaatgagacagcaaaagttcaaatggcctgtttcaagtttctgatataaaacgatgacatttttcag
gaaaatcctgcatttccagagagagactggctggttaaatttctgaaagaggacaccagctaaaagaaggtattgcatctcacccgagcagactgt
gtctgtggaaagtgtaagccccttgccagaagagcagcttcccagcaaaggcagagggtgaaaacagcaaaggtcttaagacactggggacct
agagtcaaaagggacctcctccagggaaaacgctgtgtgagaaatggcctcattcggtgactgtgagtgacacagcagaaagttgggtcattcc
ggctgctttttttgagaagtccctgaagagatcaataacagcaagagggaacctggcaaggaagctattcctataatccaggaaagagatgagga
aggcttggaccaggtggtagtggtgtcaggtagtcaaatgctgggtatattttgaagatacaccccataggatttgctccacattgaatgtggaatg
ctggaagagagataaagtgtacctgtcacatacttttttgagttttattattttcttagaagtaagtacacaaagagatgctacctaggagaagggtatt
cttttcactattcttttcaaattttctgtatgttcaaacattttcatagtagaaagttggggggaaaatctgtttcataaacattttcctcagcagcagtccagt
ctattgcatttttaattggttgtgatatcattgttttatgcaatacgttctcaacaagtatatcctccggcaaactgaacaaggaccaagtctgttctgccta
```

-continued

```
cagctctgcttcctcatagctgctttccagaacgtgactcttgcaaattatcaagaaagggaactaatctaagggatccagatcaaacagcctcat gaagacttattttatgtttctaatataaagatagaagttttcagaaaagccctgctacacagaggatcagagcagggtgggcctgctgggctgcag ctgggattctgagcatcctttcccggaggcacggaaagtgagtgagtgagcccagtgaggaagaagttgaagctttgatatgagtaaacaagtat ctctacctgaaatgattaaagactggaccaaagagcatgtgaaaaatgggtaaatgaagacctcaagattaatgagcaatacgggcaaattctgc tcagtgaagaagtaacaggattagtcctgcaggaattaactgagaaggaccttgtagaaatggggctaccatggggtccagcacttttgataaaac gttcatacaacaaattgaatagtaagtcccctgaaagtgacaatcatgatccgggacaattagataattcaaaaccgtccaaaacagaacaccaga aaaatccaaaacacaccaaaaggaagaagaaaattcaatgtcatctaatattgattatgatcccagagagatcagagatatcaaacaagaagaat caattcttatgaaagaaatgtgttagatgaagtagcaaatgctaaacacaagaaaaagggtaagctaaaacctgaacaattgacttgtatgccata tccttttgatcagttccatgacagccatcgctacatagaacattatactctacaacctgaaacaggagcactcaatctcattgatccaatacatgagtt caaagctctcacaaacacagaaacagccacggaagtggacattaagatgaaattcagcaatgaagtcttccgatttgcatcagcttgtatgaattca cgcaccaatggcaccatccattttggagtcaaggacaaacccatggagaaattgttggtgtgaaaatcaccagtaaggctgccttcattgaccac ttcaatgtaatgatcaaaaagtattttgaagaaagtgagatcaatgaagccaagaagtgtattcgggagccaaggtttgtggaagtccttctgcaga acaatacaccatctgacagatttgtcattgaagttgatactattccaaaacactctatatgtaatgataagtatttctacattcagatgcaaatttgtaaag ataaatatggaaacaaaaccaaaatcttttcactgtttgtaagagaaggggctagctctagggatatcctggccaattccaagcaacgggatgtag atttcaaggcattttttacaaaatttaaagtcactggtagcatctagaaaagaggctgaagaagagtatggaatgaaggcaatgaagaaggagagtg aaggactaaagctggttaaacttctcataggaaaccgagactcactggataattcatactatgactggtacattcttgtaacaaataaatgccatcca aaccaaataaagcacttagattttttaaaagaaattaaatggtttgctgtgttggagtttgatcctgaatctatgatcaatggagtggtcaaagcttaca aagaaagtcgggtggcaaaccttcactttccaaatcaatatgaagacaagacaactaacatgtgggagaagatttctactcttaatctttaccaaca gcccagctggattttctgcaacggcagatcagacctgaaaagcgagacatataaacctctagaaccacatttatggcagagagaaagagcttcag aagtcaggaaactaattttatttctcacagatgaaaatataatgacaagaggaaaattttttggtagtgtttctattactctcttcagtggaaagcccagg agatccactcattgaaactttctggctttctatcaagctctcaaaggaatggaaaatatgtgtgtatctctgtaaactcacatatttatcaacgatgga aagatctactacaaacaagaatgaagatggaagatgaactaacaaaccacagtatttccactttaaatatagaactggtaaacagcactatccttaa actaaaatcggtgactcggtcatcaagaaggttttgcccgcccgtggatcttcttcagttatcctagagaaaaagaaagaggatgtcttgactgca ctggaaatcctctgtgaaaatgagtgtacagagacagacatcgagaaagacaaatctaaattcctggagtttaagaaatcaaaagaagaacacttt tatcgaggtggcaaagtatcctggtggaacttctattttcttctgaaaactattcttcagattttgttaaaagggacagttatgaaaagcttaaagattta atacactgctgggcagagtctcctaaaccaatatttgcaaaaatcatcaatctttatcatcatccaggctgtggaggtaccacactggctatgcatgtt ctctgggacttaaagaaaaacttcagatgtgctgtgttaaaaaacaagacaactgattttgcagaaattgcagagcaagtgatcaatctggtcacct atagggcaaagagccatcaggattacattcctgtgcttctccttgtggatgattttgaagaacaagaaaatgtctactttctacaaaatgccatccattc cgttttagcagaaaaggatttgcgatatgaaaaaacattggtaattatcttaaactgcatgagatcccggaatccagatgaaagtgcaaaattggca gacagtattgcactaaattaccaactttcttccaaggaacaaagagcttttggtgccaaactgaaggaaattgaaaagcagcacaagaactgtgaa aacttttattccttcatgatcatgaaaagcaattttgatgaaacatatatagaaaatgtagtcaggaatatcctaaaaggacaggatgttgacagcaag gaagcacaactcatttccttcctggctttactcagctcttatgttactgactctacaatttcagtttcacagtgtgaaatattttgggaatcatatacacta gtacaccctgggaacctgaaagcttagaagacaagatgggaacttattctacacttctaataaaaacagaagttgcagaatatgggagatacaca ggtgtgcgtatcattcaccctctgattgccctgtactgtctaaaagaactggaagaagctatcacttggataaatgtcaaattgcattgaatatattag aagagaatttattctatgattctggaataggaagagacaaatttcaacatgatgttcaaactcttctgcttacaagacagcgcaaggtgtatggagat gaaacagacactctgttttccccattaatggaagctttacagaataaagacattgaaaaggtcttgagtgcaggaagtagacgattcccacaaaatg cattcatttgtcaagccttagcaagacatttctacattaaagagaaggactttaacacagctctggactgggcacgtcaggccaaaatgaaagcac ctaaaaattcctatatttcagatacactaggtcaagtctacaaaagtgaaatcaaatggtggttggatgggaacaaaaactgtaggagcattactgtt aatgacctaacacatctcctagaagctgcggaaaaagcctcaagagctttcaaagaatcccaaaggcaaactgatagtaaaaactatgaaaccga gaactggtcaccacagaagtcccagagacgatatgacatgtataacacagcttgttcttgggtgaaatagaagttggtctttacactatccagattc ttcagctcactccctttttccacaaagaaaatgaattatccaaaaaaacatatggtgcaattttttatcaggaaagtggaccattcctcctgatcccagaa
```

-continued

```
atgaatgttatttggctcttagcaagttcacatcccacctaaaaaatttacaatcagatctgaaaaggtgctttgacttttttattgattatatggttcttctg aaaatgaggtatacccaaaaagaaattgcagaaatcatgttaagcaagaaagtcagtcgttgtttcaggaaatacacagaactttttctgtcatttgga tccatgtctattacaaagtaaagagagtcaattactccaggaggagaattgcaggaaaaagctagaagctctgagagcagataggtttgctggact cttggaatatcttaatccaaactacaaagatgctaccaccatggaaagtatagtgaatgaatatgccttcctactgcagcaaaactcaaaaaagccc atgacaaatgagaaacaaaattccattttggccaacattattctgagttgtctaaagcccaactccaagttaattcaaccacttaccacgctaaaaaa caactccgagaggtcttgcaatttgtaggactaagtcatcaatatccaggtccttatttcttggcctgcctcctgttctggccagaaaatcaagagcta gatcaagattccaaactaatagaaaagtatgtttcatccttaaatagatccttcaggggacagtacaagcgcatgtgcaggtccaagcaggcaagc acactttctatctgggcaaaggaagggtctaaacagtattgttcacaaggccaaaatagagcagtactttgataaagcacaaaatacaaattccc tctggcacagtggggatgtgtggaaaaaaatgaagtcaaagacctcctgcgtcgtctaactggtcaggctgaaggcaagctaatctctgtagaa tatgaacagaggaaaaaataaaaataccagtaatatctgtttattcaggtccactcagaagtggtaggaacatagaaagagtgtctttctacctagg attttccattgaaggccctctggcatatgatatagaagtaatttaagacaatacatcacctgtagttcaaatacgtttatttatatctttatgattttattctc tctctctattctcatggcactttcataacattatggctaacctctaattacagattttgcttttgcctccctgaatgaattacaagccttttttaagatatgaaa tatgcctacccgcagagcttggcacaaagtggagtcaatcttttaatgttttaaatatgcattttcagactcaaataattaagaagtttcattgatatcca ctggtcacatcataactgtctatagggcaataaaatctgtgttaaactcaattgcttttataagttttctaaattatttcttcactgtgacagcaaagattta aataagatgaatgtaaaagagaaagcttattggactcaaacccacagatccacaccagagttctatttacctcatcttggtatcaataaaaacttatgt ggaaggtaaatatattgttccccatccaccacataacactctccccaacacacacacacacacacacacacacacacacacacacacacactcct tgtacccttgccttctcccagctcattgctccaggagagagaagagttcaaaaaataaagtaatcataaacttgaactctctccattctcttgttccc atttacaggtgaatctcttccttaagccattttttgtctcctgtgaatacagccttatctccacctgtttcttagatcccatctccctggcttattttttcca ttcattaccctctttgttccctttacttctcaacctgtgctatatacatgctgttctctctgttgagattgccttatttccatctaacattctctctcctgcta ttctgatttgtcattcacaactgatttcaagagtcaccttcaccaggaagtcttccttgaccaccatcattcctgcctgattagagggcttcctcatggtaatat gtgttctcaagttttcagtgtcaaggaatgccatcccagaagctcattctcagatgcacaacagccagaacagtctcaagcagcattctagagcttg gaatttaagaactacgcattgcctataaagtgaaacataggctaatatagattaaattgaatattgaataaaaaatatatttatttatccaca
```

The disclosure provides new means to detect type I interferon (IFN-I) signature utilizing POISE (Profile of Interferon Signature Expression) and methods and uses of POISE. The disclosure is based, at least in part, on the identification of a gene signature comprised of ten genes that can be used to differentiate between baseline and elevated IFN-I signature in a subject utilizing expression threshold values developed herein. The developed IFN-I signature can be utilized in a broad spectrum of applications, such as assessing IFN-I downstream activation, assessing therapeutic efficacy of administered IFN-I agonists or antagonists by evaluating baseline and post-administration IFN-I signature, identifying clinically asymptomatic subject with pre-onset or early onset disease based on elevated IFN-I signature, or methods of diagnosing and treating subjects having or suspected to have an elevated IFN-I signature.

The disclosure provides a solution to the challenge of reliably identifying patients having an elevated IFN-I signature, which may greatly increase the probability of success to achieve meaningful efficacy with an IFN-I inhibitor therapy while also minimizing exposure to patients that may not benefit from such a therapy. The disclosure also provides a solution to a challenge of early detection and identification of subjects who would benefit from IFN-I inhibitor therapy prior to onset of full clinical symptomology. The disclosure also provides a sensitive detection of IFN-I signature prior to the ability to directly detect IFN-I protein elevation, which may facilitate therapeutic and preventive interventions within early onset and pre-onset patients with IFN-I mediated disease.

Autoimmune and chronic inflammatory disorders involve abnormal immune response of the body targeting substances and tissues that are normally and/or chronically present in the body resulting in development of pathological symptoms. Examples of relatively common autoimmune and chronic inflammatory disorders include systemic lupus erythematosus (SLE), rheumatoid arthritis (RA), psoriatic arthritis (PA), and Sjögren's syndrome (SS).

It is widely believed that many autoimmune and chronic inflammatory disorders exhibit an onset that substantially precedes clinically-observable symptoms. Importantly, changes in biomarker profiles typically occur early in this cascade of events and thus may enable the detection of this progression before disease onset. For example, it has been reported that IFN-I is elevated in preclinical SLE (Lu et al., *J Autoimmun* 74:182-93, 2016).

Many autoimmune and chronic inflammatory disorders are characterized by an upregulation of IFN-I inducible transcripts, (i.e. IFN-I signature), however the degree and presence of IFN-I signature in patients is heterogenous. For example, approximately half of adult SLE patients exhibit an upregulation of IFN-I inducible transcripts in the blood and/or tissue (Baechler et al., *Proc Natl Acad Sci USA* 100:2610-15, 2003; Bennett et al., *J Exp Med* 197: 711-23, 2003; Dall'era et al., *Annals of the Rheumatic Diseases* 64:1692-97, 2005).

Many therapeutic agents are known to be efficacious for treating patients afflicted with autoimmune and chronic inflammatory disorders, and at least some of the therapeutic effects of those agents are believed to be attributable to the ability of the agents to decrease IFN-I production, or response to IFN-I. However, the therapeutic and IFN-I production-modulating effects of these agents have been observed mainly in patients who have already presented with clinical manifestations of autoimmune and chronic inflammatory disorders, including IFN-I overproduction.

For example, in a Phase 2 trial of moderate-to-severe SLE patients, anifrolumab (anti-IFN receptor chain 1 antibody) improved disease outcomes across multiple clinical endpoints (Furie et al., *Arthritis & Rheumatology* 69:376-86, 2017), however post hoc analysis of data from this trial indicated that efficacy responses were greater in patients with high baseline expression of IFN-I signature versus low signature.

Therefore, the ability to identify patients having an elevated IFN-I signature may greatly increase the probability of success to achieve meaningful efficacy with an IFN-I modulating therapy while also minimizing exposure to patients that may not benefit from such a therapy.

The disclosure provides a method of diagnosing and treating a subject having a type I interferon (IFN-I) mediated disease that is responsive to treatment with an IFN-I inhibitor, comprising:
 providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample;
 diagnosing the subject with the IFN-I mediated disease that is responsive to treatment with the IFN-I inhibitor when the combined expression value is equal to or higher than a threshold value; and
 administering the IFN-I inhibitor to the subject diagnosed as responsive to treatment with the IFN-I inhibitor.

The disclosure also provides a method of treating a subject suspected to have or having a type I interferon (IFN-I) mediated disease with an IFN-I inhibitor, comprising: determining that the subject has an elevated IFN-I signature by providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample;
 determining that the subject has the elevated IFN-I signature when the combined expression value is equal to or higher than a threshold value; and
 administering the IFN-I inhibitor to the subject determined to have the elevated IFN-I signature to treat the IFN-I mediated disease.

The disclosure also provides a method of detecting an elevated type I interferon (IFN-I) signature in a subject, comprising:
 providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample; and
 detecting the elevated IFN-I signature in the subject when the combined expression value is equal to or higher than a threshold value.

The disclosure also provides a method of detecting a baseline type I interferon (IFN-I) signature in a subject, comprising:
 providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample; and
 detecting the baseline IFN-I signature in the subject when the combined expression value is less than a threshold value.

The disclosure also provides a method of identifying a subject having elevated type I interferon (IFN-I) signature, comprising:
 providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample; and
 identifying the subject having elevated IFN-I signature when the combined expression value is equal to or higher than a threshold value.

The disclosure also provides a method of determining whether a subject having a type I interferon (IFN-I) mediated disease is responsive to treatment with an IFN-I inhibitor and deciding whether to treat the subject, comprising:
 providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample;
 diagnosing the subject with the IFN-I mediated disease as responsive to treatment with the IFN-I inhibitor when the combined expression value is equal to or higher than a threshold value or diagnosing the subject with the IFN-I mediated disease as non-responsive to treatment with the IFN-I inhibitor when the combined expression value is less than a threshold value; and
 administering the IFN-I inhibitor to the subject diagnosed as responsive to treatment with the IFN-I inhibitor or refraining from administering the IFN-I inhibitor to the subject diagnosed as non-responsive to treatment with the IFN-I inhibitor.

The disclosure also provides an in vitro method for predicting and/or diagnosing that a subject has an IFN-I mediated disease,
 providing a biological sample from the subject;
 assaying gene expression of genes DHX58, EIF2AK2, HERC5, IFI44, IFI44L, IFI6, IRF7, PARP9, PLSCR1 and SAMD9L in the biological sample;
 determining a combined expression value of the genes DHX58, EIF2AK2, HERC5, IFI44, IFI44L, IFI6, IRF7, PARP9, PLSCR1 and SAMD9L in the biological sample; and predicting and/or diagnosing that the subject has the IFN-I mediated disease when the combined expression value is equal to or higher than a threshold value.

The disclosure also provides a method of reducing placebo effect in a clinical trial, comprising
- providing a biological sample from a subject considered to be enrolled into a clinical trial;
- assaying gene expression of genes DHX58, EIF2AK2, HERC5, IFI44, IFI44L, IFI6, IRF7, PARP9, PLSCR1 and SAMD9L in the biological sample;
- determining a combined expression value of the genes DHX58, EIF2AK2, HERC5, IFI44, IFI44L, IFI6, IRF7, PARP9, PLSCR1 and SAMD9L in the biological sample; and
- enrolling the subject into the clinical trial when the combined expression value is equal to or higher than a threshold value and refraining to enroll the subject into the clinical trial when the combined expression value is less than the threshold value, thereby reducing the placebo effect In the clinical study described in the Examples no placebo response was observed. By not wishing to be bound by any particular theory, his observation suggests that SLE subjects with high IFN-I signature at baseline are less responsive to standard of care therapy which the placebo subjects continue to receive during the clinical trial. Thus, enriching for participants having elevated IFN-I signature at baseline may be a strategy to minimize placebo responses in SLE trials.

In some embodiments, the subject has an IFN-I mediated disease.

In some embodiments, the subject has a family history of the IFN-I mediated disease.

In some embodiments, the subject has one or more clinical symptoms of the IFN-I mediated disease but is ineligible for treatment with an IFN-I inhibitor.

In some embodiments, the subject has an autoimmune disease.

In some embodiments, the subject has cancer.

In some embodiments, the subject has been treated with a cancer therapeutic.

In some embodiments, the subject has an infectious disease.

In some embodiments, the subject has been treated with a drug against the infectious diseases.

The disclosure also provides a method of treating a subject suspected to have or having a type I interferon (IFN-I) mediated disease with an IFN-I inhibitor, comprising:
- determining that the subject has an elevated IFN-I signature by
  - providing a biological sample from the subject;
  - assaying gene expression of genes DHX58, EIF2AK2, HERC5, IFI44, IFI44L, IFI6, IRF7, PARP9, PLSCR1 and SAMD9L in the biological sample;
  - determining a combined expression value of the genes DHX58, EIF2AK2, HERC5, IFI44, IFI44L, IFI6, IRF7, PARP9, PLSCR1 and SAMD9L in the biological sample;
  - determining that the subject has the elevated IFN-I signature when the combined expression value is equal to or higher than a threshold value; and
- administering the IFN-I inhibitor to the subject determined to have the elevated IFN-I signature to treat the IFN-I mediated disease.

The disclosure also provides a method of diagnosing and treating a subject having a type I interferon (IFN-I) mediated disease that is responsive to treatment with an IFN-I inhibitor, comprising:
- providing a biological sample from a subject suspected to have or having a type I interferon (IFN-I) mediated disease;
- assaying gene expression of genes DHX58, EIF2AK2, HERC5, IFI44, IFI44L, IFI6, IRF7, PARP9, PLSCR1 and SAMD9L in the biological sample;
- determining a combined expression value of the genes DHX58, EIF2AK2, HERC5, IFI44, IFI44L, IFI6, IRF7, PARP9, PLSCR1 and SAMD9L in the biological sample;
- diagnosing the subject with the IFN-I mediated disease when the combined expression value is equal to or higher than a threshold value; and
- treating the subject suspected to have or having the IFN-I mediated disease by administering a therapeutically effective amount of an IFN-I inhibitor to the subject.

The disclosure also provides a method of predicting response of a subject having a type I interferon (IFN-I) mediated disease to treatment with an IFN-I inhibitor, comprising: providing a biological sample from the subject;
- assaying gene expression of genes DHX58, EIF2AK2, HERC5, IFI44, IFI44L, IFI6, IRF7, PARP9, PLSCR1 and SAMD9L in the biological sample;
- determining a combined expression value of the genes DHX58, EIF2AK2, HERC5, IFI44, IFI44L, IFI6, IRF7, PARP9, PLSCR1 and SAMD9L in the biological sample;
- predicting the subject as a responder when the combined expression value is equal to or higher than a threshold value and predicting the subject as a responder when the combined expression value is lower than the threshold value.

The disclosure also provides a method of treating a subject having a type I interferon (IFN-I) mediated disease that is responsive to treatment with an IFN-I inhibitor, comprising providing a biological sample from the subject;
- assaying gene expression of genes DHX58, EIF2AK2, HERC5, IFI44, IFI44L, IF16, IRF7, PARP9, PLSCR1 and SAMD9L in the biological sample;
- determining a combined expression value of the genes DHX58, EIF2AK2, HERC5, IFI44, IFI44L, IFI6, IRF7, PARP9, PLSCR1 and SAMD9L in the biological sample;
- treating the subject with the IFN-I inhibitor when the combined expression value is equal to or higher than a threshold value.

The disclosure also provides a method of determining whether a subject having a type I interferon (IFN-I) mediated disease is responsive to treatment with an IFN-I inhibitor and deciding whether to treat the subject, comprising:
- providing a biological sample from the subject;
- assaying gene expression of genes DHX58, EIF2AK2, HERC5, IFI44, IFI44L, IFI6, IRF7, PARP9, PLSCR1 and SAMD9L in the biological sample;
- determining a combined expression value of the genes DHX58, EIF2AK2, HERC5, IFI44, IFI44L, IFI6, IRF7, PARP9, PLSCR1 and SAMD9L in the biological sample;
- diagnosing the subject with the IFN-I mediated disease as responsive to treatment with the IFN-I inhibitor when the combined expression value is equal to or higher than a threshold value or diagnosing the subject with the IFN-I mediated disease as non-responsive to treatment with the IFN-I inhibitor when the combined expression value is less than a threshold value; and administering the IFN-I inhibitor to the subject diagnosed as responsive to treatment with the IFN-I inhibitor or refraining from administering the IFN-I inhibitor to the subject diagnosed as non-responsive to treatment with the IFN-I inhibitor.

The disclosure also provides a method of treating a subject with an IFN-I inhibitor, wherein the subject has a type I interferon (IFN-I) mediated disease that is responsive to treatment with an IFN-I inhibitor, the method comprising the steps of:

providing a biological sample from the subject;

assaying gene expression of genes DHX58, EIF2AK2, HERC5, IFI44, IFI44L, IFI6, IRF7, PARP9, PLSCR1 and SAMD9L in the biological sample;

determining a sum of normalized threshold cycle (CT) values (SUMΔCT) of genes DHX58, EIF2AK2, HERC5, IFI44, IFI44L, IFI6, IRF7, PARP9, PLSCR1 and SAMD9L;

a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{\wedge -ddCT}$)); and/or a POISE score calculated according to a formula I:
POISE Score=70−|43.7251664−SUMlog2($2^{\wedge -ddCT}$)| (Formula I); or any combination thereof;

treating the subject with the IFN-I mediated disease with the IFN-I inhibitor when SUMΔCT is equal to or higher than a threshold SUMΔCT value of 57.474, the SUMlog2($2^{\wedge -ddCT}$) value is equal to or higher than a threshold SUMlog2($2^{\wedge -ddCT}$) value of 8.725 or the POISE score is equal to or higher than a threshold POISE score of 35; or any combination thereof.

The disclosure also provides a method of predicting response of a subject having a type I interferon (IFN-I) mediated disease to treatment with an IFN-I inhibitor, comprising:

providing a biological sample from the subject;

assaying gene expression of genes DHX58, EIF2AK2, HERC5, IFI44, IFI44L, IFI6, IRF7, PARP9, PLSCR1 and SAMD9L in the biological sample;

determining a sum of normalized threshold cycle (CT) values (SUMΔCT) of genes DHX58, EIF2AK2, HERC5, IFI44, IFI44L, IFI6, IRF7, PARP9, PLSCR1 and SAMD9L;

a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{\wedge -ddCT}$)); and/or a POISE score calculated according to a formula I:
POISE Score=70−|43.7251664−SUMlog2($2^{\wedge -ddCT}$)| (Formula I); or any combination thereof;

predicting the subject as a responder when the SUMΔCT is equal to or higher than a threshold SUMΔCT value of 57.474, the SUMlog2($2^{\wedge -ddCT}$) value is equal to or higher than a threshold SUMlog2($2^{\wedge -ddCT}$) value of 8.725 or the POISE score is equal to or higher than a threshold POISE score of 35; or any combination thereof.

The disclosure also provides a method of treating a subject with an antagonistic antibody that binds Type I interferon comprising a heavy chain variable region 1 (HCDR1), a HCDR2, a HCDR3, a light chain variable region 1 (LCDR1), a LCDR2 and a LCDR3 of SEQ ID NOs: 11, 12, 13, 14, 15 and 16, respectively, such as a heavy chain variable region (VH) of SEQ ID NO: 17 and a light chain variable region (VL) of SEQ ID NO: 18, for example a heavy chain (HC) of SEQ ID NO: 19 and a light chain (LC) of SEQ ID NO: 20, wherein the subject has Type I interferon (IFN-I) mediated disease that is responsive to treatment with the antibody, the method comprising the steps of:

providing a biological sample from the subject;

assaying gene expression of genes DHX58, EIF2AK2, HERC5, IFI44, IFI44L, IFI6, IRF7, PARP9, PLSCR1 and SAMD9L in the biological sample;

determining a sum of normalized threshold cycle (CT) values (SUMΔCT) of genes DHX58, EIF2AK2, HERC5, IFI44, IFI44L, IFI6, IRF7, PARP9, PLSCR1 and SAMD9L;

a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{\wedge -ddCT}$)); and/or a POISE score calculated according to a formula I:
POISE Score=70−|43.7251664−SUMlog2($2^{\wedge -ddCT}$)| (Formula I); or any combination thereof;

treating the subject with the IFN-I mediated disease with the IFN-I inhibitor when SUMΔCT is equal to or higher than a threshold SUMΔCT value of 57.474, the SUMlog2($2^{\wedge -ddCT}$) value is equal to or higher than a threshold SUMlog2($2^{\wedge -ddCT}$) value of 8.725 or the POISE score is equal to or higher than a threshold POISE score of 35; or any combination thereof.

The disclosure also provides a method of predicting response of a subject having Type I interferon (INF-I) mediated disease to treatment with an antagonistic antibody that binds Type I interferon comprising a heavy chain variable region 1 (HCDR1), a HCDR2, a HCDR3, a light chain variable region 1 (LCDR1), a LCDR2 and a LCDR3 of SEQ ID NOs: 11, 12, 13, 14, 15 and 16, respectively, such as a heavy chain variable region (VH) of SEQ ID NO: 17 and a light chain variable region (VL) of SEQ ID NO: 18, for example a heavy chain (HC) of SEQ ID NO: 19 and a light chain (LC) of SEQ ID NO: 20, wherein the subject has IFN-I mediated disease that is responsive to treatment with the antibody, the method comprising the steps of:

providing a biological sample from the subject;

assaying gene expression of genes DHX58, EIF2AK2, HERC5, IFI44, IFI44L, IFI6, IRF7, PARP9, PLSCR1 and SAMD9L in the biological sample;

determining a sum of normalized threshold cycle (CT) values (SUMΔCT) of genes DHX58, EIF2AK2, HERC5, IFI44, IFI44L, IFI6, IRF7, PARP9, PLSCR1 and SAMD9L;

a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{\wedge -ddCT}$)); and/or a POISE score calculated according to a formula I:
POISE Score=70−|43.7251664−SUMlog2($2^{-ddCT}$)| (Formula I); or any combination thereof;
predicting the subject as a responder when the SUMΔCT is equal to or higher than a threshold SUMΔCT value of 57.474, the SUMlog2($2^{-ddCT}$) value is equal to or higher than a threshold SUMlog2($2^{-ddCT}$) value of 8.725 or the POISE score is equal to or higher than a threshold POISE score of 35; or any combination thereof.

In some embodiments, the methods of the disclosure comprise a step of normalizing gene expression of genes DHX58, EIF2AK2, HERC5, IFI44, IFI44L, IFI6, IRF7, PARP9, PLSCR1 and SAMD9L to the expression level of a control gene.

In some embodiments, the control gene is a housekeeping gene.

In some embodiments, the housekeeping gene is B2M, TFRC, YWHAZ, RPLO, 18S, GUSB, UBC, TBP, GAPDH, PPIA, POLR2A, ACTB, PGK1, HPRT1, IPO8 or HMBS.

In some embodiments, the housekeeping gene comprises ACTB, B2M and GAPDH.

In some embodiments, the combined expression value is a sum of normalized threshold cycle (CT) values (SUMΔCT) of genes DHX58, EIF2AK2, HERC5, IFI44, IFI44L, IFI6, IRF7, PARP9, PLSCR1 and SAMD9L.

In some embodiments, the threshold value is SUMΔCT of 57.474.

In some embodiments, the combined expression value is a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{-ddCT}$)).

In some embodiments, the threshold value is SUMlog2($2^{-ddCT}$) of 8.725.

In some embodiments, the combined expression value is a POISE Score of Formula I:

$$\text{POISE Score}=70-|43.7251664-\text{SUMlog2}(2^{-ddCT})| \quad \text{(Formula I)}$$

In some embodiments, the reference value is the POISE Score of between 30 and 40.

In some embodiments, the reference value is the POISE score of 35.

In some embodiments, the sensitivity and false positive rate of detecting the elevated IFN-I signature is about 90% about 15%, respectively.

In some embodiments, the sensitivity and false positive rate of detecting the elevated IFN-I signature is about 82% about 10%, respectively.

In some embodiments, the sensitivity and false positive rate of detecting the elevated IFN-I signature is about 98% about 30%, respectively.

The disclosure also provides a method of diagnosing and treating a subject with a type I interferon (IFN-I) mediated disease that is responsive to treatment with an IFN-I inhibitor, comprising:
providing a biological sample from the subject;
assaying gene expression of genes DHX58, EIF2AK2, HERC5, IFI44, IFI44L, IFI6, IRF7, PARP9, PLSCR1 and SAMD9L in the biological sample;
determining
a sum of normalized threshold cycle (CT) values (SUMΔCT) of genes DHX58, EIF2AK2, HERC5, IFI44, IFI44L, IFI6, IRF7, PARP9, PLSCR1 and SAMD9L;

a sum of log 2 fold changes of normalized differential expression between the biological sample and a biological sample obtained from one or more healthy controls of genes DHX58, EIF2AK2, HERC5, IFI44, IFI44L, IFI6, IRF7, PARP9, PLSCR1 and SAMD9L (SUMlog2($2^{-ddCT}$)); or
a POISE score calculated according to a formula I:
POISE Score=70−|43.7251664−SUMlog2($2^{-ddCT}$)| (Formula I); or any combination thereof;
diagnosing the subject with the IFN-I mediated disease that is responsive to treatment with the IFN-I inhibitor when SUMΔCT is equal to or higher than a threshold SUMΔCT value of 57.474, the SUMlog2($2^{-ddCT}$) value is equal to or higher than a threshold SUMlog2 ($2^{-ddCT}$) value of 8.725 or the POISE score is equal to or higher than a threshold POISE score of 35; or any combination thereof; and
administering the IFN-I inhibitor to the subject diagnosed as responsive to treatment with the IFN-I inhibitor.

In some embodiments, the biological sample is a blood sample or a tissue sample.

In some embodiments, gene expression is assayed using quantitative Polymerase Chain Reaction (qPCR) or microarray, or both.

In some embodiments, gene expression is measured at the mRNA level.

In some embodiments, gene expression is measured one ore more days after the subject has been administered the IFN-I inhibitor.

In some embodiments, gene expression is measured 2, 3, 4, 5, 6, 7, 8, 9, 10, 11, 12, 13 or 14 days after the subject has been administered the IFN-I inhibitor.

In some embodiments, gene expression is measured one or more days after the subject has been administered the IFN-I inhibitor for the first time.

In some embodiments, gene expression is measured 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more days after the subject has been administered the IFN-I inhibitor for the first time.

In some embodiments, the IFN-I mediated disease is SLE, type I diabetes, psoriasis, primary Sjögren's disease, systemic sclerosis, rheumatoid arthritis, transplant rejection, dermatomyositis, polymyositis, Aicardi-Goutières syndrome, Sting associated vasculopathy with onset in infancy (SAVI) or chronic atypical neutrophilic dermatosis with lipodystrophy and elevated temperature syndrome (CANDLE).

In some embodiments, the IFN-I mediated disease is SLE. In some embodiments, the IFN-I mediated disease is type I diabetes. In some embodiments, the IFN-I mediated disease is primary Sjögren's disease. In some embodiments, the IFN-I mediated disease is systemic sclerosis. In some embodiments, the IFN-I mediated disease is rheumatoid arthritis. In some embodiments, the IFN-I mediated disease is dermatomyositis. In some embodiments, the IFN-I mediated disease is polymyositis. In some embodiments, the IFN-I mediated disease is Aicardi-Goutières syndrome. In some embodiments, the IFN-I mediated disease is Sting associated vasculopathy with onset in infancy (SAVI). In some embodiments, the IFN-I mediated disease is chronic atypical neutrophilic dermatosis with lipodystrophy and elevated temperature syndrome (CANDLE).

In some embodiments, SLE is lupus nephritis, cutaneous lupus or lupus with central nervous system (CNS) manifestations.

In some embodiments, the IFN-I inhibitor is a molecule that blocks interaction of IFN-I with IFNAR, an antagonistic antibody that binds Type I interferon, an antagonistic antibody that binds IFNAR, an inhibitor of Tyk2, Jak1, TLR3, TLR7, TLR8, TLR9, STING a modulator or depletor of plasmacytoid dendritic cells; or an agent that degrades nucleic acids.

In some embodiments, the Type I interferon is IFN-α, IFN-β, IFN-ε, IFN-ω or IFN-κ.

In some embodiments, the modulator or depletor of plasmacytoid dendritic cells is an antibody that binds BDCA2, CD123 or ILT7/FcεRIγ complex.

In some embodiments, the anti-BDCA2 antibody is B11B059.

In some embodiments, the anti-CD123 antibody is SL-501, SL-101, IMGN-632, IM-23, CSL-362 (talacotuzumab) or SM-401.

In some embodiments, the anti-ILT7 antibody such as MED17734, In some embodiments, the agent that degrades nucleic acids is a recombinant nuclease.

In some embodiments, the antagonistic antibody that binds IFN-I comprises a heavy chain variable region 1 (HCDR1) of SEQ ID NO: 11, a HCDR2 of SEQ ID NO: 12, a HCDR3 of SEQ ID NO: 13, a light chain variable region 1 (LCDR1) of SEQ ID NO: 14, a LCDR2 comprising the amino acid sequence GAS and a LCDR3 of SEQ ID NO: 16;
- a heavy chain variable region (VH) of SEQ ID NO: 17 and a light chain variable region (VL) of SEQ ID NO: 18; or
- a heavy chain (HC) of SEQ ID NO: 19 and a light chain (LC) of SEQ ID NO: 20, or any combination thereof. GAS refers to the amino acids glycine, alanine and serine as is well-known.

In some embodiments, the antagonistic antibody that binds IFN-I is administered at a dose of about 10 mg/kg.

In some embodiments, the antagonistic antibody that binds IFN-I is administered at a dose of about 10 mg/kg once every two weeks.

In some embodiments, the antagonistic antibody that binds IFN-I is PF 06823859.

In some embodiments, the antagonistic antibody that binds IFN-I is AGS-009.

In some embodiments, the antagonistic antibody that binds IFN-I is rontalizumab.

In some embodiments, the antagonistic antibody that binds IFNAR comprises
- a heavy chain variable region 1 (HCDR1), a HCDR2, a HCDR3, a light chain variable region 1 (LCDR1), a LCDR2 and a LCDR3 of SEQ ID NOs: 21, 22, 23, 24, 25 and 26, respectively;
- a heavy chain variable region (VH) of SEQ ID NO: 27 and a light chain variable region (VL) of SEQ ID NO: 28; and/or
- a heavy chain (HC) of SEQ ID NO: 29 and a light chain (LC) of SEQ ID NO: 30. (anifrolumab).

```
HCDR1
                                        (SEQ ID NO: 11)
GYSFTSYW

HCDR2
                                        (SEQ ID NO: 12)
IDPSDSDT

HCDR3
                                        (SEQ ID NO: 13)
ARHPGLNWAPDFDY

LCDR1
                                        (SEQ ID NO: 14)
QSIDNSY

LCDR2
GAS

LCDR3
                                        (SEQ ID NO: 16)
QQGYDFPLT

SEQ ID NO: 17
EVQLVQSGAEVKKPGESLKISCKGSGYSFTSYWIGWVRQMPGKGLEWMGI

IDPSDSDTRYSPSFQGQVTISADKSISTAYLQWSSLKASDTAMYYCARHP

GLNWAPDFDYWGQGTLVTVSS

SEQ ID NO: 18
DIQMTQSPSSLSASVGDRVTITCRASQSIDNSYLNWYQQKPGKAPKLLIY

GASSLQSGVPSRFSGSGSGTDFTLTISSLQPEDFATYYCQQGYDFPLTFG

QGTKVEIK

SEQ ID NO: 19
EVQLVQSGAEVKKPGESLKISCKGSGYSFTSYWIGWVRQMPGKGLEWMGI

IDPSDSDTRYSPSFQGQVTISADKSISTAYLQWSSLKASDTAMYYCARHP

GLNWAPDFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 20
DIQMTQSPSSLSASVGDRVTITCRASQSIDNSYLNWYQQKPGKAPKLLIY

GASSLQSGVPSRFSGSGSGTDFTLTISSLQPEDFATYYCQQGYDFPLTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO: 21
NYWIA

SEQ ID NO: 22
IIYPGDSDIRYSPSFQG

SEQ ID NO: 23
HDIEGFDY

SEQ ID NO: 24
RASQSVSSSFFA

SEQ ID NO: 25
GASSRAT

SEQ ID NO: 26
QQYDSSAIT
```

-continued

SEQ ID NO: 27
EVQLVQSGAEVKKPGESLKISCKGSGYIFTNYWIAWVRQMPGKGLESMGI

IYPGDSDIRYSPSFQGQVTISADKSITTAYLQWSSLKASDTAMYYCARHD

IEGFDYWGRGTLVTVSS

SEQ ID NO: 28
EIVLTQSPGTLSLSPGERATLSCRASQSVSSSFFAWYQQKPGQAPRLLIY

GASSRATGIPDRLSGSGSGTDFTLTITRLEPEDFAVYYCQQYDSSAITFG

QGTRLEIK

SEQ ID NO: 29
EVQLVQSGAEVKKPGESLKISCKGSGYIFTNYWIAWVRQMPGKGLESMGI

IYPGDSDIRYSPSFQGQVTISADKSITTAYLQWSSLKASDTAMYYCARHD

IEGFDYWGRGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPEFEGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

SEQ ID NO: 30
EIVLTQSPGTLSLSPGERATLSCRASQSVSSSFFAWYQQKPGQAPRLLIY

GASSRATGIPDRLSGSGSGTDFTLTITRLEPEDFAVYYCQQYDSSAITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

In some embodiments, Tyk2 inhibitor is PF-06263276, SGI-1252, ARYY-111, UR-67767, TD-1473, PF-06826647, PF-06700841, PF-04965842, BMS-986165, SAR-20347, OST-246 or OST-122.

In some embodiments, Jak1 inhibitor is ATI-50001, LAS194046, TD-1473, ruxolitinib, BMT-1438, GLPG-0555, PF-04965842, Baricitinib, GSK-899, filgotinib maleate, INCB-47986, SGI-1252, ATI-50002, VR-588, tofacitinib, R-256, solcitinib, itacitinib, INCB-054707, tofacitinib, INCB-16562, SHR-0302, NIP-565, momelotinib, peficitinib, upadacitinib, CT-15300, BS-HH-002, SAR-20347, PF-06700841, PF-06263276, ABBV-599 or INCB-052793.

In some embodiments, TLR7 inhibitor is JB-6121, IMO-8400, IMO-9200, CPG-52364, IRS-954, DV-1079, DV-1179, E-6742 or E-6887.

In some embodiments, TLR8 inhibitor is JB-6121, VTX-763, IMO-8400, IMO-9200, CPG-52364, IMO-3100, E-6742 or E-6887.

In some embodiments, TLR9 inhibitor is E-6446, JB-6121, GNKS-356, IMO-9200, IMO-8400, CPG-52364, IMO-3100, IRS-954, DV-1079, DV-1179 or alicaforsen.

Type I IFN and IFN-I Signature

In humans, IFN-I is composed of 12 IFN-α protein subtypes and single functional proteins for IFN-β, IFN-α, IFN-κ, and IFN-ω. IFN-I induction occurs in response to both sterile and microbial ligands and this family of cytokines all signal through a ubiquitously expressed heterodimeric receptor (IFNAR) resulting in antiviral, antiproliferative and immunomodulatory effects. Thus, recombinant IFN-Is have been utilized in the clinic to treat both infectious and oncologic indications and more recently approaches to antagonize this pathway are in development for autoimmune indications. Exposure of cells to IFN-I induces the expression of hundreds of IFN-I inducible transcripts ultimately encoding gene products responsible for these pleotropic effects.

Given the broad diversity of transcripts induced by IFN-I several transcriptional signatures have been reported in the literature and have been utilized as a surrogate for direct detection of multiple IFN-I ligands. An exemplary IFN-I signature consisting of 21 upregulated genes is described in Yao et al, *Human Genomics and Proteomics: HGP* 2009. Other exemplary IFN-I signatures are described in Tcherepanova et al., *Annals of the Rheumatic Diseases* 71(Suppl3) (2012) and Richardson et al., *ACR/ARHP* 2012 *Annual Meeting Abstract* 620 (2012).

The identification of additional sets of IFN-I inducible transcripts and their application to sensitively quantify elevated IFN-I signature in human blood or tissue samples would enable an improvement in the current state of the art and enable a more precise approach to select for patients having a disease mediated by IFN-I and thus minimize exposure to agents modulating this pathway that may not have an IFN-I mediated disease as well as facilitate preventive interventions in pre-onset autoimmune subjects. This is of particular importance for autoimmune disease such as lupus where there is high unmet need and substantial heterogeneity as reflected by the long list of clinical trial failures seen in this disease.

The disclosure provides a novel IFN-I signature identified using human patient samples and machine learning and further describe its application to quantify IFN-I signature in human patient samples. The generated IFN-I signature was demonstrated to be more sensitive than direct detection of IFN-I protein in patient sera, thereby enabling identification of still asymptomatic or partially symptomatic subjects.

Methods of Measuring Gene Expression

Gene expression levels may be measured at the RNA level using known methods. Total RNA and/or mRNA may be isolated from a biological sample, such as blood using well-known methods.

Methods of analyzing gene expression are well-known and include methods based on hybridization of polynucleotides, methods based on sequencing of polynucleotides, and proteomics-based methods. mRNA expression in a sample may be quantified using northern blotting or in situ hybridization, RNAse protection assays, microarrays or PCR-based methods, such as reverse transcription polymerase chain reaction (RT-PCR) optionally followed by quantitative PCR (qPCR). RT-PCR step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The generated cDNA can then be used as a template in the subsequent qPCR reaction. In an exemplary method, total RNA is isolated from a blood sample of a subject using PAXgene Blood RNA tubes and RNA isolation kit from Qiagen, followed by reverse transcription into cDNA using commercial kits such as one from Qiagen. Gene expression profiling may be conducted using custom or off-the-shelf $RT^2$ Profiler PCR arrays commercially available from Qiagen, the arrays incorporating elements for RNA sample quality, data normalization and genomic DNA contamination detection.

To minimize errors and the effect of sample-to-sample variation, qPCR may be performed using an internal standard expressed at a constant level across various tissues. RNAs commonly used to normalize patterns of gene expression are mRNAs for one or more housekeeping genes, such as ACTB, B2M and GAPDH.

Data analyses of qPCR results may be based on the $\Delta CT$ or $\Delta\Delta CT$ methods, normalizing the raw data of a test gene in a test sample to the expression of one ore more housekeeping gene(s) within the test sample ($\Delta CT$) and/or comparing the normalized expression of the test gene in the test sample to the normalized expression of the same test gene in a control sample ($\Delta\Delta CT$). In some instances, level of gene expression may be expressed as fold change in a test sample vs. control sample (e.g. $2^{\wedge-\Delta\Delta CT}$), of alternatively, as log 2 fold changes (e.g. log $2(2^{\wedge-\Delta\Delta CT})$). In some instances, when expression levels of a combination of genes is analyzed, a sum of the various expression values may be analyzed (e.g. SUM$\Delta CT$; SUM$\Delta\Delta CT$; SUM$2^{\wedge-\Delta\Delta CT}$ and/or SUM log $2(2^{\wedge-ddCT})$).

Level of gene expression may also be analyzed using microarrays using commercially available platforms such as those from Affymetrix, Illumina and Agilent.

Generating Threshold Values

The disclosure described herein provides a new 10-gene set comprising genes DHX58, EIF2AK2, HERC5, IFI44, IFI44L, IFI6, IRF7, PARP9, PLSCR1 and SAMD9L that is capable of differentiating subjects having elevated IFN-I signature vs. subjects having baseline IFN-I signature with high accuracy. This combination of genes and threshold was empirically derived using machine learning methods and internal data sets to best classify healthy versus SLE subjects from a larger set of 84 IFN-I inducible genes described herein.

Threshold values utilizing the 10-gene signature may be developed by analyzing pooled biological samples obtained from healthy subjects having verified baseline IFN-I signature and subjects having verified elevated IFN-I signature for differential expression of the 10 genes. Threshold values may be then identified that stratify subjects to those having elevated IFN-I signature and those with baseline IFN-I signature.

Utilizing the methodologies described herein and in Example 1, a POISE (Profile of Interferon Signature Expression) Score threshold and a subject specific POISE score can be generated which can differentiate subjects having elevated IFN-I signature from those having baseline IFN-I signature using Formula I. POISE refers to a measurement of the expression levels of IFN-I response genes DHX58, EIF2AK2, HERC5, IFI44, IFI44L, IFI6, IRF7, PARP9, PLSCR1 and SAMD9L. POISE may be determined at baseline, i.e., prior to any treatment or at any time after administration of the treatment.

POISE Score(subject): 70−|43.725166641664−SUMlog2($2^{\wedge}-dd$CT)(subject)|;   Formula I:

wherein SUMlog2($2^{\wedge}$−ddCT) is a sum of log 2 fold changes of expression of the combination of the 10 genes in a biological sample from the subject when compared to the expression levels of the 10 genes in the control sample.

Subjects having a POISE Score of equal to or over 35 are identified as having an elevated IFN-I signature with about 90% sensitivity and a false positive rate of about 15%. Subjects having a POISE Score of equal to or over 30 are identified as having an elevated IFN-I signature with about 82% sensitivity and a false positive rate of about 20%. Subjects having a POISE Score of equal to or over 40 are identified as having an elevated IFN-I signature with about 98% sensitivity and a false positive rate of about 30%.

"Threshold POISE Score" refers to the POISE Score of between 30 and 40. In some embodiments, threshold POISE Score is 30. In some embodiments, threshold POISE Score is 35. In some embodiments, threshold POISE Score is 40.

With the identification of the threshold POISE Score, a threshold SUMlog2($2^{\wedge-ddCT}$)" value of 8.725 and a threshold SUM$\Delta CT$ value of 57.474 can be derived which correspond to the POISE Score of 35.

Treatment and Administration

Any subject identified to have an elevated IFN-I signature using the 10-gene signature developed herein may be treated with the IFN-I inhibitor as described herein. Such subjects include initially those suspected to have a IFN-I mediated disease and those diagnosed with the IFN-I mediated disease. Such disease includes SLE, including specific organ manifestations such as lupus nephritis, cutaneous lupus, and CNS manifestations, type I diabetes, psoriasis, primary Sjögren's disease, systemic sclerosis, rheumatoid arthritis, transplant rejection, dermatomyositis, polymyositis, Aicardi-Goutières syndrome, Sting associated vasculopathy with onset in infancy (SAVI) or chronic atypical neutrophilic dermatosis with lipodystrophy and elevated temperature syndrome (CANDLE).

For example, IFN-I signature has been reported to positively correlate with both clinical and serological features of lupus (Baechler et al., *Proc Natl Acad Sci USA* 100:2610-15, 2003; Bennett et al., *J Exp Med* 197:711-23, 2003; Dall'era et al., *Annals of the Rheumatic Diseases* 64:1692-97, 2005; Karageorgas et al., *J Biomed Biotechnol* 273907, 2011; Niewold et al., *Genes Immun* 8: 492-502, 2007).

The IFN-I inhibitor may be administered as a pharmaceutical composition containing a therapeutically effective amount of the IFN-I inhibitor and a pharmaceutically acceptable carrier. "Carrier" refers to a diluent, adjuvant, excipient, or vehicle with which the IFN-I inhibitor is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, P A 2006, Part 5, Pharmaceutical Manufacturing pp 691-1092, See especially pp. 958-989.

The mode of administration of the IFN-I inhibitor be any suitable route that delivers the antibody to a subject, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The IFN-I inhibitor may also be administered prophylactically in order to reduce the risk of developing a IFN-I mediated disease and/or delay the onset of the symptoms.

While having described the disclosure in general terms, the embodiments of the disclosure will be further disclosed in the following examples that should not be construed as limiting the scope of the claims.

Example 1 Generation of Profile of Interferon Signature Expression (POISE) and POISE Score POISE is a 10-gene quantitative PCR (qPCR) based method developed to quantify IFN-I signature in subjects. POISE score is a calculated value that differentiates subjects having elevated IFN-I signature and subjects having baseline IFN-I signature utilizing expression profiling information from blood samples of healthy donors and SLE patients.

Materials
A) SLE and healthy donor PAXgene Blood RNA tubes, (Provided by Temple University, Biological Specialty Corporation, Bioserve Biotechnologies, and Bioreclamation all under informed consent)
B) PAXgene Blood RNA kit (QIAGEN, Cat #762164)
C) RT$^2$ First Strand kit (QIAGEN, Cat #330404)
D) Custom RT$^2$RNA PCR Array (QIAGEN, Cat #CAPH13527)
E) RT$^2$ Sybr® Green qPCR Mastermix (QIAGEN, Cat #330529)

Methods and Results
Design and Validation of RT$^2$ qPCR Array 84 interferon-inducible genes and eleven controls per array were initially selected and printed onto a 96×4 format RT$^2$ qPCR array. The IFN-inducible genes were either known IFN-inducible transcripts (Yao, et al. *Human genomics and proteomics: HGP* 2009; 2009) or transcripts which were identified through internal RNA-Seq analysis of SLE donor blood samples.

A pooled healthy control total RNA sample was generated to standardize normalization of healthy versus each individual SLE sample to enable the establishment of a quantitative threshold for IFN-I dysregulation relative to healthy subjects. Healthy donor PAXgene blood RNA tubes were purchased from Biological Specialty Corporation and Bioserve. RNA was extracted using the PAXgene Blood RNA kit (QIAGEN) according to manufacturer's instructions. RNA yields of each sample were determined using a QIAxpert instrument (QIAGEN). 25 of the healthy PAXgene samples obtained had sufficient yield to begin reverse transcription into cDNA starting from 200 ng of total RNA from each sample. cDNA synthesis was performed using the RT$^2$ First Strand kit (QIAGEN) and then added to the RT$^2$ Sybr® Green qPCR Mastermix (QIAGEN) according to manufacturer's instructions. As a positive control, several SLE donor PAXgene tubes (29 total donors) were processed the same way. Samples were loaded onto custom qPCR arrays and qPCR data was obtained using the Viia™ 7 Real-Time PCR Instrument (Thermo Fisher Scientific). After instrument run completion, data was exported into Excel for analysis. To calculate the relative gene expression (ΔΔCT) changes amongst each of the samples, the following formulas were utilized:

1) Formula 1=CT Target gene−average CT of endogenous controls=Value A (endogenous controls included housekeeping genes ACTB, GAPDH, and B2M)
2) Formula 2=mean of Value A's from untreated (or healthy donor) control group=Mean Value A
3) Formula 3=Value A SLE donor−Mean Value A control group=ΔΔCT
4) Formula 4=2^−ΔΔCT=Fold Change To determine what extent the healthy cohort showed baseline expression of IFN-inducible genes, samples from healthy donors were evaluated using a 21-gene IFN-I signature which included genes IFI27, IFI6, RSAD2, IFI44, IFI44L, USP18, LY6E, OAS1, SIGLEC1, ISG15, IFIT1, OAS3, HERC5, MX1, LAMP3, EPSTI1, IFIT3, OAS2, RTP4, PLSCR1, and DNAPTP6 (Yao, et al. *Human genomics and proteomics: HGP* 2009; 2009). The mean fold change of all 21 genes across each individual healthy donor versus the mean of the healthy group overall was 1.36. In contrast, the mean of the SLE donors versus the mean of the healthy group overall was 18.29 (FIG. 1A). As the baseline IFN-I signature across healthy donors varies slightly, the population was to be considered "baseline" signature when the mean fold change across the entire population was equal or less than 1.5.

Because there was little variability overall within the healthy cohort examined, all 25 donors were selected for creating the pooled healthy RNA preparation to be used as a normalization control on each of the custom qPCR arrays. To create this pooled preparation, 600 ng of each healthy donor's total RNA was combined into a single tube and frozen. 20 additional healthy donor PAXgene tubes were also evaluated for IFN-I signature to expand the pooled healthy RNA pool. There was a high correlation ($R^2$=0.9797; p<0.0001) between the 21-gene panel IFN inducible gene expression between the additional and original donors and hence all healthy donor samples were pooled and stored at −80° C.

29 PAXgene tubes from SLE donors were obtained for evaluation of expression profiles of the selected 84 IFN-inducible genes. All sample processing methods were followed identically to that described above except that the instrument used to generate the data was the 7900HT Real-Time PCR system (Applied Biosystems). On each qPCR array, the first position was designated for the pooled healthy control sample, while the remaining 3 positions were for SLE samples. Data were analyzed and each SLE sample's fold change over the healthy control was assessed to understand the heterogeneity in gene expression in subjects with SLE.

Figure 1B:
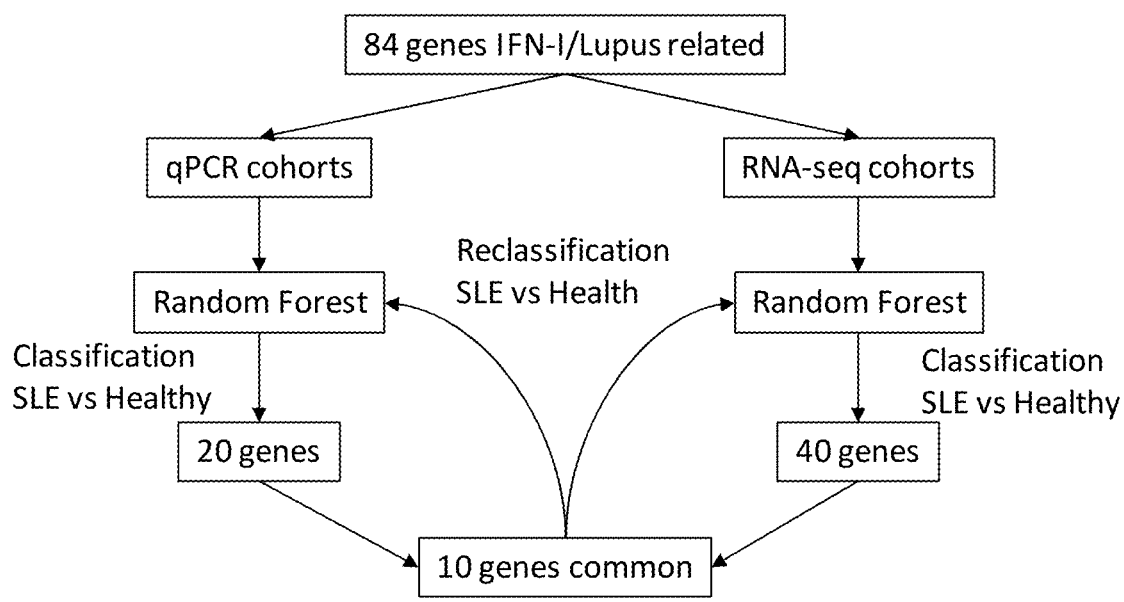
FIG. 1B shows the process of identifying a 10-gene set (POISE) used for assessing Type I interferon (IFN-I) signature expression.

Using a machine learning approach on the qPCR dataset, a Random Forest (RF) classifier was designed to distinguish SLE versus healthy donor gene expression. The classifier was run on the qPCR ΔΔCT (log 2 of fold change) data table in a 10×5-fold cross-validation setting as previously described (Zhang et al., *Genome Biol.* 2015, 16:14). Genes were ranked by their RF significance, expressed by the Gini index. The Matthews Correlation Coefficient (MCC) (Baldi et al., Assessing *Bioinformatics* 16:412-24, 2000) was used for performance assessment. A model build on the 20 top-ranked genes (qPCR-20) achieved a MCC=0.76. Next, an independent training data set from a separate RNA-Seq study was used to validate these results. This step was performed to identify the most robust set of transcripts agnostic of the gene expression platform utilized which would increase the utility of this assay. These data were converted to fold change to match the qPCR data. Using this dataset, the 84 genes contained on the qPCR array were evaluated using an RF classifier on the data set in a 10×5-fold CV setting enabling another model to be built which contained 40 genes ranked at highest significance (RNASEQ-40). After running the performance assessment, the achieved MCC value was 0.70. After comparing the qPCR-20 versus the RNA-Seq 40 gene lists, 10 IFN-inducible genes were identified in common: DHX58, EIF2AK2, HERC5, IFI44, IFI44L, IFI6, IRF7, PARP9, PLSCR1, and SAMD9L. To confirm the accuracy of these 10 genes to correctly classify SLE versus healthy donors, random forest analysis was repeated using only these 10 genes and once again, this gene list could distinguish healthy vs SLE donors with similar accuracy (MCC=0.76). The 10 genes were hence selected for subsequent analyses to assess IFN-I signature status in subjects moving forward (e.g. POISE). FIG. 1B shows the outline of the process of identifying the 10 genes for IFN-I signature.

POISE Score Derivation

Determining Threshold POISE Score and Threshold Log $2(2^{\wedge-ddCT})$ Values

The log 2 fold changes of differential expression (e.g. log $2(2^{\wedge}-\Delta\Delta CT)$) for each SLE donor (n=29) vs. the healthy donor pool were determined across the 10 selected genes. The highest fold change for each of the genes across all donors was identified. The sum of the highest log 2 fold changes for each of the 10 genes across all 29 SLE donors was then calculated [sum(GenesFC_SLE_Best)]. This score was designated as "SLE_Best" and was calculated to be 43.7251664. In other words, the value represented a hypothetical "best case scenario" of an SLE subject with an elevated IFN-I signature. This number was then used as the benchmark IFN-I signature for SLE subject comparison. To this end, each unknown SLE sample to be scored was treated similarly in that the sum of the log 2 fold changes (e.g. log $2(2^{\wedge-ddCT})$) of the same 10 genes was calculated [sum(GenesFC_SLE)] to generate a secondary "SLE subject-specific" score. Next, the absolute value of the distance between the benchmark "SLE_Best" score and the "SLE subject-specific" score was determined. This value was a precursor value of the POISE score. To make the POISE score value more intuitive aka higher score=higher IFN-I signature, the precursor value of the POISE score was subtracted from a score of 70 (which equals to twice the threshold POISE Score of 35 determined below) to generate the POISE score.

POISE Score=70−|sum(GenesFC_SLE_best)−sum(GenesFC_SLE)|;

The subject specific POISE Score can thus be calculated as:

POISE Score(subject)=70−|43.7251664−SUMlog2$(2^{\wedge-ddCT})$(subject)|

POISE score calculation also allows for the possibility of encountering an SLE subject with an even greater elevated IFN-I signature than that determined as "SLE_Best". In this scenario, the sum of the fold changes from the individual SLE subject would be greater than the "SLE_Best" resulting in a negative inverse POISE score value. When this negative value is subtracted from 70, the resulting POISE score would be a value even greater than 70 and therefore also above the threshold POISE Score of 35.

Figure 2:
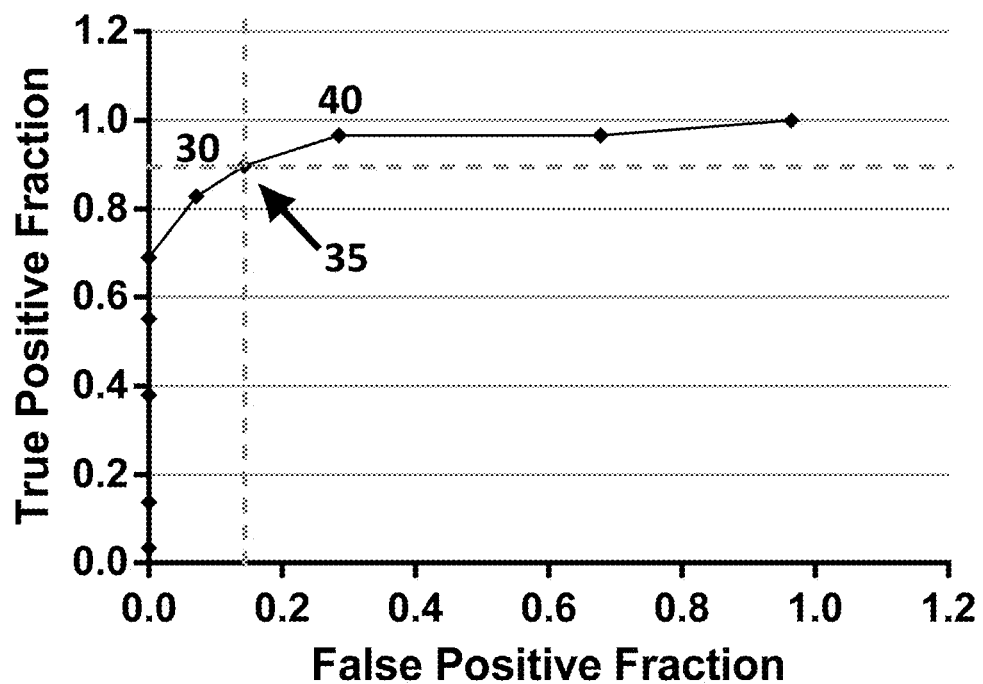
FIG. 2 shows a curve of simulation correlating the POISE score to false positive and true positive IFN-I signature samples. POISE score of 35 (arrow) correlated to 90% true positive.

To identify a threshold POISE Score to classify a subject as having an elevated IFN-I signature a simulation with different cutoffs was performed and the fraction of False Positives and the fraction of True Positives (sensitivity) were calculated for each cutoff. From this analysis, a threshold POISE Score of 35 was chosen as an appropriate threshold value to classify subjects (FIG. 2) because it was the threshold at which true IFN-I signature positive subjects could be identified accurately approximately 90% of the time and the false positive rate was about 15%.

Other threshold POISE Scores could also be used with alternative sensitivity and false positive values:

Threshold POISE Score of 30: Utilizing the threshold the false positive rate dropped to 10% and the true positive rate decreased to about 82% indicating that in about 20% of assessments, subjects with an elevated IFN-I signature were misclassified as having baseline IFN-I signature.

Threshold POISE Score of 40: Utilizing this threshold the false positive rate increased to about 30% and the true positive rate increased to about 98%.

To this end, a cutoff of 35 was determined to be the best compromise between the false and true positive fractions.

Threshold POISE Score of 35 or greater would require a minimum sum of log 2 fold change SUMlog2$(2^{\wedge-ddCT})$ for all 10 genes to be greater than or equal to 8.725. Subjects having SUMlog2$(2^{\wedge-ddCT})$ under 8.725 would be considered to have baseline IFN-I signature.

Calculating POISE Score and Threshold Expression Values without Normalizing to Healthy Donor Control Sample(s)

Initial inclusion of healthy donor scores enabled the determination of a threshold cutoff distinguishing IFN-I signature levels in healthy subjects versus SLE subjects. To eliminate the need for inclusion of a benchmark pooled healthy control sample a methodology was developed to derive the POISE Score a without normalizing gene expression to the healthy donor pool.

To accomplish this, gene expression of the 10 selected genes was normalized to the expression level of the three housekeeping genes within each analyzed sample for which sample specific POISE Score was available. For each sample, the average expression level of the three housekeeping genes (ACTB, GAPDH, and B2M) was subtracted from the expression level of each of the 10 genes in the same sample, after which the sum of the normalized expression for each of the 10 genes was calculated (nSum)

nSum=SUM(Genes−Average(Housekeeping genes))

nSum=SUM(CT(genes)−Average CT(housekeeping genes)=SUMΔCT

Sample specific POISE Scores were then correlated with the obtained sample specific nSum values (e.g. SUMΔCT) and a formula was extrapolated that facilitated conversion of SUMΔCT into the POISE Score. To obtain the POISE Score, the following formula was applied:

$Y=X-27.474$; wherein

Figure 3:
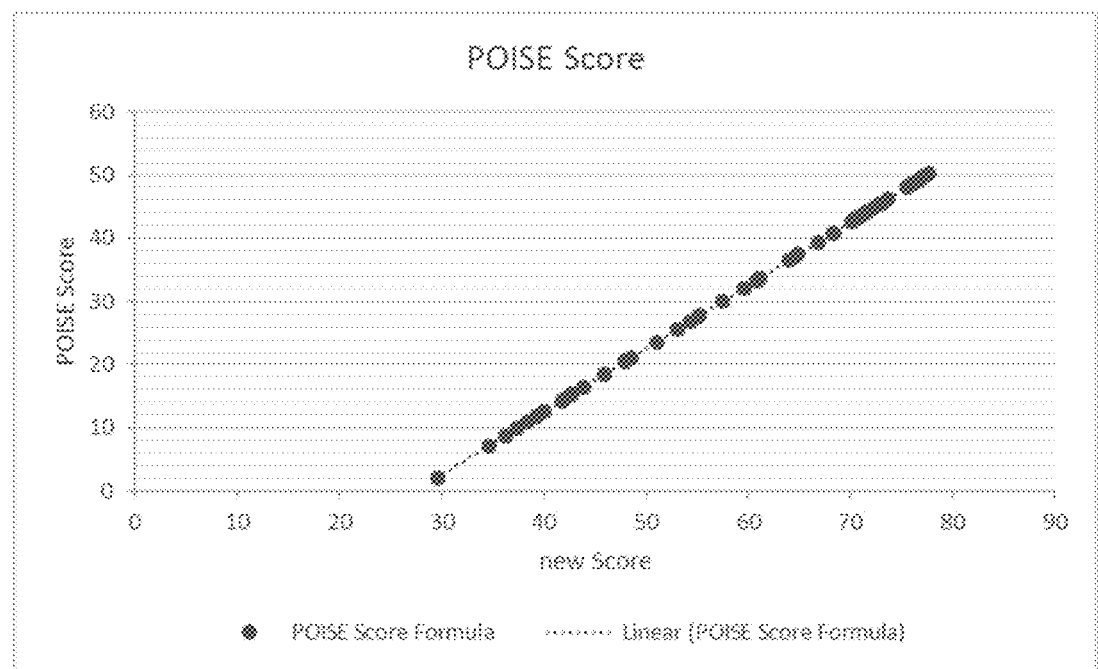
FIG. 3 shows the correlation between subject specific POISE Score and subject specific SUMΔCT.

Y is the POISE Score and X is nSum (e.g. SUMΔCT) FIG. 3 shows the correlation of the subject specific POISE Score and subject specific SUMΔCT.

A threshold SUMΔCT of 57.474 was determined to correlate with the threshold POISE Score of 35, i.e. subjects with SUMΔCT of 57.474 or more can be identified as having elevated IFN-I signature.

Example 2. A Phase 1, Randomized, Double-Blind, Placebo-Controlled, Single Ascending Dose Study in Healthy Subjects and Multiple Dose Study of JNJ-55920839 in Subjects with Mild to Moderate Systemic Lupus Erythematosus (NCT02609789)

JNJ-55920839 is a monoclonal antibody (mAb) targeting type I interferons (IFN-I). JNJ-55920839 broadly binds and neutralizes 11 of the 12 human interferon alpha (IFN-α) subtypes and human interferon omega (IFN-ω) with high affinity, but does not neutralize interferon beta (IFN-0) or IFN-α subtype D/1.

The primary objectives of this study are to assess the safety and tolerability of JNJ-55920839 following single ascending IV or subcutaneous administration in healthy subjects (Part A) and assess the safety and tolerability of JNJ-55920839 following multiple IV dose administrations in subjects with mild to moderate SLE (Part B).

Secondary Objectives of the study are to assess the pharmacokinetics (PK) and immunogenicity of JNJ-55920839 following ascending IV or subcutaneous administration in healthy subjects (Part A), and following multiple IV dose administrations in subjects with mild to moderate SLE (Part B), to evaluate pharmacodynamic (PD) effects and clinical responses following a IV or SC dose of JNJ-55920839 in healthy subjects (Part A), and evaluate PD and clinical response following multiple IV doses of JNJ-55920839 in subjects with mild to moderate SLE (Part B).

Exploratory Objectives are to evaluate biomarkers following a single IV or SC dose of JNJ-55920839 in healthy subjects (Part A), and following multiple IV doses of JNJ-55920839 in subjects with mild to moderate SLE (Part B), to evaluate the level of dysregulation of interferon signaling and how this dysregulation correlates with changes in other biomarkers and clinical response measures to administration of study agent, to explore the variability of interferon signatures across different racial/ethnic populations and its potential impact on clinical response associated with exposure to study agent and to explore PK/PD relationships of JNJ-55920839 through analysis of biomarkers, PD markers, and clinical response.

Inclusion and exclusion criteria for subjects with SLE can be found at ClinicalTrials website, as service for the U.S. National institutes of Health, under trial NCT02609789. Among other requirements, subjects eligible for enrollment in this study must have an elevated IFN-I signature as assessed by the POISE Score during screening (prior to randomization).

All subjects will be dosed based on their Day-1 body weight. In Part A, single ascending IV doses ranging from 0.3 to 15.0 mg/kg of JNJ-55920839 or placebo will be administered to sequential cohorts of healthy subjects as an IV infusion of at least 30 minutes. The infusion duration may be increased to approximately 60 minutes if issues of tolerability are encountered in prior cohorts. One additional cohort will receive a single 1 mg/kg SC administration of JNJ-55920839 or placebo. In Part B, 6 doses of up to 10 mg/kg JNJ-55920839 or placebo will be administered every 2 weeks as an IV infusion of at least 30 minutes. Based on the safety information observed in Part A, a dose lower than the planned 10 mg/kg dose may be selected in Part B.

Sterile 0.9% Saline for Injection, USP will be used for dilution of study agent and will also serve as placebo.

Subject Eligibility

Subject eligibility to the study was assessed in part by determining elevated IFN-I signature using the POISE score.

Two PAXgene tubes per subject were collected and one tube was sent to a centralized service core for analyses. RNA extraction was conducted utilizing QIAGEN PAXgene blood RNA extraction kit per manufacturer's instructions. RNA samples with >25 μg/ml, 260/280 ratio >1.8 and lack of degradation observed using Agilent® 2200 Tapestation using a RNA ScreenTape or Agilent® 2100 Bioanalyzer using an RNA 6000 Nano-Chip were proceeded to expression analysis using RT2 Prolifer PCR array (Qiagen) according to manufacturer's instruction using 200 ng of total RNA as starting material. The samples were amplified usingViiA 7 Real-Time PCR System (Thermo Fisher Scientific). Expression of DHX58, EIF2AK2, HERC5, IFI44, IFI44L, IFI6, IRF7, PARP9, PLSCR1, and SAMD9L and housekeeping genes ACTB, GAPDH and B2M genes were assessed. The POISE Score was calculated as described in Example 1.

Table 1 and Table 2 show the results of the $RT^2$ Prolifer PCR array showing ΔCT (target−mean endogenous control), ΔΔCT ((ΔCT of diseased sample vs ΔCT healthy control)), $2^{-\Delta\Delta CT}$ (expression fold change) and log 2 ($2^{-\Delta\Delta CT}$) (log 2 of expression fold change) values for the pool of health controls and five subjects seeking enrollment to the clinical trial. The sum of log 2 ($2^{-\Delta\Delta CT}$) for the 10 tested genes, calculated POISE score and inverse POISE score are shown in Table 3.

TABLE 1

| Sample Name | Gene | CT | ΔCT | ΔΔCT | $2^{-\Delta\Delta CT}$ | $\log2(2^{-\Delta\Delta CT})$ |
|---|---|---|---|---|---|---|
| Healthy Control* | ACTB | 18.65 | | | | |
| Subject 1** | ACTB | 19.75 | | | | |
| Subject 2*** | ACTB | 18.01 | | | | |
| Healthy Control | B2M | 19.84 | | | | |
| Subject 1 | B2M | 20.02 | | | | |
| Subject 2 | B2M | 19.13 | | | | |
| Healthy Control | GAPDH | 23.72 | | | | |
| Subject 1 | GAPDH | 24.21 | | | | |
| Subject 2 | GAPDH | 22.99 | | | | |
| Healthy Control | DHX58 | 29.57 | 8.84 | 0.00 | 1.00 | 0.00 |
| Subject 1 | DHX58 | 28.37 | 7.04 | −1.80 | 3.49 | 1.80 |
| Subject 2 | DHX58 | 29.78 | 9.73 | 0.89 | 0.54 | −0.89 |
| Healthy Control | EIF2AK2 | 26.71 | 5.97 | 0.00 | 1.00 | 0.00 |
| Subject 1 | EIF2AK2 | 24.82 | 3.49 | −2.49 | 5.61 | 2.49 |
| Subject 2 | EIF2AK2 | 25.48 | 5.44 | −0.54 | 1.45 | 0.54 |
| Healthy Control | HERC5 | 28.68 | 7.95 | 0.00 | 1.00 | 0.00 |
| Subject 1 | HERC5 | 26.08 | 4.75 | −3.19 | 9.14 | 3.19 |
| Subject 2 | HERC5 | 28.07 | 8.02 | 0.08 | 0.95 | −0.08 |
| Healthy Control | IFI44 | 27.07 | 6.34 | 0.00 | 1.00 | 0.00 |
| Subject 1 | IFI44 | 23.14 | 1.81 | −4.53 | 23.07 | 4.53 |
| Subject 2 | IFI44 | 27.21 | 7.17 | 0.83 | 0.56 | −0.83 |
| Healthy Control | IFI44L | 29.25 | 8.51 | 0.00 | 1.00 | 0.00 |
| Subject 1 | IFI44L | 23.74 | 2.41 | −6.10 | 68.67 | 6.10 |
| Subject 2 | IFI44L | 29.56 | 9.52 | 1.01 | 0.50 | −1.01 |

TABLE 1-continued

| Sample Name | Gene | CT | ΔCT | ΔΔCT | $2^{\sim\Delta\Delta CT}$ | $\log 2(2^{\sim\Delta\Delta CT})$ |
|---|---|---|---|---|---|---|
| Healthy Control | IFI6 | 26.78 | 6.05 | 0.00 | 1.00 | 0.00 |
| Subject 1 | IFI6 | 24.07 | 2.74 | −3.31 | 9.92 | 3.31 |
| Subject 2 | IFI6 | 26.00 | 5.96 | −0.09 | 1.06 | 0.09 |
| Healthy Control | IRF7 | 29.96 | 9.23 | 0.00 | 1.00 | 0.00 |
| Subject 1 | IRF7 | 29.00 | 7.67 | −1.56 | 2.95 | 1.56 |
| Subject 2 | IRF7 | 29.35 | 9.30 | 0.08 | 0.95 | −0.08 |
| Healthy Control | PARP9 | 25.52 | 4.79 | 0.00 | 1.00 | 0.00 |
| Subject 1 | PARP9 | 24.42 | 3.09 | −1.69 | 3.24 | 1.69 |
| Subject 2 | PARP9 | 24.12 | 4.08 | −0.71 | 1.64 | 0.71 |
| Healthy Control | PLSCR1 | 25.89 | 5.16 | 0.00 | 1.00 | 0.00 |
| Subject 1 | PLSCR1 | 24.08 | 2.76 | −2.40 | 5.29 | 2.40 |
| Subject 2 | PLSCR1 | 24.15 | 4.11 | −1.05 | 2.07 | 1.05 |
| Healthy Control | SAMD9L | 27.35 | 6.62 | 0.00 | 1.00 | 0.00 |
| Subject 1 | SAMD9L | 24.75 | 3.43 | −3.19 | 9.16 | 3.19 |
| Subject 2 | SAMD9L | 26.27 | 6.22 | −0.40 | 1.32 | 0.40 |

*mean CT of housekeeping genes: 20.74
**Mean CT of housekeeping genes: 21.33
***Mean CT of housekeeping genes: 20.04

TABLE 2

| Sample Name | Target Name | CT | ΔCT | ΔΔCT | $2^{\sim\Delta\Delta CT}$ | $\log 2(2^{\sim\Delta\Delta CT})$ |
|---|---|---|---|---|---|---|
| Healthy Control | ACTB | 18.43 | | | | |
| Subject 3 | ACTB | 17.14 | | | | |
| Subject 4 | ACTB | 17.04 | | | | |
| Subject 5 | ACTB | 17.73 | | | | |
| Healthy Control | B2M | 19.76 | | | | |
| Subject 3 | B2M | 18.61 | | | | |
| Subject 4 | B2M | 18.42 | | | | |
| Subject 5 | B2M | 20.13 | | | | |
| Healthy Control | GAPDH | 23.73 | | | | |
| Subject 3 | GAPDH | 22.41 | | | | |
| Subject 4 | GAPDH | 22.09 | | | | |
| Subject 5 | GAPDH | 22.97 | | | | |
| Healthy Control | DHX58 | 29.22 | 8.58 | 0.00 | 1.00 | 0.00 |
| Subject 3 | DHX58 | 28.95 | 9.56 | 0.98 | 0.51 | −0.98 |
| Subject 4 | DHX58 | 26.15 | 6.96 | −1.62 | 3.07 | 1.62 |
| Subject 5 | DHX58 | 29.13 | 8.85 | 0.28 | 0.83 | −0.28 |
| Healthy Control | EIF2AK2 | 26.58 | 5.93 | 0.00 | 1.00 | 0.00 |
| Subject 3 | EIF2AK2 | 25.44 | 6.06 | 0.12 | 0.92 | −0.12 |
| Subject 4 | EIF2AK2 | 23.28 | 4.09 | −1.84 | 3.58 | 1.84 |
| Subject 5 | EIF2AK2 | 26.98 | 6.70 | 0.77 | 0.59 | −0.77 |
| Healthy Control | HERC5 | 28.43 | 7.79 | 0.00 | 1.00 | 0.0) |
| Subject 3 | HERC5 | 27.88 | 8.49 | 0.70 | 0.62 | −0.70 |
| Subject 4 | HERC5 | 23.94 | 4.76 | −3.03 | 8.18 | 3.03 |
| Subject 5 | HERC5 | 28.95 | 8.67 | 0.88 | 0.54 | −0.88 |
| Healthy Control | IFI44 | 26.98 | 6.34 | 0.00 | 1.00 | 0.00 |
| Subject 3 | IFI44 | 26.65 | 7.27 | 0.92 | 0.53 | −0.92 |
| Subject 4 | IFI44 | 21.75 | 2.57 | −3.77 | 13.66 | 3.77 |
| Subject 5 | IFI44 | 27.22 | 6.95 | 0.60 | 0.66 | −0.60 |
| Healthy Control | IFI44L | 28.68 | 8.04 | 0.00 | 1.00 | 0.00 |
| Subject 3 | IFI44L | 30.18 | 10.79 | 2.75 | 0.15 | −2.75 |
| Subject 4 | IFI44L | 23.10 | 3.91 | −4.12 | 17.43 | 4.12 |
| Subject 5 | IFI44L | 30.14 | 9.87 | 1.83 | 0.28 | −1.83 |
| Healthy Control | IFI6 | 26.51 | 5.87 | 0.00 | 1.00 | 0.00 |
| Subject 3 | IFI6 | 26.40 | 7.01 | 1.15 | 0.45 | −1.15 |
| Subject 4 | IFI6 | 22.19 | 3.01 | −2.86 | 7.27 | 2.86 |
| Subject 5 | IFI6 | 27.31 | 7.03 | 1.17 | 0.45 | −1.17 |
| Healthy Control | IRF7 | 30.06 | 9.42 | 0.00 | 1.00 | 0.00 |
| Subject 3 | IRF7 | 29.26 | 9.87 | 0.45 | 0.73 | −0.45 |
| Subject 4 | IRF7 | 27.08 | 7.89 | −1.53 | 2.89 | 1.53 |
| Subject 5 | IRF7 | 30.07 | 9.79 | 0.37 | 0.77 | −0.37 |
| Healthy Control | PARP9 | 25.66 | 5.02 | 0.00 | 1.00 | 0.00 |
| Subject 3 | PARP9 | 24.23 | 4.84 | −0.18 | 1.13 | 0.18 |
| Subject 4 | PARP9 | 23.06 | 3.88 | −1.15 | 2.21 | 1.15 |
| Subject 5 | PARP9 | 25.77 | 5.49 | 0.47 | 0.72 | −0.47 |
| Healthy Control | PLSCR1 | 26.14 | 5.49 | 0.00 | 1.00 | 0.00 |
| Subject 3 | PLSCR1 | 24.05 | 4.66 | −0.83 | 1.78 | 0.83 |
| Subject 4 | PLSCR1 | 21.97 | 2.78 | −2.71 | 6.56 | 2.71 |
| Subject 5 | PLSCR1 | 25.67 | 5.39 | −0.11 | 1.08 | 0.11 |

TABLE 2-continued

| Sample Name | Target Name | CT | ΔCT | ΔΔCT | $2^{-\Delta\Delta CT}$ | $\log2(2^{-\Delta\Delta CT})$ |
|---|---|---|---|---|---|---|
| Healthy Control | SAMD9L | 27.10 | 6.46 | 0.00 | 1.00 | 0.00 |
| Subject 3 | SAMD9L | 25.98 | 6.59 | 0.14 | 0.91 | -0.14 |
| Subject 4 | SAMD9L | 24.17 | 4.99 | -1.47 | 2.77 | 1.47 |
| Subject 5 | SAMD9L | 26.98 | 6.70 | 0.24 | 0.85 | -0.24 |

Healthy Control mean CT of housekeeping genes: 20.64
Subject 1 mean CT of housekeeping genes: 19.39
Subject 2 mean CT of housekeeping genes: 19.19
Subject 3 mean CT of housekeeping genes: 20.28

TABLE 3

| | Sum of log2 fold changes ($\text{SUMlog2}(2^{-ddCT})$) | Precursor POISE score | POISE score |
|---|---|---|---|
| Subject 1 | 30.26 | 13 | 57 |
| Subject 2 | -0.10 | 44 | 26 |
| Subject 3 | -6.20 | 50 | 20 |
| Subject 4 | 24.10 | 20 | 50 |
| Subject 5 | -6.51 | 50 | 20 |

The POISE Scores derived from the expression profiling were 57 for Subject 1, 26 for Subject 2, 20 for Subject 3, 50 for Subject 4 and 20 for Subject 5. Subjects with POISE score of 35 or more (e.g. subjects 1 and 4) were defined as having elevated IFN-I signature and eligible to participate to the clinical trial.

Subject eligibility to participate to the clinical trial could also be assessed utilizing threshold $\text{SUMlog2}(2^{-ddCT})$ of 8.725. Utilizing this threshold, subjects 1 and 4 would be eligible to participate to the clinical trial.

Figure 4:
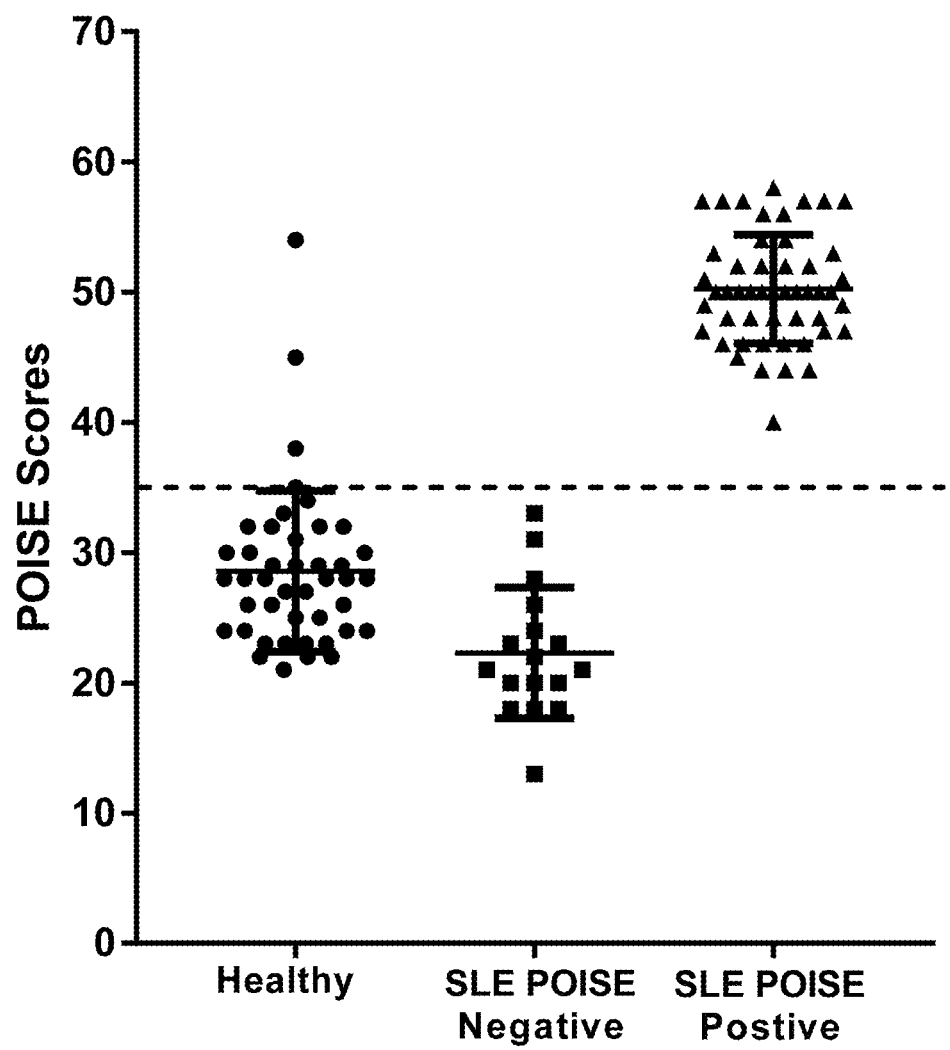
FIG. 4 shows the distribution of POISE Score in SLE and Healthy subjects (HC) calculated on qPCR samples. A POISE score of 35 correctly discriminated 2 populations of SLE subjects; one having elevated IFN-I in comparison with the majority of healthy controls and one with an elevated IFN-I signature.

FIG. 4 shows the distribution of determined POISE scores from healthy control (HC) subjects and SLE donors determined to have baseline or elevated IFN-I signature based on the threshold POISE Score of 35. Subjects with POISE score of equal to 35 or greater were eligible to be enrolled to the study provided other eligibility requirements were met.

Example 3. Automation of Generation and Collection of the POISE Score

Creating the Validated Spreadsheet to Generate the POISE Score

An Excel spreadsheet was designed to automatically generate a POISE score from the exported Viia7 qPCR instrument raw data file with minimal user interface. To begin, sheet 1 of the Excel spreadsheet contained a designated space in which the user copied the raw qPCR data into. On sheet 2, all calculations utilized to arrive at the log 2 fold changes were automatically populated for the 10 genes of interest after qPCR raw data was copied into sheet 1. Calculations were as follows:
1) The mean CT value was determined for the following housekeeping genes: ACTB, B2M, and GAPDH.
2) The delta CT (ΔCT) was determined by subtracting the mean of the housekeeping genes from the CT of each of the 10 target genes.
3) The ΔCT of the pooled healthy sample was subtracted from the ΔCT of each SLE sample to determine the delta CT (ΔΔCT).
4) The fold change between the pooled healthy control and each SLE sample was determined by calculating $2^{-\Delta\Delta CT}$,
5) The base 2 logarithm of the $2^{-\Delta\Delta CT}$ fold change was determined.

Sheet 3 of the spreadsheet contains the POISE score calculation formula for each SLE sample run on the array. The end user submitted this number into the IWRS system which was relayed back to the clinical sites and indicated whether the subject met IFN-I signature inclusion criteria. This spreadsheet was validated as an approved tool to generate the POISE score.

Figure 5:
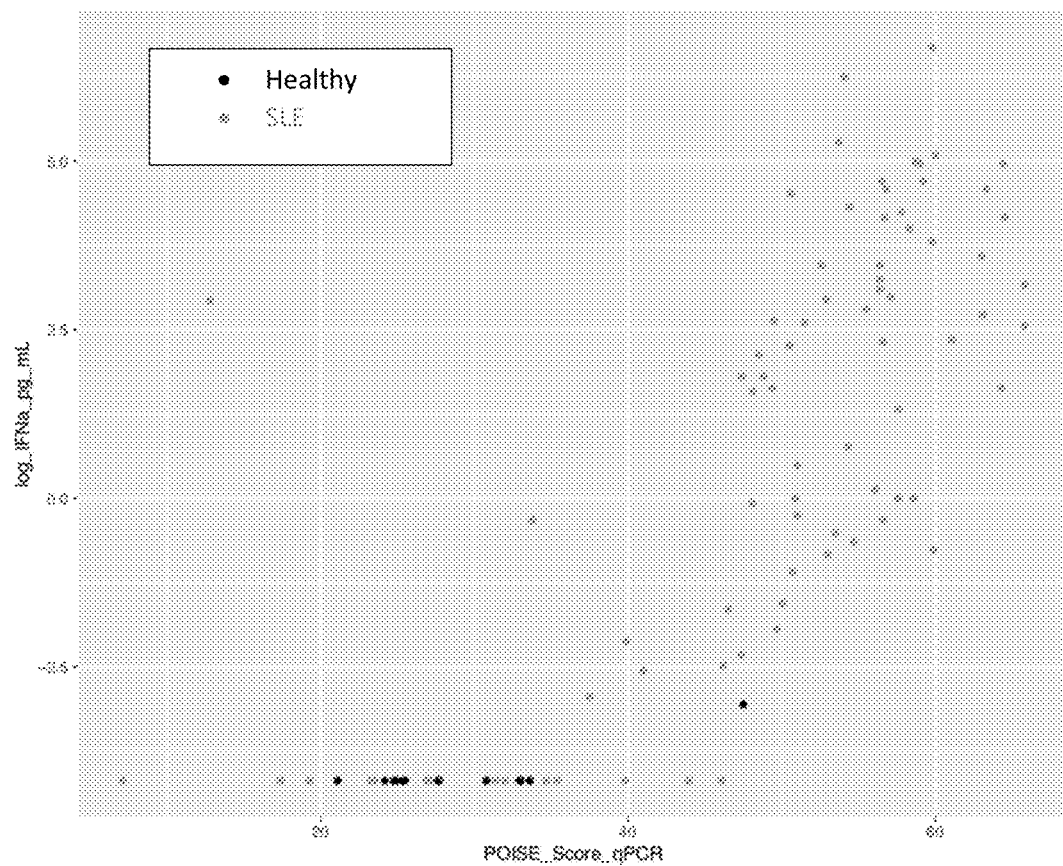
FIG. 5 shows the correlation of the POISE Score with serum IFN-α protein concentrations (log(pg/mL)) indicating that the POISE Score (x-axis) detects elevated IFN-I signature before IFN-α protein concentration (y-axis) reaches assay detectable levels in the serum of lupus patients or healthy control subjects.

Example 4. POISE IFN-I Signature Analysis is More Sensitive than Direct Detection of IFN-I by ELISA Healthy control and SLE patient samples were examined to determine the relationship between the POISE score from RNA isolated from the blood of patients versus the direct level of IFN-α protein in the serum from the same patient collected at the same time. A highly sensitive single molecule array platform (Simoa) was utilized to accomplish protein quantification. The POISE assay enabled quantification of IFN-I activity in samples before direct detection by ELISA using this highly sensitive platform enabling healthy donor levels of IFN-I activity to be distinguished between donors. As IFN-α became detectable by ELISA the POISE scores and IFN-α levels were positively correlated reaffirming the specificity of the POISE as a marker of IFN-I pathway activation. This data indicated that the POISE is a highly sensitive means to quantify IFN-I levels even in healthy human subjects which would also enable robust measurement of pharmacodynamic responses in SLE patients undergoing treatment with IFN-I inhibitor treatment. FIG. 5 shows the correlation of the POISE Score and plasma IFN-α concentration (log(pg/ml)) in healthy (black dots) or SLE subjects (gray dots).

Example 5. Safety, Tolerability and Clinical Response in Healthy Volunteers and Participants with Mild-to-Moderate Systemic Lupus Erythematosus (NCT0260978)

The clinical study design is described in Example 2 and in this Example. In this first-in-human Phase I, 2-part, randomized, double-blind, placebo-controlled, multicenter design study, a single-ascending intravenous (IV) dose of 0.3 mg/kg to 15 mg/kg or a single subcutaneous dose of 1 mg/kg was administered to healthy volunteers (Part A) and multiple IV doses of 10 mg/kg were administered to participants with mild-to-moderate systemic lupus erythematosus (SLE) (Part B).

Summary of the results: The pharmacokinetic profile of JNJ-55920839 was generally similar in healthy volunteers and participants with SLE. Bioavailability of JNJ-55920839 was approximately 80% in healthy volunteers. No antidrug antibodies were detected. In participants with SLE, JNJ-55920839 treatment appeared to associate with clinical responses measured by the Systemic Lupus Erythematosus Responder Index, Systemic Lupus Erythematosus Disease Activity Index 2000, and Physician's Global Assessment relative to placebo. Infections were the most common adverse events reported in both parts of the study with numerically increased rate in exposed over placebo; in 2 participants with SLE, locally disseminated herpes zoster of the skin was reported.

Conclusion: The JNJ-55920839 pharmacokinetic profile was similar to other monoclonal antibodies and was well tolerated and safe in healthy volunteers and participants with SLE. Clinical responses and dysregulation of IFN-I signature were improved in JNJ-55920839 treated participants compared with placebo.

Significance of the Study

JNJ-55920839 was found to be safe and well tolerated in healthy volunteers and participants with mild-to-moderate SLE exhibiting an elevated IFN-I at screening.

Improvements in SRI responses, SLEDAI-2K responses, and Physician's Global Assessment were observed after six 10 mg/kg IV doses of JNJ-55920839 in participants with mild-to-moderate SLE.

POISE expression signature was utilized for participant inclusion and to assess PD effects of JNJ-55920839 in part B of this trial.

JNJ-55920839 treated participants exhibited a pronounced and intended temporal PD effect on IFN-I signature expression in whole blood compared with the placebo population.

Infection events appeared to associate with exposure to study agent. Additional research is needed to optimize the dosing regimen and further characterize safety for SLE participants.

Inclusion criteria for healthy volunteers (Part A) included men or women aged 18 to 55 years, inclusive; body weight of 50 to 90 kg, inclusive; and body mass index of 18 to 30 kg/m², inclusive. Female volunteers were required to be postmenopausal or surgically sterile and have a negative pregnancy test at screening. General inclusion criteria for participants with mild-to-moderate SLE (Part B) were similar to those for healthy volunteers, except that body weight could go down to 40 kg and up to 100 kg, inclusive. Concomitant medications were limited by dosage or number: if on oral corticosteroids, participant must be on stable dose equivalent to an average dose of ≤7.5 mg daily prednisone for 6 weeks prior to first dose; if on antimalarial (eg, chloroquine and hydroxychloroquine), participant must be on stable dose for 6 weeks prior to first dose; and participants were limited to 1 immunosuppressive drug without exceeding dose levels specified for each drug (methotrexate ≤20 mg/week, azathioprine/mercaptopurine ≤2 mg/kg/day, or mycophenolate mofetil/mycophenolic acid equivalent ≤2 g/day). Participants with lupus nephritis were also required to exhibit an active extrarenal feature of lupus at the time of entry. Additionally, participants had to meet the following key criteria at enrollment: Systemic Lupus International Collaborating Clinics modification of the criteria from the American College of Rheumatology (Petri et al., *Arthritis Rheum* 64: 2677-86, 2012) for diagnosis of lupus with at least 1 Systemic Lupus Erythematosus Disease Activity Index 2000 (SLEDAI-2K)-defined nonserologic clinical activity within 3 months prior to first dose of study drug. In addition to meeting criteria from the Systemic Lupus International Collaborating Clinics, the participant must be serologically defined as positive within 2 months prior to first dose or at screening by a positive antinuclear antibody titer of ≥1:80 or a positive anti-double-stranded deoxyribonucleic acid test or a positive anti-Smith antibody, positive anti-ribonucleoprotein antibody and/or anti-Ro antibody, and in addition to at least one of the above, a positive lupus IFN-I signature score at screening as assessed using the POISE score.

For both parts of the study, subjects were excluded if they had a serious infection within 4 months prior to the screening visit, had a coexisting medical condition or past history that was concerning to the investigator, or had active or latent tuberculosis.

Part A of the study assessed the safety, tolerability, PK, and immunogenicity of a single administration of JNJ-55920839 or placebo in healthy volunteers. A computer-generated randomization schedule was used to randomly assign volunteers to a treatment group. Single-ascending IV doses ranging from 0.3 mg/kg to 15.0 mg/kg of JNJ-55920839 or placebo were administered to sequential cohorts of healthy volunteers as an IV infusion. An additional cohort received a single 1 mg/kg SC administration of JNJ-55920839.

Part B of the study explored the safety, tolerability, clinical response, PK, PD using the POISE score, and immunogenicity in participants with SLE. Six doses of 10 mg/kg JNJ-55920839 or placebo were administered every 2 weeks as an IV infusion. Randomization was stratified by racial/ethnic subpopulation (Asian/non-Asian) and elevated level of serologic disease activity (present [antinuclear antibody ≥1:160 titer or presence of lupus autoantibodies] or absent [antinuclear antibody absent or <1:160 titer and no lupus autoantibodies]), and participants were assigned based on a computer-generated randomization schedule.

Study subjects were involved for approximately 13 weeks for Part A and 22 weeks for Part B, including a screening visit up to 28 days before administration of study drug. Healthy volunteers stayed at the study site for 6 days and 5 nights. All subjects received study drug on Day 1, and participants with mild-to-moderate SLE received additional doses on Days 15, 29, 43, 57, and 71.

Blood Sampling and Bioanalysis

Blood samples for all Part A cohorts were collected prior to study drug administration and at various timepoints up to 63 days after dosing. For Part B, blood samples were collected predose and at various timepoints up to 129 days after first study drug administration. Serum samples were analyzed to determine concentrations of JNJ-55920839 using a validated, immunoassay method with a lower limit of quantification of 0.06 μg/mL. In addition, serum samples were used to evaluate antibodies to JNJ-55920839 using a validated assay method.

IFN-I Signature Score (POISE Score)

A whole-blood quantitative polymerase chain reaction-based 10 gene IFN-I gene signature was developed to enable enrollment of participants based on IFN-I signature levels at screening. Generation of the signature threshold was calculated based on the following genes: DHX58, EIF2AK2, HERC5, IFI44, IFI44L, IFI6, IRF7, PARP9, PLSCR1, and SAMD9L. This combination of genes and threshold was empirically derived using machine learning methods and internal data sets to best classify healthy volunteers versus SLE participants. This IFN-I gene signature was also quantified by RNA-sequencing of longitudinally collected blood samples in the study to assess the PD of JNJ-55920839 and the stability of the signature over time in the placebo arm.

Noncompartmental PK Analysis

Noncompartmental PK analysis was performed using Phoenix™ WinNonlin® (version 6.2.1; Tripos LP, USA). Mean terminal elimination half-life (tim) was calculated as $0.693/\lambda z$, with $\lambda z$ being the apparent terminal elimination rate-constant, estimated by linear regression using the terminal log-linear phase of the logarithmic transformed concentration versus time curve. Absolute bioavailability after SC administration was calculated from the ratio of area under the serum concentration-time curve following SC and IV administration of the same dose of JNJ-55920839.

Safety and Clinical Response Evaluations

Safety and tolerability were evaluated until Day 64 for healthy volunteers (Part A) and Day 130 for participants with mild-to-moderate SLE (Part B). The safety population included any subjects who received any administration of JNJ-55920839 or placebo. Evaluations included adverse event (AE) assessments, vital sign measurements, electrocardiogram measurements, clinical laboratory tests, and physical examinations. Treatment-emergent adverse events (TEAEs) were coded in accordance with the Medical Dictionary for Regulatory Activities versions 18.1 (Part A) and 21.0 (Part B).

Response evaluations and patient-reported quality of life measures included SLEDAI-2K/SLEDAI-2K Responder Index (S2K RI-50), British Isles Lupus Assessment Group (22), Cutaneous Lupus Erythematosus Disease Area and Severity Index (CLASI), Physician's Global Assessment (PGA) of Disease Activity, Short-form-36 questionnaire (SF-36), EuroQol-5 dimensions-5 levels (EQ-5D-5L) Patient Diary, and Joint Assessment. All evaluations were completed predose on Days 1, 15, 29, 57, 71, and 100.

Results

Study Populations and Disposition

For Part A, 48 healthy volunteers from a single site in Belgium were randomized to receive single-ascending IV (n=30) or SC (n=6) doses of JNJ-55920839 or placebo (n=12; Table 4). There were more male (40 [83.3%]) than female (8 [16.7%]) volunteers. The mean age of the study population in Part A was 40.4 years (standard deviation [SD]=11.37), and the mean body mass index and baseline weight were 25.27 kg/m² (SD=2.61) and 78.77 kg (SD=9.97), respectively. Demographics and disposition of placebo and JNJ-55920839 volunteers were similar (Table 4).

TABLE 4

| | Placebo (n = 12) | JNJ-55920839 (mg/kg) | | | |
|---|---|---|---|---|---|
| | | IV 0.3 (n = 6) | IV 1 (n = 6) | IV 3 (n = 6) | IV 10 (n = 6) |
| Age (years) | | | | | |
| Mean (SD) | 41.3 (9.81) | 42 (10.28) | 38 (13.08) | 51.2 (4.88) | 35.5 (11.61) |
| Sex, n (%) | | | | | |
| Female | 3 (25) | 0 | 1 (16.7) | 2 (33.3) | 0 |
| Male | 9 (75) | 6 (100) | 5 (83.3) | 4 (66.7) | 6 (100) |
| Race, n (%) | | | | | |
| Black/African American | 0 | 0 | 0 | 0 | 0 |
| White | 12 (100) | 6 (100) | 6 (100) | 6 (100) | 6 (100) |
| Weight (kg) | | | | | |
| Mean (SD) | 82.7 (9.157) | 79.87 (8.709) | 75.58 (7.639) | 79.85 (6.775) | 81.25 (4.819) |
| BMI (kg/m²) | | | | | |
| Mean (SD) | 26.22 (2.829) | 25.02 (2.807) | 24.88 (2.278) | 26.57 (1.269) | 24.42 (1.537) |

| | JNJ-55920839 (mg/kg) | | | |
|---|---|---|---|---|
| | IV 15 (n = 6) | SC 1 (n = 6) | Combined (n = 36) | Total (n = 48) |
| Age (years) | | | | |
| Mean (SD) | 41.2 (11.84) | 32.5 (13.13) | 40.1 (11.95) | 40.4 (11.37) |
| Sex, n (%) | | | | |
| Female | 1 (16.7) | 1 (16.7) | 5 (13.9) | 8 (16.7) |
| Male | 5 (83.3) | 5 (83.3) | 31 (86.1) | 40 (83.3) |
| Race, n (%) | | | | |
| Black/African American | 0 | 1 (16.7) | 1 (2.8) | 1 (2.1) |
| White | 6 (100) | 5 (83.3) | 35 (97.2) | 47 (97.9) |

TABLE 4-continued

| | | | | |
|---|---|---|---|---|
| Weight (kg) | | | | |
| Mean (SD) | 77.87 (14.578) | 70.32 (13.722) | 74.46 (10.006) | 78.77 (9.972) |
| BMI (kg/m$^2$) | | | | |
| Mean (SD) | 25.65 (2.604) | 23.22 (3.455) | 24.96 (2.491) | 25.27 (2.607) |

BMI, body mass index;
IV, intravenous;
SC, subcutaneous;
SD, standard deviation

For Part B, 28 participants with mild-to-moderate SLE from 19 sites in 7 countries were randomized to receive study drug (n=20; 10 mg/kg IV) or placebo (n=8; Table 5). There were more female (27 [96.4%]) than male (1 [3.6%]) participants. Of these, 15 (53.6%) participants were self-described as Asian, 2 (7.1%) were black/African American, and 11 (39.3%) were white. The mean age of the study population was 35.9 years (SD=9.30), mean body mass index was 22.5 kg/m$^2$ (SD=3.42), and mean baseline weight was 58.4 kg (SD=8.77). The baseline characteristics (disease, criteria from the Systemic Lupus International Collaborating Clinics, and lupus nephritis classification) and demographics were well balanced between the study drug and placebo cohorts (Table 5). Overall use of selected prior medications (methotrexate, systemic corticosteroids, and chloroquine/hydroxychloroquine) and concomitant medications at baseline was balanced between both placebo and study drug cohorts.

TABLE 5

| | Placebo (n = 8) | JNJ-55920839 10 mg/kg IV (n = 20) | Total (n = 28) |
|---|---|---|---|
| Age (years) | | | |
| Mean (SD) | 39.5 (8.00) | 34.5 (9.58) | 35.9 (9.30) |
| Sex, n (%) | | | |
| Female | 8 (100.0%) | 19 (95.0%) | 27 (96.4%) |
| Male | 0 | 1 (5.0%) | 1 (3.6%) |
| Race, n (%) | | | |
| Black/African American | 0 (0%) | 2 (10.0%) | 2 (7.1%) |
| Asian | 4 (50.0%) | 11 (55.0%) | 15 (53.6%) |
| White | 4 (50.0%) | 7 (35.0%) | 11 (39.3%) |
| Weight (kg) | | | |
| Mean (SD) | 56.3 (6.90) | 59.2 (9.45) | 58.4 (8.77) |
| BMI (kg/m$^2$) | | | |
| Mean (SD) | 22.1 (3.48) | 22.6 (3.47) | 22.5 (3.42) |
| Baseline SLED AI -2K (0-105) | | | |
| Mean (SD) | 9.5 (3.16) | 9.0 (3.63) | 9.1 (3.45) |
| Baseline PGA (VAS 0-10 cm) | | | |
| Mean (SD) | 3.0 (1.41) | 2.9 (1.32) | 2.9 (1.32) |
| Baseline Joints with Pain and Inflammation | | | |
| Mean (SD) | 2.8 (2.71) | 1.2 (0.89) | 1.6 (1.73) |
| Anti-RNP | | | |
| Positive | 2 (25.0%) | 11 (55.0%) | 13 (46.4%) |
| Negative | 6 (75.0%) | 9 (45.0%) | 15 (53.6%) |
| Anti-Smith | | | |
| Positive | 2 (25.0%) | 5 (25.0%) | 7 (25.0%) |
| Negative | 6 (75.0%) | 14 (70.0%) | 20 (71.4%) |
| Anti-SSA/Ro | | | |
| Positive | 3 (37.5%) | 15 (75.0%) | 18 (64.3%) |
| Negative | 5 (62.5%) | 4 (20.0%) | 9 (32.1%) |

TABLE 5-continued

|  | Placebo (n = 8) | JNJ-55920839 10 mg/kg IV (n = 20) | Total (n = 28) |
|---|---|---|---|
| Antinuclear Antibodies | | | |
| Mean (SD) | 580.0 (832.21) | 1130.0 (1178.88)$^a$ | 946.7 (1089.63)$^b$ |
| Anti-Double-Stranded DNA | | | |
| Mean (SD) | 85.0 (107.17) | 126.7 (173.17)$^c$ | 113.8 (154.90)$^d$ |

BMI, body mass index; IV, intravenous; PGA, Physician's Global Assessment of Disease Activity; RNP, ribonucleoprotein; SD, standard deviation; SLE, systemic lupus erythematosus; SLEDAI-2K, Systemic Lupus Erythematosus Disease Activity Index 2000; SSA/Ro, SSA/Ro antigen; VAS, visual analogue scale.
$^a$n = 16
$^b$n = 24
$^c$n = 18
$^d$n = 26

A total of 46 healthy volunteers completed Part A, and 25 participants completed Part B of the study. Two volunteers from the study drug cohort did not complete Part A; reasons included an AE of myringitis bullous and an elective withdrawal from the study. Both volunteers completed the early termination visit. A total of 3 participants did not complete Part B of the study; reasons for terminating participation included AE (n=1, groin pain: lymphadenopathy) and "other reasons" (n=2; participants were randomized, but not dosed due to exclusionary electrocardiogram abnormalities prior to dosing).

POISE Scores at Screening

Figure 6:
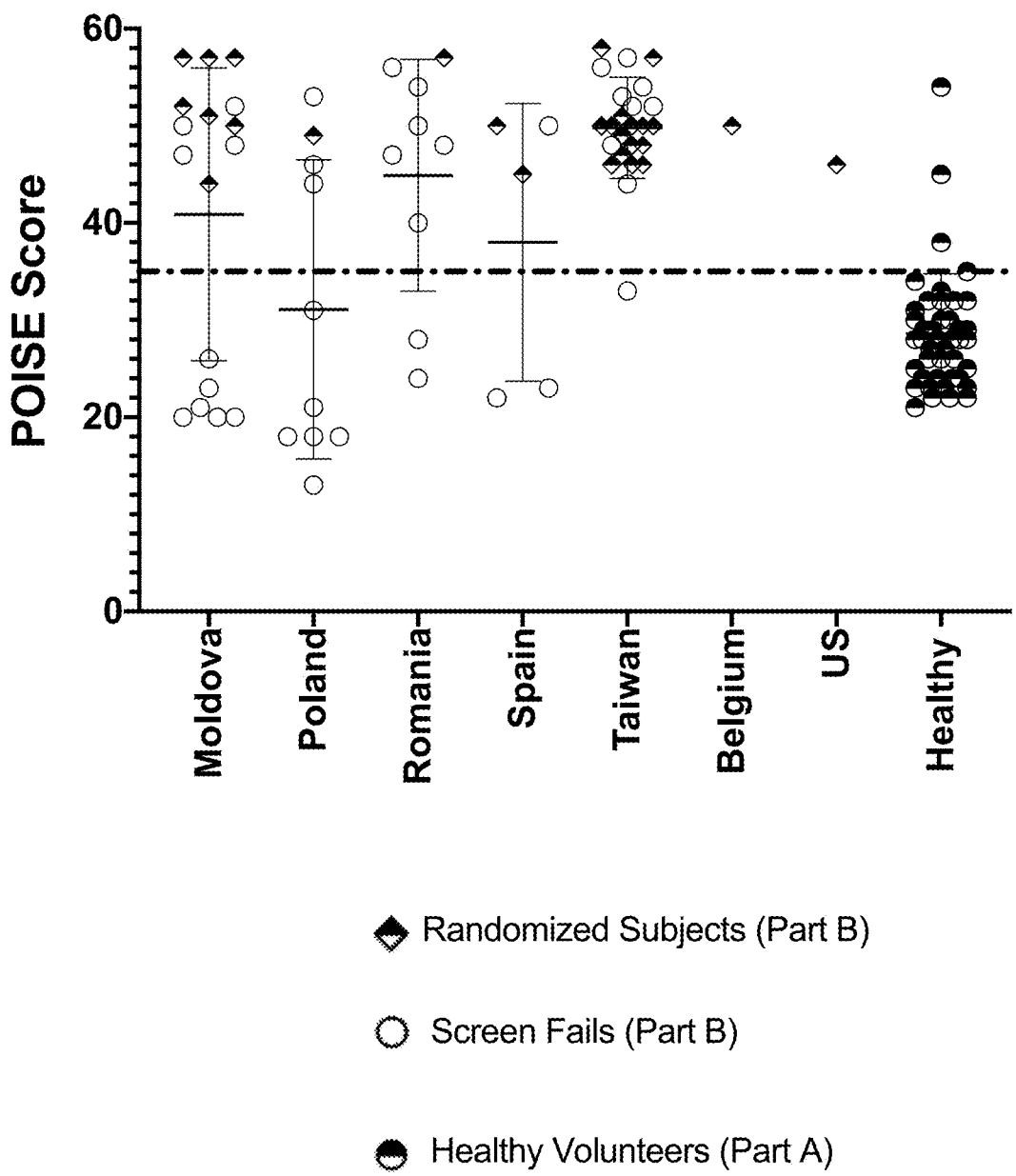
FIG. 6 shows the distribution of POISE scores at the time of screening for JNJ-55920839 phase 1 study. in SLE and healthy subjects based on site geography. POISE score of >35 was considered IFN-I positive and required for enrollment of part B of trial.

One of the primary goals in this study was to assess the impact of JNJ-55920839 on the IFN-I signature in participants with an elevated IFN-I signature score at screening. IFN-I signature was assessed using POISE. The POISE scores from the screened SLE participants revealed both a separation between healthy control samples and the SLE population as well as a bimodal distribution of The POISE scores within the SLE population (FIG. 6). The screening scores also revealed predominantly POISE scores above the threshold in the cohort of participants from Taiwan relative to the other cohorts.

Figure 7:
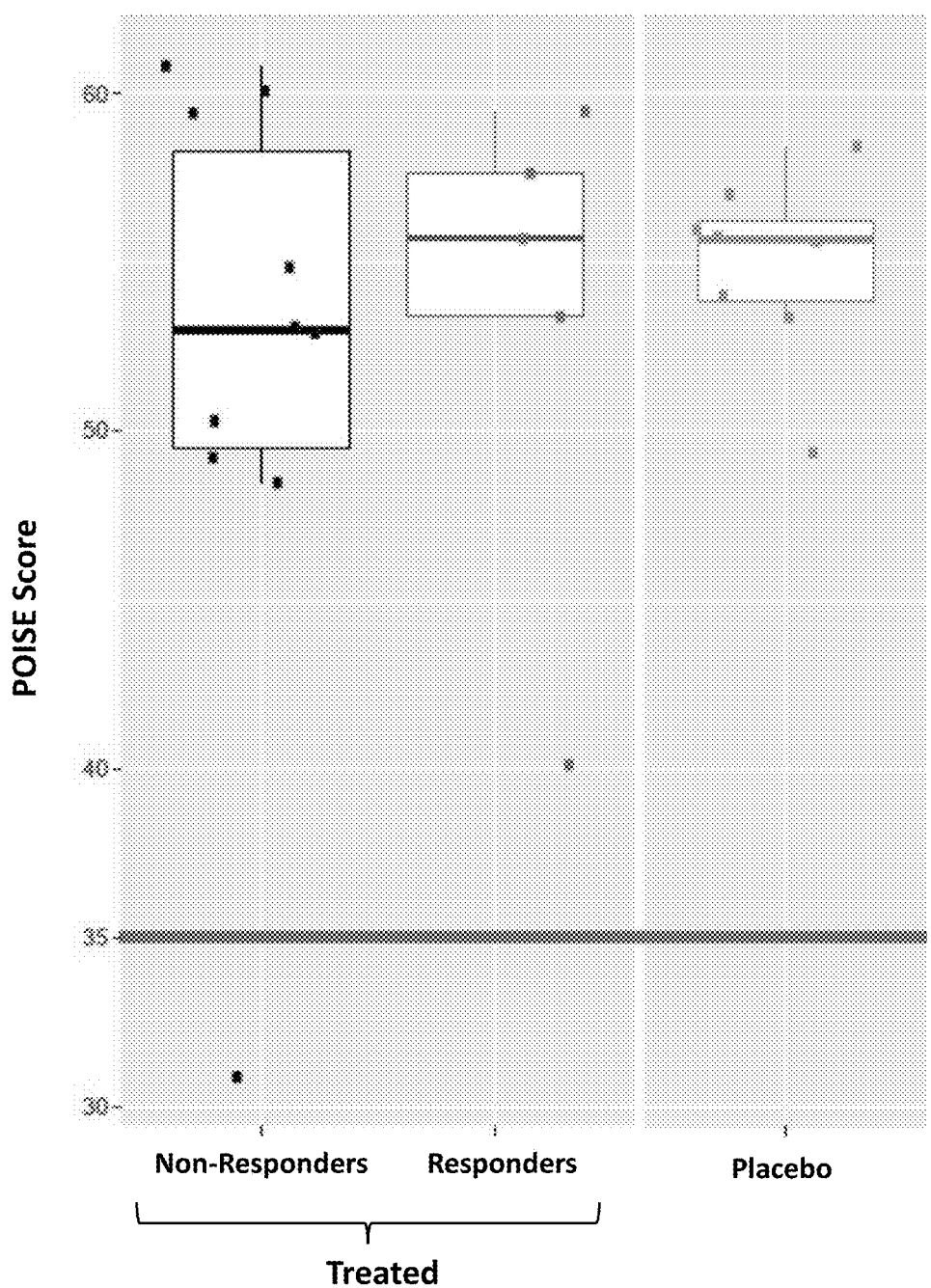
FIG. 7 shows the assessment of the POISE scores at baseline by response status (non-responders: n=10; responders: n=5; placebo: n=8). Response status was based on SRI-4 at day 100.

Although not reaching statistical significance, baseline POISE scores were slightly higher in the JNJ-55920839 responder population than in the non-responder population (FIG. 7). One participant presented as negative at baseline despite being IFN-I positive at screening. This participant remained below the IFN-I signature cutoff for the remainder of the study.

Pharmacokinetics

After a single IV infusion of JNJ-55920839 across the dose range of 0.3 mg/kg to 15 mg/kg, there was an approximately dose-dependent and dose-proportional increase in maximum PK concentration and area under the serum concentration-time curve. Mean $t_{1/2}$ was similar after IV infusion (20.7 days to 24.6 days) and SC injection (24.6 days) in healthy volunteers. The absolute bioavailability of JNJ-55920839 administered as an SC injection, based on the comparison with an IV infusion at the same dose, was estimated at approximately 80%.

PK profile following the first dose was similar in participants with mild-to-moderate SLE compared with those in healthy volunteers, with a biphasic disposition. For participants with SLE following multiple IV infusions of JNJ-55920839 (10 mg/kg), steady state was achieved within 43 days of treatment (Dose 4). Mean $t_{1/2}$ after Dose 6 was 14.8 days.

Immunogenicity

No subject developed antibodies to JNJ-55920839 following single administration of JNJ-55920839 IV between 0.3 mg/kg to 15 mg/kg or SC at 1 mg/kg in healthy volunteers or multiple administrations of JNJ-55920839 IV at 10 mg/kg in participants with mild-to-moderate SLE.

Clinical Response in Participants with SLE

Figure 8:
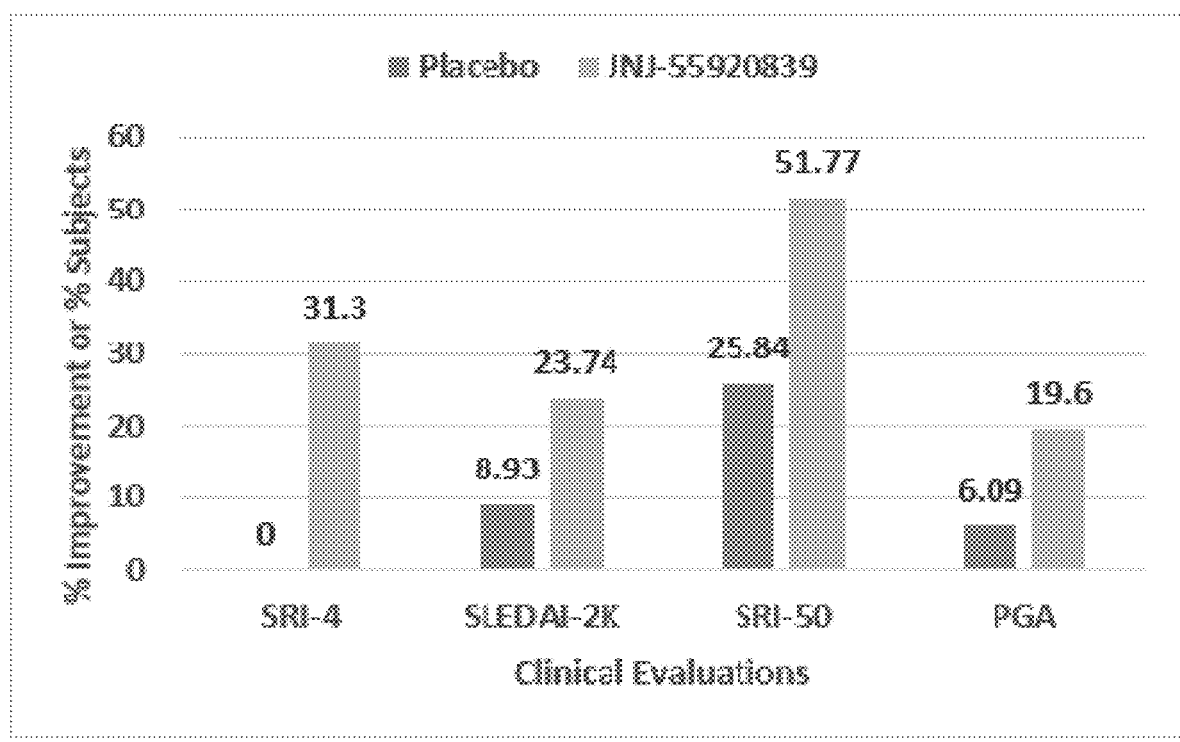
FIG. 8 shows the clinical responses at day 100 of four secondary descriptive endpoints in placebo (left column in each group) and JNJ-55920839 (right column in each group) treated subjects. PGA, Physician's Global Assessment of Disease Activity; SLEDAI-2K, Systemic Lupus Erythematosus Disease Activity Index 2000; SRI, Systemic Lupus Erythematosus Responder Index; SRI-4, 4 point or greater improvement in SRI; SRI-50, 50% response rate for improvement in SLEDAI.

Overall Systemic Lupus Erythematosus Responder Index with a 4-point or greater improvement (SRI-4) response data at Day 100 shows that participants receiving JNJ-55920839 had a numerically greater response rate than those who received placebo (31.3% vs 0%, respectively; FIG. 8). The JNJ-55920839 cohort showed a greater reduction than the placebo cohort for SLEDAI-2K and S2K RI-50. Mean percentage change from baseline at Day 100 for SLEDAI-2K was a decrease of 23.74 (SD=27.06) vs 8.93 (SD=13.14), respectively; mean percentage change from baseline at Day 100 for S2K RI-50 was a decrease of 51.77 (SD=24.76) vs 25.84 (SD=22.16), respectively. Mean percentage change from baseline to Day 100 in PGA was greater for the JNJ-55920839 cohort than the placebo cohort (decrease of 19.60 [SD=36.25] vs 6.09 [SD=29.15], respectively).

In addition, the JNJ-55920839 cohort exhibited a numerically smaller number of swollen joints than the placebo cohort. There was no difference between JNJ-55920839 and placebo for overall CLASI activity (−27.3% vs −20.4%, respectively), but baseline activity was low. For several clinical and patient-reported outcomes, no changes were observed between treatment cohorts from baseline to after treatment (no new A or 2B shifts per British Isles Lupus Assessment Group, number of time to SLEDAI flare from Day 1 through Day 100, and overall scores or individual domains of EQ-5D-5L and SF-36).

Pharmacodynamics

Figure 9:
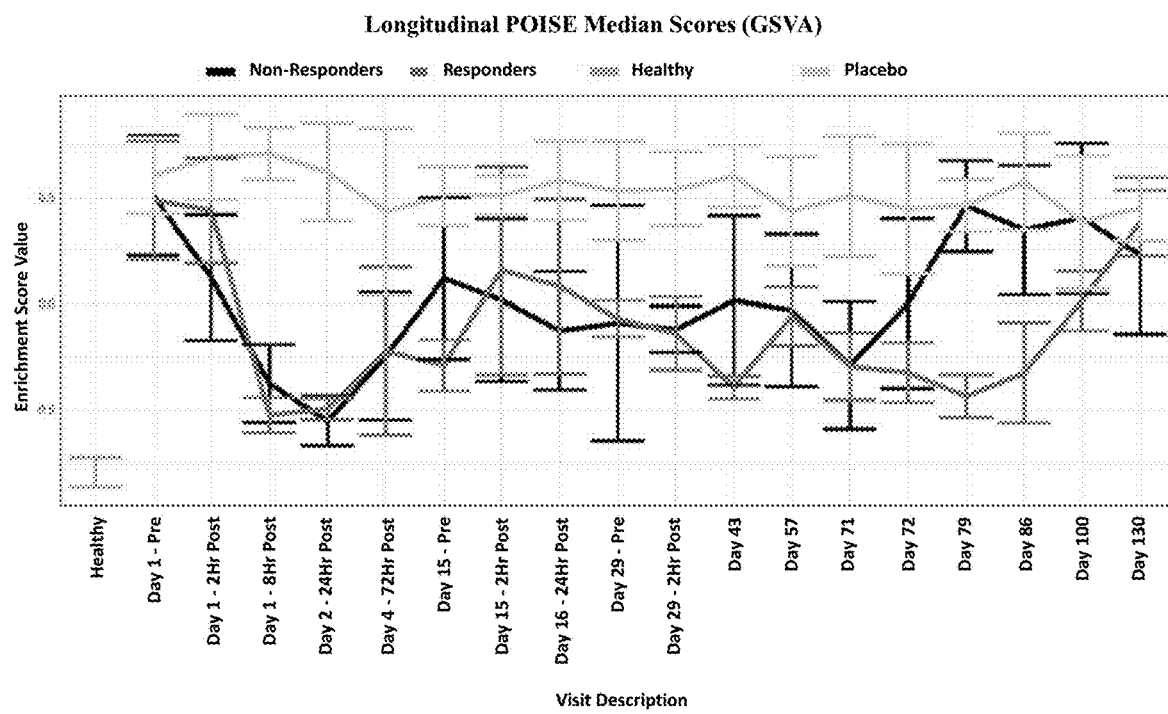
FIG. 9 shows RNA-Seq assessment of the POISE scores in JNJ-55920839 responders and non-responders after the dosing period. Longitudinal IFN-I median score gene assessment using GSVA analysis. Error bars represent the MAD. Response status based on SRI-4 at day 100.

RNA-Sequence analysis indicated that temporal suppression of the IFN-I signature as measured using the POISE score in the blood was rapid and largely comparable between JNJ-55920839 responders and non-responders (SRI-4 at Day 100) throughout the dosing period from Day 1 through Day 71 with signature levels approaching the cut-off score for enrollment inclusion. The placebo group, by contrast, did not exhibit significant changes in the POISE scores over time (FIG. 9). After the last dose at Day 71, JNJ-55920839 responders exhibited sustained POISE score suppression through Day 86 reaching placebo levels at Day 130, whereas JNJ-55920839 non-responder signature levels rapidly reached placebo levels at Day 79 (FIG. 9).

Safety and Tolerability

During Part A, 39 of 48 healthy volunteers (81.3%) reported experiencing 1 or more TEAEs. The most common TEAE was reported in the system organ class (SOC) of Infections and Infestations (12/48 [25%]) with a higher percentage of volunteers who were exposed to JNJ-55920839 experiencing infections than those exposed to placebo (27.8% vs 16.7%, respectively; Table 6). There was a possible association between increasing dose of study drug and the percentage of volunteers who experienced infections. All TEAEs of infections were nonserious.

One infection in a healthy volunteer treated with JNJ-55920839 resulted in discontinuation at their own discretion; this volunteer experienced myringitis bullous that responded to conventional therapy. Additional infections/infestations were observed, primarily upper respiratory, and were not serious; no cases of herpes zoster were noted.

During Part B of the study, similar rates of TEAEs were observed in both cohorts, and a total of 20 participants reported experiencing 1 or more TEAEs. Similar to Part A, the most common TEAE reported was in the SOC of Infections and Infestations (10 [38.5%] participants). However, there was a higher rate in the JNJ-55920839 treatment cohort compared with the placebo cohort (50% vs 12.5%, respectively; Table 7). The infections observed in the JNJ-55920839 cohort included common bacterial and viral infections as well as 2 serious adverse events of locally disseminated herpes zoster. A higher rate of events in the SOC of Gastrointestinal Disorders was also reported in the JNJ-55920839 cohort compared with the placebo cohort (16.7% vs 0% participants, respectively). However, these TEAEs were all symptoms rather than a specific diagnosis.

Serious TEAEs were reported by 2 (7.7%) participants from the JNJ-55920839 cohort including 2 cases of herpes zoster (7.7%) and premature labor in 1 participant (3.8%). No serious TEAEs were reported in the placebo cohort. One participant treated with JNJ-55920839 10 mg/kg IV discontinued participation because of a nonserious TEAE of groin pain (lymphadenopathy), which was considered as possibly related to the study drug by the investigator and eventually resolved. The cases of herpes zoster were considered as related to the study drug. As a result, study enrollment was suspended, and inclusion/exclusion criteria were amended to exclude any participants who had already shown at any point in their medical history a predisposition to developing disseminated forms of zoster. No action was taken with regard to these participants because both had received all planned doses prior to the onset of events. The participant with the serious TEAE of premature labor delivered a healthy baby, and the delivery was within 2 days of 37 weeks (full-term pregnancy). No other issues were reported related to the participant or baby, and this was considered not related to the study drug by the study investigator.

No infusion reactions were reported, and no local injection site reactivity was attributed to study drug. There were no clinically meaningful increases in postbaseline chemistry or hematology values for subjects treated with JNJ-55920839.

TABLE 6

| | Placebo (n = 12) | JNJ-55920839 (mg/kg) | | | | | | Combined (n = 36) | Total (n = 48) |
| | | IV 0.3 (n = 6) | IV 1 (n = 6) | IV 3 (n = 6) | IV 10 (n = 6) | IV 15 (n = 6) | SC 1 (n = 6) | | |
|---|---|---|---|---|---|---|---|---|---|
| Average duration of follow-up (weeks) | 12.4 | 13.2 | 10.4 | 15.2 | 13.8 | 11 | 10.8 | 12.4 | 12.4 |
| Subjects with 1 or more treatment-emergent adverse events, n (%) | 2 (16.7) | 1 (16.7) | 2 (33.3) | 1 (16.7) | 4 (66.7) | 1 (16.7) | 1 (16.7) | 10 (27.8) | 12 (25) |
| System organ class/Preferred term, n (%) | | | | | | | | | |
| Infections and Infestations | 2 (16.7) | 1 (16.7) | 2 (33.3) | 1 (16.7) | 4 (66.7) | 1 (16.7) | 1 (16.7) | 10 (27.8) | 12 (25) |
| Rhinitis | 0 | 0 | 2 (33.3) | 1 (16.7) | 2 (33.3) | 0 | 0 | 5 (13.9) | 5 (10.4) |
| Nasopharyngitis | 0 | 0 | 0 | 0 | 1 (16.7) | 1 (16.7) | 1 (16.7) | 3 (8.3) | 3 (6.3) |
| Enterobiasis | 1 (8.3) | 0 | 0 | 0 | 0 | 0 | 0 | 0 | 1 (2.1) |
| Gastroenteritis | 1 (8.3) | 0 | 0 | 0 | 0 | 0 | 0 | 0 | 1 (2.1) |
| Myringitis bullous | 0 | 1 (16.7) | 0 | 0 | 0 | 0 | 0 | 1 (2.8) | 1 (2.1) |
| Viral infection | 0 | 0 | 0 | 0 | 1 (16.7) | 0 | 0 | 1 (2.8) | 1 (2.1) |

Note:

Percentage was calculated with the number of randomized, treated subjects in each study phase as the denominator. Incidence is based on the number of subjects experiencing at least 1 adverse event, not the number of events. Adverse events are coded using MedDRA version 18.1.

IV, intravenous; MedDRA, Medical Dictionary for Regulatory Activities; SC, subcutaneous.

TABLE 7

|  | Placebo (n = 8) | JNJ-55920839 10 mg/kg IV (n = 18) | Total (n = 26) |
|---|---|---|---|
| Average duration of follow-up (weeks) | 18.7 | 18.7 | 18.7 |
| Subjects with 1 or more treatment emergent adverse events, n (%) | 1 (12.5) | 9 (50.0) | 10 (38.5) |
| System organ class/Preferred term, n (%) | | | |
| Infections and Infestations | 1 (12.5) | 9 (50.0) | 10 (38.5) |
| Nasopharyngitis | 1 (12.5) | 5 (27.8) | 6 (23.1) |
| Urinary tract infection | 0 | 3 (16.7) | 3 (11.5) |
| Herpes zoster | 0 | 2 (11.1) | 2 (7.7) |
| Vulvovaginitis | 0 | 2 (11.1) | 2 (7.7) |
| Pharyngitis | 0 | 1 (5.6) | 1 (3.8) |
| Upper respiratory tract infection | 0 | 1 (5.6) | 1 (3.8) |
| Vaginal infection | 1 (12.5) | 0 | 1 (3.8) |

Note:
Percentage was calculated with the number of randomized, treated subjects in each treatment group as the denominator. Incidence is based on the number of subjects experiencing at least 1 adverse event, not the number of events. Adverse events are coded using MedDRA version 21.0.
IV, intravenous; MedDRA, Medical Dictionary for Regulatory Activities.

DISCUSSION

JNJ-55920839, a fully human immunoglobulin Gi kappa monoclonal antibody targeting multiple IFN-α subtypes and IFN-ω, was developed to explore the clinical benefits of specifically neutralizing the activity of these IFNs in participants with SLE having an elevated IFN-I signature. This Phase I study was the first study of the safety, tolerability, PK, immunogenicity, PD, and clinical response in humans following both IV and SC administration. JNJ-55920839 showed linear PK across the IV dose range of 0.3 mg/kg to 15 mg/kg and had similar mean $t_{1/2}$ between IV and SC administration. Similar PK profiles were observed in healthy volunteers and participants with mild-to-moderate SLE, despite the slightly lower clearance observed in these participants. No treatment-induced antidrug antibody to JNJ-55920839 was observed in this first-in-human study. This may not be representative of repeated administrations in the intended patient population.

Overall, JNJ-55920839 at a dose of 10 mg/kg every 2 weeks (6 doses) was associated with numerically better clinical response than placebo, as judged by SRI-4 responses, SLEDAI-2K responses, and PGA. Joint counts showed significant baseline differences across placebo and JNJ-55920839 cohorts, rendering comparisons difficult, but the JNJ-55920839 cohort did show a numerically greater reduction in the number of swollen joints. Few participants had significant CLASI activity at baseline, which made comparisons difficult for this evaluation measurement; however, no difference was seen between JNJ-55920839 and placebo. No improvements were noted in patient-reported outcome measures (SF-36 and EQ-5D-5L). The clinical responses measured by clinical evaluation tools are encouraging as the study was not powered to detect clinical efficacy responses. Additional dose-finding studies that are adequately powered can further optimize the dosing regimen for JNJ-55920839 for clinical responses.

JNJ-55920839 was overall well tolerated among healthy volunteers following a single dose. No infusion reactions occurred, and no local injection site reactivity was attributed to study drug. No serious AEs occurred in Part A of the study. Infections were the most common AE and showed a possible dose response. One infection in a healthy volunteer treated with JNJ-55920839 resulted in discontinuation at their own discretion. This volunteer experienced myringitis bullous requiring antibiotic therapy that responded in an expected time course. Additional infections/infestations were observed, but these were not serious nor did they impact participation in the study. No cases of herpes zoster were noted in the healthy volunteers.

In Part B, 2 cases of locally disseminated herpes zoster infection were observed in participants with mild-to-moderate SLE exposed to the full course of JNJ-55920839 treatment. Both cases resolved without sequelae following conventional therapy. Reactivation of zoster is known to increase with concomitant therapy and SLE and has been reported with other agents that block IFN-I (Furie et al., Arthritis & Rheumatology 69:376-86, 2017; Khamashta et al., Ann Rheum Dis 75:1909-16, 2016). There was no evidence for broader dissemination of zoster or other specific viral infections in this study. The serious TEAE of premature labor is not considered clinically significant as the participant was within 2 days of carrying the pregnancy to term. No clinically significant changes from baseline were observed for laboratory parameters, vital signs, physical examination, or electrocardiogram findings. Increased rates of infection in both parts of the study require additional investigation to understand whether the risk of infection is increased with JNJ-55920839. No notable study limitations were identified.

JNJ-55920839 was well tolerated in both healthy volunteers and participants with mild-to-moderate SLE. The clinical measures showed that responders clustered to the JNJ-55920839 cohort. The safety profile of JNJ-55920839 was acceptable with minor concern for development of infections as AEs. The screening strategy used in this study to include an IFN-I signature using the POISE score may be helpful for future studies.

Longitudinal blood samples from participants treated with JNJ-55920839 indicated a clear PD effect versus placebo. These data also indicated that JNJ-55920839 responders did not achieve a deeper level of suppression of the IFN-I signature versus non-responders during the dosing period (Day 1 through Day 71). Despite this observation, using the POISE score for participant enrollment would be expected to enrich for responders to IFN-I inhibition as indicated by the anifrolumab Phase 2 study results (Furie et al., Arthritis & Rheumatology 69:376-86, 2017). It is interesting to note that, in this study, no placebo response was observed. This is consistent with data from the ustekinumab Phase 2 analysis, which indicated that lower placebo response rates were observed in subjects having higher IFN-I signature levels at baseline (van Vollenhoven et al., *Lancet* 392: 1330-9, 2018). This observation suggests that SLE subjects with high IFN-I signature at baseline are less responsive to standard-of-care therapy. Thus, enriching for participants having elevated IFN-I signature at baseline could potentially be a strategy to minimize placebo responses in SLE trials. Strikingly, there were PD differences observed after the final dose between Days 72 and 100 between JNJ-55920839 responders and non-responders, where JNJ-55920839 responders consistently exhibited suppression of the IFN-I signature and non-responders reached similar levels to placebo by Day 79. It is currently unclear why non-responders failed to exhibit similar levels of IFN-I signature suppression during this time period after dosing because the levels of suppression were largely similar during the dosing period. Serum samples from this study did not reveal antidrug antibodies in these non-responder participants. Although there are clear limitations to this study due to the sample size, these data indicate the possibility of using this post-dosing assessment in an adaptive trial setting where participants who failed to maintain suppression of the signature during this time period would be discontinued from the study or switched into another study.

Another interesting observation from this study was that the greatest level of IFN-I signature suppression was seen immediately after the first dose of JNJ-55920839. Given the clean immunogenicity findings from this study, it is unclear why this initial rapid suppression was not maintained after subsequent doses. It is possible that compensatory factors may have been induced to compensate for the immediate suppression of IFN-I signaling after the first dose, but no such factors have been identified. It is also interesting that the IFN-I suppression seen after the last dose, peaking at Day 79 (approximately 1 week after final dose), was the second greatest level of IFN-I suppression observed in this study and only occurred in the JNJ-55920839 responder group.

We claim:

1. A method of treating a subject having a type I interferon (IFN-I) mediated disease that is responsive to treatment with an IFN-I inhibitor, comprising:
   a) providing a biological sample from the subject;
   b) assaying gene expression of genes DHX58, EIF2AK2, HERC5, IFI44, IFI44L, IFI6, IRF7, PARP9, PLSCR1 and SAMD9L in the biological sample;
   c) determining a combined expression value of the genes DHX58, EIF2AK2, HERC5, IFI44, IFI44L, IFI6, IRF7, PARP9, PLSCR1 and SAMD9L in the biological sample; and
   d) treating the subject with the IFN-I inhibitor when the combined expression value is equal to or higher than a threshold value, wherein the combined expression value is a sum of (i) normalized threshold cycle (CT) values (SUMΔCT) of genes DHX58, EIF2AK2, HERC5, IFI44, IFI44L, IFI6, IRF7, PARP9, PLSCR1 and SAMD9 and the threshold value is SUMΔCT of 57.474 or (ii) log 2 fold changes of normalized differential expression between the biological sample and a biological sample obtained from one or more healthy controls (SUMlog2($2^{-ddCT}$)) of genes DHX58, EIF2AK2, HERC5, IFI44, IFI44L, IFI6, IRF7, PARP9, PLSCR1 and SAMD9L and the threshold value is SUMlog2($2^{-ddCT}$) of 8.725.

2. The method of claim 1, wherein the combined expression value is a POISE Score of Formula I:
   POISE Score=70−|43.7251664−SUMlog2(2^-ddCT))| (Formula I) and the threshold value is the POISE Score of between 30 and 40.

3. The method of claim 2, wherein the threshold value is the POISE score of 35.

4. The method of claim 1, wherein the biological sample is a blood sample or a tissue sample.

5. The method of claim 1, wherein the IFN-I mediated disease is systemic lupus erythematosus (SLE), type I diabetes, psoriasis, primary Sjögren's disease, systemic sclerosis, rheumatoid arthritis, transplant rejection, dermatomyositis, polymyositis, Aicardi-Goutières syndrome, Sting associated vasculopathy with onset in infancy (SAVI) or chronic atypical neutrophilic dermatosis with lipodystrophy and elevated temperature syndrome (CANDLE).

6. The method of claim 5, wherein SLE comprises lupus nephritis, cutaneous lupus or lupus with central nervous system (CNS) manifestations.

7. The method of claim 1, wherein the IFN-I inhibitor is a molecule that blocks interaction of IFN-I with IFNAR, an antagonistic antibody that binds IFN-I, an antagonistic antibody that binds IFNAR, an inhibitor of Tyk2, Jak1, TLR7, TLR8, TLR9 or STING, a modulator or depletor of plasmacytoid dendritic cells; or an agent that degrades nucleic acids.

8. The method of claim 7, wherein the antagonistic antibody that binds IFN-I comprises:
   a) a heavy chain variable region 1 (HCDR1) of SEQ ID NO: 11, a HCDR2 of SEQ ID NO: 12, a HCDR3 of SEQ ID NO: 13, a light chain variable region 1 (LCDR1) of SEQ ID NO: 14, a LCDR2 comprising the amino acid sequence GAS and a LCDR3 of SEQ ID NO: 16;
   b) a heavy chain variable region (VH) of SEQ ID NO: 17 and a light chain variable region (VL) of SEQ ID NO: 18;
   c) a heavy chain (HC) of SEQ ID NO: 19 and a light chain (LC) of SEQ ID NO: 20, or
   d) any combination of a), b) and c).

9. The method of claim 8, wherein the antagonistic antibody that binds IFN-I is administered at a dose of about 10 mg/kg.

10. The method of claim 9, wherein the antagonistic antibody that binds IFN-I is administered at a dose of about 10 mg/kg once every two weeks.

11. A method of determining whether a subject having a type I interferon (IFN-I) mediated disease is responsive to treatment with an IFN-I inhibitor and deciding whether to treat the subject, comprising:
   a) providing a biological sample from the subject;
   b) assaying gene expression of genes DHX58, EIF2AK2, HERC5, IFI44, IFI44L, IFI6, IRF7, PARP9, PLSCR1 and SAMD9L in the biological sample;
   c) determining a combined expression value of the genes DHX58, EIF2AK2, HERC5, IFI44, IFI44L, IFI6, IRF7, PARP9, PLSCR1 and SAMD9L in the biological sample;
   d) diagnosing the subject with the IFN-I mediated disease as responsive to treatment with the IFN-I inhibitor when the combined expression value is equal to or higher than a threshold value or diagnosing the subject with the IFN-I mediated disease as non-responsive to treatment with the IFN-I inhibitor when the combined expression value is less than a threshold value; and
   e) administering the IFN-I inhibitor to the subject diagnosed as responsive to treatment with the IFN-I inhibitor or refraining from administering the IFN-I inhibitor to the subject diagnosed as non-responsive to treatment with the IFN-I inhibitor, wherein the combined expression value is a sum of (i) normalized threshold cycle (CT) values (SUMΔCT) of genes DHX58, EIF2AK2, HERC5, IFI44, IFI44L, IFI6, IRF7, PARP9, PLSCR1 and SAMD9L and the threshold value is SUMΔCT of 57.474, or (ii) log 2 fold changes of normalized differential expression between the biological sample and a biological sample obtained from one or more healthy controls (SUMlog2($2^{-ddCT}$)) of genes DHX58, EIF2AK2, HERC5, IFI44, IFI44L, IFI6, IRF7, PARP9, PLSCR1 and SAMD9L and the threshold value is SUMlog2($2^{-ddCT}$) of 8.725.

12. The method of claim 11, wherein the combined expression value is a POISE Score of Formula I:
   POISE Score=70−|43.7251664−SUMlog2(2^-ddCT))| (Formula I) and the threshold value is the POISE Score of between 30 and 40.

13. The method of claim 12, wherein the threshold value is the POISE score of 35.

14. The method of claim 11, wherein the biological sample is a blood sample or a tissue sample.

15. The method of claim 11, wherein the IFN-I mediated disease is systemic lupus erythematosus (SLE), type I diabetes, psoriasis, primary Sjögren's disease, systemic sclerosis, rheumatoid arthritis, transplant rejection, dermatomyositis, polymyositis, Aicardi-Goutières syndrome, Sting associated vasculopathy with onset in infancy (SAVI) or chronic atypical neutrophilic dermatosis with lipodystrophy and elevated temperature syndrome (CANDLE).

16. The method of claim 15, wherein SLE comprises lupus nephritis, cutaneous lupus or lupus with central nervous system (CNS) manifestations.

17. The method of claim 11, wherein the IFN-I inhibitor is a molecule that blocks interaction of IFN-I with IFNAR, an antagonistic antibody that binds IFN-I, an antagonistic antibody that binds IFNAR, an inhibitor of Tyk2, Jak1, TLR7, TLR8, TLR9 or STING, a modulator or depletor of plasmacytoid dendritic cells; or an agent that degrades nucleic acids.

18. The method of claim 17, wherein the antagonistic antibody that binds IFN-I comprises:
   a) a heavy chain variable region 1 (HCDR1) of SEQ ID NO: 11, a HCDR2 of SEQ ID NO: 12, a HCDR3 of SEQ ID NO: 13, a light chain variable region 1 (LCDR1) of SEQ ID NO: 14, a LCDR2 comprising the amino acid sequence GAS and a LCDR3 of SEQ ID NO: 16;
   b) a heavy chain variable region (VH) of SEQ ID NO: 17 and a light chain variable region (VL) of SEQ ID NO: 18;
   c) a heavy chain (HC) of SEQ ID NO: 19 and a light chain (LC) of SEQ ID NO: 20, or
   d) any combination of a), b) and c).

19. The method of claim 18, wherein the antagonistic antibody that binds IFN-I is administered at a dose of about 10 mg/kg.

20. The method of claim 19, wherein the antagonistic antibody that binds IFN-I is administered at a dose of about 10 mg/kg once every two weeks.

* * * * *

SEQUENCE LISTING

<160> NUMBER OF SEQ ID NOS: 30

<210> SEQ ID NO 1
<211> LENGTH: 2631
<212> TYPE: DNA
<213> ORGANISM: Homo sapiens

<400> SEQUENCE: 1

```
agtttcagtt tccatttctg atttctgctc tctgcgctga gcacagcggc accaggctga        60
gctaagcagg gccgccttgg gcaggcctac gtggtggtgc aggcgagacc caggctgggc       120
aaggcgcagt tcagtttcc atcttgggtc tctgagctga gcagagtggc accaggctga        180
gttaagtggg actgccctgg gcagacctac ctactagagc agaatggagc ttcggtccta       240
ccaatgggag gtgatcatgc ctgccctgga gggcaagaat atcatcatct ggctgcccac       300
gggtgccggg aagacccggg cggctgctta tgtggccaag cggcacctag agactgtgga      360
tggagccaag gtggttgtat tggtcaacag ggtgcacctg gtgacccagc atggtgaaga      420
gttcaggcgc atgctggatg gacgctggac cgtgacaacc ctgagtgggg acatgggacc     480
acgtgctggc tttggccacc tggcccggtg ccatgacctg ctcatctgca cagcagagct       540
tctgcagatg gcactgacca gccccgagga ggaggagcac gtggagctca ctgtcttctc       600
cctgatcgtg gtggatgagt gccaccacac gcacaaggac accgtctaca acgtcatcat       660
gagccagtac ctagaactta aactccagag ggcacagccg ctaccccagg tgctgggtct       720
cacagcctcc ccaggcactg gcggggcctc caaactcgat ggggccatca accacgtcct       780
gcagctctgt gccaacttgg acacgtggtg catcatgtca ccccagaact gctgccccca       840
gctgcaggag cacagccaac agccttgcaa acagtacaac ctctgccaca ggcgcagcca      900
ggatccgttt ggggacttgc tgaagaagct catggaccaa atccatgacc acctggagat       960
gcctgagttg agccggaaat ttgggacgca aatgtatgag cagcaggtgg tgaagctgag     1020
tgaggctgcg gctttggctg ggcttcagga gcaacgggtg tatgcgcttc acctgaggcg    1080
ctacaatgac gcgctgctca tccatgacac cgtccgcgcc gtggatgcct tggctgcgct       1140
gcaggatttc tatcacaggg agcacgtcac taaaacccag atcctgtgtg ccgagcgccg      1200
gctgctggcc ctgttcgatg accgcaagaa tgagctggcc cacttggcaa ctcatggccc      1260
agagaatcca aaactggaga tgctggaaaa gatcctgcaa aggcagttca gtagctctaa     1320
```

```
cagccctcgg ggtatcatct tcacccgcac ccgccaaagc gcacactccc tcctgctctg   1380
gctccagcag cagcagggcc tgcagactgt ggacatccgg gcccagctac tgattggggc   1440
tgggaacagc agccagagca cccacatgac ccagagggac cagcaagaag tgatccagaa   1500
gttccaagat ggaaccctga accttctggt ggccacgagt gtggcggagg aggggctgga   1560
catcccacat tgcaatgtgg tggtgcgtta tgggctcttg accaatgaaa tctccatggt   1620
ccaggccagg ggccgtgccc gggccgatca gagtgtatac gcgtttgtag caactgaagg   1680
tagccgggag ctgaagcggg agctgatcaa cgaggcgctg gagacgctga tggagcaggc   1740
agtggctgct gtgcagaaaa tggaccaggc cgagtaccag gccaagatcc gggatctgca   1800
gcaggcagcc ttgaccaagc gggcggccca ggcagcccag cgggagaacc agcggcagca   1860
gttcccagtg gagcacgtgc agctactctg catcaactgc atggtggctg tgggccatgg   1920
cagcgacctg cggaaggtgg agggcaccca ccatgtcaat gtgaaccccca acttctcgaa   1980 ctactataat gtctccaggg atcctgtggt catcaacaaa gtcttcaagg actggaagcc   2040
tgggggtgtc atcagctgca ggaactgtgg ggaggtctgg ggtctgcaga tgatctacaa   2100
gtcagtgaag ctgccagtgc tcaaagtccg cagcatgctg ctggagaccc ctcaggggcg   2160
gatccaggcc aaaaagtggt cccgcgtgcc cttctccgtg cctgactttg acttcctgca   2220
gcattgtgcc gagaacttgt cggacctctc cctggactga ccacctcatt gctgcagtgc   2280
ccggtttggg ctgtaggggg cggagagtc tgcagcagac tccaggcccc tccttcctga   2340
atcatcagct gtgggcatca ggcccaccag ccacacagga gtcctgggca ccctggctta   2400
ggctcccgca atgggaaaac aaccggaggg ccagagctta gtccagacct accttgtacg   2460
cacatagaca tttcatatg cactggatgg agttagggaa actgaggcaa agaatttgc   2520 catactgtac tcagaatcac gacattcctt ccctaccaag gccacttcta ttttttgagg   2580
ctcctcataa aaataaatga aaaaatggga tagaaaaaaa aaaaaaaaa a              2631
```

<210> SEQ ID NO 2
<211> LENGTH: 4126
<212> TYPE: DNA
<213> ORGANISM: Homo sapiens

<400> SEQUENCE: 2

```
agcagacgag ggcttgtgcg agagggggcc gggcggctgc agggaaggcg gagtccaagg     60
ggaaaacgaa actgagaacc agctctcccg aagccgcggg tctccggccg gcggcggcgg    120
cggcggcggc ggcggcgcag tttctggagc aaattcagtt tgccttcctg gatttgtaaa    180
ttgtaatgac ctcaaaactt tagcagttct tccatctgac tcaggtttgc ttctctggcg    240
gtcttcagaa tcaacatcca cacttccgtg attatctgcg tgcattttgg acaaagcttc    300
caaccaggat acgggaagaa gaaatggctg gtgatctttc agcaggtttc ttcatggagg    360
aacttaatac ataccgtcag aagcaggag tagtacttaa atatcaagaa ctgcctaatt    420
caggacctcc acatgatagg aggtttacat ttcaagttat aatagatgga agagaatttc    480
cagaaggtga aggtagatca aagaaggaag caaaaaatgc cgcagccaaa ttagctgttg    540
agatacttaa taaggaaaag aaggcagtta gtcctttatt attgacaaca acgaattctt    600
cagaaggatt atccatgggg aattacatag gccttatcaa tagaattgcc cagaagaaaa    660
gactaactgt aaattatgaa cagtgtgcat cgggggtgca tgggccagaa ggatttcatt    720
ataaatgcaa aatgggacag aaagaatata gtattggtac aggttctact aaacaggaag    780
```

```
caaaacaatt ggccgctaaa cttgcatatc ttcagatatt atcagaagaa acctcagtga    840
aatctgacta cctgtcctct ggttcttttg ctactacgtg tgagtcccaa agcaactctt    900
tagtgaccag cacactcgct tctgaatcat catctgaagg tgacttctca gcagatacat    960
cagagataaa ttctaacagt gacagtttaa acagttcttc gttgcttatg aatggtctca   1020
gaaataatca aggaaggca aaaagatctt tggcacccag atttgacctt cctgacatga    1080
aagaaacaaa gtatactgtg acaagaggt tggcatgga ttttaaagaa atagaattaa     1140
ttggctcagg tggatttggc caagttttca aagcaaaaca cagaattgac ggaaagactt   1200
acgttattaa acgtgttaaa tataataacg agaaggcgga gcgtgaagta aaagcattgg   1260
caaaacttga tcatgtaaat attgttcact acaatggctg ttgggatgga tttgattatg   1320
atcctgagac cagtgatgat tctcttgaga gcagtgatta tgatcctgag aacagcaaaa   1380
atagttcaag gtcaaagact aagtgccttt tcatccaaat ggaattctgt gataaaggga   1440
ccttggaaca atggattgaa aaagaagag gcgagaaact agacaaagtt ttggctttgg    1500
aactctttga acaaataaca aaaggggtgg attatataca ttcaaaaaaa ttaattcata   1560
gagatcttaa gccaagtaat atattcttag tagatacaaa acaagtaaag attggagact   1620
ttggacttgt aacatctctg aaaaatgatg aaagcgaac aaggagtaag ggaactttgc     1680
gatacatgag cccagaacag atttcttcgc aagactatgg aaaggaagtg gacctctacg   1740
cttgggggct aattcttgct gaacttcttc atgtatgtga cactgctttt gaaacatcaa   1800
agttttcac agacctacgg gatggcatca tctcagatat atttgataaa aagaaaaaa     1860
ctcttctaca gaaatactct caaagaaacc tgaggatcga cctaacacat ctgaaatact   1920
aaggaccttg actgtgtgga agaaaagccc agagaaaaat gaacgacaca catgttagag   1980
cccttctgaa aaagtatcct gcttctgata tgcagttttc cttaaattat ctaaaatctg   2040
ctagggaata tcaatagata tttaccttt atttttaatgt ttcctttaat ttttactat   2100
ttttactaat ctttctgcag aaacagaaag gttttcttct ttttgcttca aaaacattct   2160
tacattttac tttttcctgg ctcatctctt tattctttt ttttttttaa agacagagtc    2220
tcgctctgtt gcccaggctg gagtgcaatg acacagtctt ggctcactgc aacttctgcc   2280
tcttgggttc aagtgattct cctgcctcag cctcctgagt agctggatta caggcatgtg   2340
ccacccaccc aactaatttt tgtgttttta ataaagacag ggtttcacca tgttggccag   2400
gctggtctca aactcctgac ctcaagtaat ccacctgcct cggcctccca agtgctggg    2460
attacaggga tgagccaccg cgcccagcct catctctttg ttctaaagat ggaaaaacca   2520
cccccaaatt ttctttttat actattaatg aatcaatcaa ttcatatcta tttattaaat   2580
ttctaccgct tttaggccaa aaaaatgtaa gatcgttctc tgcctcacat agcttacaag   2640
ccagctggag aaatatggta ctcattaaaa aaaaaaaaa aagtgatgta caaccacttc    2700
ggaaaacaat ttggcattat ctagtaaagt tgaatccatg tatacccaca tagctatcaa   2760
ttctattcct acatacgtgc ttacaagaat gtccataaaa ccctgtttat aatagccaaa   2820
agaacaggga acaaccataa tgcacatcaa aagaagaatg gattaaaaaa attatattca   2880
cacacaggag tactatatag tattgaaaac aattgaagta cagctaaatg taataacgta   2940
acacaataca actctcagaa acataatgtt aagcgaacaa agcaggtttt cagaaaatat   3000
atgcagaata attccattta tataaagttc cagagcatgc aaaactaaat cattttgtat   3060
aaaaaaccca acaaatgtga tgagacaata atggaagga agggaatgag aaatattaaa    3120
ttctggatgg tggttatctt tgagggaggg gaatgatgtg attggggaaa tggactttca   3180
```

| | | | | |
|---|---|---|---|---|
| aaggtaatgg | taacttcctt | aagctggatg | gtaggtccac | tagtgtttgc tgcatagtta | 3240 |
| tacctttat | cttaaataca | ttttgtatct | attgtaacaa | ccactttaaa gacaaccgtg | 3300 |
| ctgtaaggca | gtagctaaaa | acagaaaata | gtccatcggg | aagggtaaga tggctttctg | 3360 |
| ctgagcacag | ggctagaagt | gacagcccag | tgggccttcc | aactatatgc cagggtgtta | 3420 |
| gatgagtaga | gaggagacca | cccaggaagt | ctggacaagg | ggtctggcat gagctctgga | 3480 |
| gaagatatat | ttgaggaaca | tggggtatgc | tagtttgttg | tcctgaattg ctgtagagaa | 3540 |
| gataatttaa | attgcatctt | agaagacgac | cctgagggtg | aatttcaact tagggcaatt | 3600 |
| gttttagttt | gtttcttatt | ggtttaaatg | gatacttgaa | gctggataat ttataaggaa | 3660 |
| aagagattta | tatgacttac | agttctgcag | gctgtacaag | aaacatggca ccagcatctg | 3720 |
| cttcttcccc | ggctgcttcc | actcatggtg | gaaggtgaag | gggagccgga tgtgcagaga | 3780 |
| tcatatggca | agagaggaag | caagagagcg | agggagaagg | tgccaggctc ttttaaata | 3840 |
| accggctctt | gagggaacta | atagattgag | aactccttgc | ttctcctccc cagcacaccc | 3900 |
| cacccccagg | gacggcatta | atgtattcat | gaggggtctt | cccccatgac ccaaacacct | 3960 |
| cccatcaggc | cccacctcca | acactgggat | caaatttcaa | catgagattt tgggggacaa | 4020 |
| acatgcaaac | tatagcagca | accagctacc | attctaaaac | tgccatatga ttttaggatt | 4080 |
| tttaaaaagg | gccaaattta | ggttaagcaa | aaaaaaaaa | aaaaaa | 4126 |

<210> SEQ ID NO 3
<211> LENGTH: 3520
<212> TYPE: DNA
<213> ORGANISM: Homo sapiens

<400> SEQUENCE: 3

| | | | | |
|---|---|---|---|---|
| tcagtagctg | aggctgcggt | tccccgacgc | cacgcagctg | cgcgcagctg gttcccgctc | 60 |
| tgcagcgcaa | cgcctgaggc | agtgggcgcg | ctcagtcccg | ggaccaggcg ttctctcctc | 120 |
| tcgcctctgg | gcctgggacc | ccgcaaagcg | gcgatggagc | ggaggtcgcg gaggaagtcg | 180 |
| cggcgcaacg | ggcgctcgac | cgcgggcaag | gccgccgcga | cccagcccgc gaagtctccg | 240 |
| ggcgcacagc | tctggctctt | tcccagcgcc | gcgggcctcc | accgcgcgct gctccggagg | 300 |
| gtggaggtga | cgcgccaact | ctgctgctcg | ccggggcgcc | tcgcggtctt ggaacgcggc | 360 |
| ggggcgggcg | tccaggttca | ccagctgctc | gccgggagcg | gcggcgcccg gacgccgaaa | 420 |
| tgcattaaat | taggaaaaaa | catgaagata | cattccgtgg | accaaggagc agagcacatg | 480 |
| ctgattctct | catcagatgg | aaaaccattt | gagtatgaca | actatagcat gaaacatcta | 540 |
| aggtttgaaa | gcattttaca | agaaaaaaaa | ataattcaga | tcacatgtgg agattaccat | 600 |
| tctcttgcac | tctcaaaagg | tggtgagctt | tttgcctggg | gacagaacct gcatgggcag | 660 |
| cttggagttg | gaaggaaatt | tccctcaacc | accacaccac | agattgtgga gcacctcgca | 720 |
| ggagtaccct | tggctcagat | ttctgccgga | gaagcccaca | gcatggcctt atccatgtct | 780 |
| ggcaacattt | attcatgggg | aaaaaatgaa | tgtggacaac | taggcctggg ccacactgag | 840 |
| agtaaagatg | atccatccct | tattgaagga | ctagacaatc | agaaagttga atttgtcgct | 900 |
| tgtggtggct | ctcacagtgc | cctactcaca | caggatgggc | tgctgtttac tttcggtgct | 960 |
| ggaaaacatg | ggcaacttgg | tcataattca | acacagaatg | agctaagacc ctgtttggtg | 1020 |
| gctgagcttg | ttgggtatag | agtgactcag | atagcatgtg | gaaggtggca cacacttgcc | 1080 |
| tatgtttctg | atttggaaa | ggtcttttcc | tttggttctg | gaaagatgg acaactggga | 1140 |

| | |
|---|---|
| aatggtggaa cacgtgacca gctgatgccg cttccagtga agtatcatc aagtgaagaa | 1200 |
| ctcaaacttg aaagccatac ctcagaaaag gagttaataa tgattgctgg agggaatcaa | 1260 |
| agcattttgc tctggataaa gaaagagaat tcatatgtta atctgaagag acaattcct | 1320 |
| actctgaatg aagggactgt aaagagatgg attgctgatg tggagactaa acggtggcag | 1380 |
| agcacaaaaa gggaaatcca agagatattt tcatctcctg cttgtctaac tggaagtttt | 1440 |
| ttaaggaaaa aagaactac agaaatgatg cctgtttatt tggacttaaa taaagcaaga | 1500 |
| aacatcttca aggagttaac ccaaaaggac tggattacta acatgataac cacctgcctc | 1560 |
| aaagataatc tgctcaaaag acttccattt cattctccac cccaagaagc tttagaaatt | 1620 |
| ttcttccttc tcccagaatg tcctatgatg catatttcca acaactggga gagccttgtg | 1680 |
| gttccatttg caaggttgt ttgtaaaatg agtgaccagt cttcactggt tctggaagag | 1740 |
| tatgggcaa ctctgcaaga atccactttc agcaaactgg tccagatgtt taaaacagcc | 1800 |
| gtcatatgcc agttgatta ctgggatgaa agtgctgagg agaatggtaa tgttcaagct | 1860 |
| ctcctagaaa tgttgaagaa gctgcacagg gtaaaccagg tgaaatgtca actacctgaa | 1920 |
| agtattttcc aagtagacga actcttgcac cgtctcaatt tttttgtaga agtatgcaga | 1980 |
| aggtacttgt ggaaaatgac tgtggacgct tcagaaaatg tacaatgctg cgtcatattc | 2040 |
| agtcactttc catttatctt taataatctg tcgaaaatta aactactaca tacagacaca | 2100 |
| cttttaaaaa tagagagtaa aaaacataaa gcttatctta ggtcggcagc aattgaggaa | 2160 |
| gaaagagagt ctgaattcgc tttgaggccc acgtttgatc taacagtcag aaggaatcac | 2220 |
| ttgattgagg atgttttgaa tcagctaagt caatttgaga atgaagacct gaggaaagag | 2280 |
| ttatgggttt catttagtgg agaaattggg tatgacctcg gaggagtcaa gaaagagttc | 2340 |
| ttctactgtc tgtttgcaga gatgatccag ccggaatatg ggatgttcat gtatcctgaa | 2400 |
| ggggcttcct gcatgtggtt tcctgtcaag cctaaatttg agaagaaaag atacttcttt | 2460 |
| tttggggttc tatgtggact ttccctgttc aattgcaatg ttgccaacct tcctttccca | 2520 |
| ctggcactgt ttaagaaact tttggaccaa atgccatcat tggaagactt gaaagaactc | 2580 |
| agtcctgatt tgggaaagaa tttgcaaaca cttctggatg atgaaggtga taactttgag | 2640 |
| gaagtatttt acatccattt taatgtgcac tgggacagaa acgacacaaa cttaattcct | 2700 |
| aatggaagta gcataactgt caaccagact aacaagagag actatgtttc taagtatatc | 2760 |
| aattacattt tcaacgactc tgtaaaggcg gtttatgaag aatttcggag aggattttat | 2820 |
| aaaatgtgcg acgaagacat tatcaaatta ttccacccg aagaactgaa ggatgtgatt | 2880 |
| gttggaaata cagattatga ttggaaaaca tttgaaaaga atgcacgtta tgaaccagga | 2940 |
| tataacagtt cacatcccac catagtgatg ttttggaagg cttttccacaa attgactctg | 3000 |
| gaagaaaaga aaaaattcct tgtatttctt acaggaactg cagagactaca aatgaaagat | 3060 |
| ttaaataata tgaaaataac atttttgctgt cctgaaagtt ggaatgaaag agaccctata | 3120 |
| agagcactga catgtttcag tgtcctcttc ctccctaaat attctacaat ggaaacagtt | 3180 |
| gaagaagcgc ttcaagaagc catcaacaac aacagaggat tggctgacc agcttgcttg | 3240 |
| tccaacagcc ttattttgtt gttgttatcg ttgttgttgt tgttgttgtt gttgtttctc | 3300 |
| tactttgttt tgttttaggc ttttagcagc ctgaagccat ggttttttcat ttctgtctct | 3360 |
| agtgataagc aggaaagagg gatgaagaag agggtttact ggccggttag aacccgtgac | 3420 |
| tgtattctct cccttggata ccctatgcc tacatcatat tccttacctc ttttgggaaa | 3480 |
| tatttttcaa aaataaaata accgaaaaat taacataaaa | 3520 |

<210> SEQ ID NO 4
<211> LENGTH: 1742
<212> TYPE: DNA
<213> ORGANISM: Homo sapiens

<400> SEQUENCE: 4

| | | | | | |
|---|---|---|---|---|---|
| tctttgaagc | ttcaaggctg | ctgaataatt | tccttctccc | attttgtgcc | tgcctagcta | 60 |
| tccagacaga | gcagctaccc | tcagctctag | ctgatactac | agacagtaca | acagatcaag | 120 |
| aagtatggca | gtgacaactc | gtttgacatg | gttgcacgaa | agatcctgc | aaaatcattt | 180 |
| tggagggaag | cggcttagcc | ttctctataa | gggtagtgtc | catggattcc | gtaatggagt | 240 |
| tttgcttgac | agatgttgta | atcaagggcc | tactctaaca | gtgatttata | gtgaagatca | 300 |
| tattattgga | gcatatgcag | aagagagtta | ccaggaagga | aagtatgctt | ccatcatcct | 360 |
| ttttgcactt | caagatacta | aaatttcaga | atggaaacta | ggactatgta | caccagaaac | 420 |
| actgttttgt | tgtgatgtta | caaaatataa | ctccccaact | aatttccaga | tagatggaag | 480 |
| aaatagaaaa | gtgattatgg | acttaaagac | aatggaaaat | cttggacttg | ctcaaaattg | 540 |
| tactatctct | attcaggatt | atgaagtttt | tcgatgcgaa | gattcactgg | atgaaagaaa | 600 |
| gataaaaggg | gtcattgagc | tcaggaagag | cttactgtct | gccttgagaa | cttatgaacc | 660 |
| atatggatcc | ctggttcaac | aaatacgaat | tctgctgctg | gtccaattg | gagctgggaa | 720 |
| gtccagcttt | ttcaactcag | tgaggtctgt | tttccaaggg | catgtaacgc | atcaggcttt | 780 |
| ggtgggcact | aatacaactg | ggatatctga | gaagtatagg | acatactcta | ttagagacgg | 840 |
| gaaagatggc | aaatacctgc | cgtttattct | gtgtgactca | ctggggctga | gtgagaaaga | 900 |
| aggcggcctg | tgcagggatg | acatattcta | tatcttgaac | ggtaacattc | gtgatagata | 960 |
| ccagtttaat | cccatggaat | caatcaaatt | aaatcatcat | gactacattg | attccccatc | 1020 |
| gctgaaggac | agaattcatt | gtgtggcatt | tgtatttgat | gccagctcta | ttcaatactt | 1080 |
| ctcctctcag | atgatagtaa | agatcaaaag | aattcgaagg | gagttggtaa | acgctggtgt | 1140 |
| ggtacatgtg | gctttgctca | ctcatgtgga | tagcatggat | ttgattacaa | aaggtgacct | 1200 |
| tatagaaata | gagagatgtg | agcctgtgag | gtccaagcta | gaggaagtcc | aaagaaaact | 1260 |
| tggatttgct | ctttctgaca | tctcggtggt | tagcaattat | tcctctgagt | gggagctgga | 1320 |
| ccctgtaaag | gatgttctaa | ttctttctgc | tctgagacga | atgctatggg | ctgcagatga | 1380 |
| cttcttagag | gatttgcctt | ttgagcaaat | agggaatcta | agggaggaaa | ttatcaactg | 1440 |
| tgcacaagga | aaaaaataga | tatgtgaaag | gttcacgtaa | atttcctcac | atcacagaag | 1500 |
| attaaaattc | agaaggagaa | aaacacagac | caaagagaag | tatctaagac | caaagggatg | 1560 |
| tgttttatta | atgtctagga | tgaagaaatg | catagaacat | tgtagtactt | gtaaataact | 1620 |
| agaaataaca | tgatttagtc | ataattgtga | aaaataataa | taatttttct | tggatttatg | 1680 |
| ttctgtatct | gtgaaaaaat | aaatttctta | taaaactcgg | gtctaaaaaa | aaaaaaaaa | 1740 |
| aa | | | | | | 1742 |

<210> SEQ ID NO 5
<211> LENGTH: 5910
<212> TYPE: DNA
<213> ORGANISM: Homo sapiens

<400> SEQUENCE: 5

| | | | | | |
|---|---|---|---|---|---|
| aaagttagtg | gcagttggca | tgctgccagc | tgagtttttt | tgctgctttg | agtctcagtt | 60 |

```
ttctttctttt cctagagtct ctgaagccac agatctctta agaactttct gtctccaaac    120
cgtggctgct cgataaatca gacagaacag ttaatcctca atttaagcct gatctaaccc    180
ctagaaacag atatagaaca atggaagtga caacaagatt gacatggaat gatgaaaatc    240
atctgcgcaa gctgcttgga aatgtttctt tgagtcttct ctataagtct agtgttcatg    300
gaggtagcat tgaagatatg gttgaaagat gcagccgtca gggatgtact ataacaatgg    360
cttacattga ttacaatatg attgtagcct ttatgcttgg aaattatatt aatttacatg    420
aaagttctac agagccaaat gattccctat ggttttcact tcaaaagaaa aatgacacca    480
ctgaaataga aactttactc ttaaatacag caccaaaaat tattgatgag caactggtgt    540
gtcgtttatc gaaaacggat attttcatta tatgtcgaga taataaaatt tatctagata    600
aaatgataac aagaaacttg aaactaaggt tttatggcca ccgtcagtat ttggaatgtg    660 aagttttcg agttgaagga attaaggata acctagacga cataagagg ataattaaag    720 ccagagagca cagaaatagg cttctagcag acatcagaga ctataggccc tatgcagact    780
tggtttcaga aattcgtatt cttttggtgg gtccagttgg gtctggaaag tccagttttt    840
tcaattcagt caagtctatt tttcatggcc atgtgactgg ccaagccgta gtggggtctg    900
atatcaccag cataaccgag cggtatagga tatattctgt taaagatgga aaaaatggaa    960
aatctctgcc atttatgttg tgtgacacta tggggctaga tggggcagaa ggagcaggac    1020
tgtgcatgga tgacattccc cacatcttaa aaggttgtat gccagacaga tatcagttta    1080
attcccgtaa accaattaca cctgagcatt ctactttat cacctctcca tctctgaagg    1140
acaggattca ctgtgtggct tatgtcttag acatcaactc tattgacaat ctctactcta    1200
aaatgttggc aaaagtgaag caagttcaca agaagtatt aaactgtggt atagcatatg    1260
tggccttgct tactaaagtg gatgattgca gtgaggttct tcaagacaac ttttaaaca    1320 tgagtagatc tatgacttct caaagccggg tcatgaatgt ccataaaatg ctaggcattc    1380
ctatttccaa tattttgatg gttggaaatt atgcttcaga tttggaactg accccatga    1440 aggatattct catcctctct gcactgaggc agatgctgcg ggctgcagat gattttttag    1500
aagatttgcc tcttgaggaa actggtgcaa ttgagagagc gttacagccc tgcatttgag    1560
ataagttgcc ttgattctga catttggccc agcctgtact ggtgtgccgc aatgagagtc    1620
aatctctatt gacagcctgc ttcagatttt gcttttgttc gttttgcctt ctgtccttgg    1680
aacagtcata tctcaagttc aaaggccaaa acctgagaag cggtgggcta agataggtcc    1740
tactgcaaac caccctcca tatttccgta ccatttacaa ttcagtttct gtgacatctt    1800
tttaaaccac tggaggaaaa atgagatatt ctctaattta ttcttctata acactctata    1860
tagagctatg tgagtactaa tcacattgaa taatagttat aaaattattg tatagacatc    1920
tgcttcttaa acagattgtg agttctttga gaaacagcgt ggattttact tatctgtgta    1980
ttcacagagc ttagcacagt gcctggtaat gagcaagcat acttgccatt acttttcctt    2040
cccactctct ccaacatcac attcacttta aattttctg tatatagaaa ggaaaactag    2100
cctgggcaac atgatgaaac cccatctcca ctgcaaaaaa aaaaaaaaaa aataagaaag    2160
aacaaaacaa acccccacaaa aattagctgg gtatgatggc acgtgcctgt agtcccagtt    2220
actcaggatg attgattgag ccttggaggt ggaggctaca gtgagctgag attgtgccac    2280
tgtactctag ccagggagaa agagtgagat cctggctcaa aaaaccaaa taaaacaaaa    2340 caaacaaacg aaaacagaa aggaagactg aagagaatg aaaagctggg gagaggaaat    2400
aaaaataaag aaggaagagt gtttcattta tatctgaatg aaaatatgaa tgactctaag    2460
```

```
taattgaatt aattaaaatg agccaactttt tttttaacaa tttacatttt atttctatgg    2520
gaaaaaataa atattcctct tctaacaaac ccatgcttga ttttcattaa ttgaattcca    2580
aatcatccta gccatgtgtc cttccattta ggttactggg gcaaatcagt aagaaagttc    2640
ttatatttat gctccaaata attctgaagt cctcttacta gctgtgaaag ctagtactat    2700
taagaaagaa aacaaaattc ccaaaagata gctttcactt ttttttttcc ttaaagactt    2760
cctaattctc ttctccaaat tcttagtctt cttcaaaata atatgctttg gttcaatagt    2820
tatccacatt ctgacagtct aatttagttt taatcagaat tatactcatc ttttgggtag    2880
tcatagatat taagaaagca agagtttctt atgtccagtt atggaatatt tcctaaagca    2940
aggctgcagg tgaagttgtg ctcaagtgaa tgttcaggag acacaattca gtggaagaaa    3000
ttaagtcttt aaaaaagacc taggaatagg agaaccatgg aaattgagga ggtaggccta    3060
caagtagata ttgggaacaa aattagagag gcaaccagaa aaagttattt taggctcacc    3120
agagttgttc ttattgcaca gtaacacacc aatataccaa aacagcaggt attgcagtag    3180
agaaagagtt taataattga atggcagaaa aatgaggaag gttgaggaaa cctcaaatct    3240
acctccctgc tgagtctaag tttaggattt taagagaaa ggcaggtaag gtgctgaagg    3300
tctggagctg ctgatttgtt ggggtatagg gaatgaaatg aaacatacag agatgaaaac    3360
tggaagtttt ttttttgtttg ttttgttttt ttttttgttgt tgtttttttt tttttttgtt    3420
tttttgctga gtcaattcct tggagggggt cttcagactg actggtgtca gcagacccat    3480
gggattccaa gatctggaaa acttttaga tagaaacttg atgtttctta acgttacata    3540
tattatctta tagaaataac taagggaagt tagtgccttg tgaccacatc tatgtgactt    3600
ttaggcagta agaaactata aggaaaggag ctaacagtca tgctgtaagt agctacaggg    3660
aattggctta aagggcaagt tggttagtac ttagctgtgt ttttattcaa agtctacatt    3720
ttatgtagtg gttaatgttt gctgttcatt aggatggttt cacagttacc atacaaatgt    3780
agaagcaaca ggtccaaaaa gtagggcatg attttctcca tgtaatccag ggagaaaaca    3840
agccatgacc attgttggtt gggagactga aggtgattga aggttcacca tcatcctcac    3900
caacttttgg gccataattc acccaaccct ttggtggagc ctgaaaaaaa tctgggcaga    3960
atgtaggact tctttatttt gtttaaaggg gtaacacaga gtgcccttat gaaggagttg    4020
gagatcctgc aaggaagaga aggagtgaag gagagatcaa gagagagaaa caatgaggaa    4080
catttcattt gacccaacat cctttaggag cataaatgtt gacactaagt tatcccttttt    4140 gtgctaaaat ggacagtatt ggcaaaatga taccacaact tcttattctc tggctctata    4200
ttgctttgga aacacttaaa catcaaatgg agttaaatac atatttgaaa tttaggttag    4260
gaaatattgg tgaggaggcc tcaaaaaggg ggaaacatct tttgtctggg aggatatttt    4320
ccattttgtg gatttccctg atcttttttct accaccctga ggggtggtgg gaattatcat    4380
tttgctacat tttagaggtc atccaggatt tttgaaactt tacattctttt acggttaagc    4440 aagatgtaca gctcagtcaa agacactaaa ttcttcttag aaaaatagtg ctaaggagta    4500
tagcagatga cctatatgtg tgttggctgg gagaatatca tcttaaagtg agagtgatgt    4560
tgtggagaca gttgaaatgt caatgctaga gcctctgtgg tgtgaatggg cacgttaggt    4620
tgttgcatta gaaagtgact gtttctgaca gaaatttgta gctttgtgca aactcaccca    4680
ccatctacct caataaaata tagagaaaag aaaaatagag cagtttgagt tctatgaggt    4740
atgcaggccc agagagacat aagtatgttc ctttagtctt gcttcctgtg tgccacactg    4800
```

```
cccctccaca accatagctg ggggcaattg tttaaagtca ttttgttccc gactagctgc    4860
cttgcacatt atcttcattt tcctggaatt tgatacagag agcaatttat agccaattga    4920
tagcttatgc tgtttcaatg taaattcgtg gtaaataact taggaactgc ctcttctttt    4980
tctttgaaaa cctacttata actgttgcta ataagaatgt gtattgttca ggacaacttg    5040
tctccataca gttgggttgt aaccctcatg cttggcccaa ataaactctc tacttatatc    5100
agttttccct acacttcttc cttttaggtc aacaatacca agaggggtta ctgtgctggg    5160
taatgtgtaa acttgtgtct tgtttagaaa gataaattta aagactatca cattgctttt    5220
tcataaaaca agacaggtct acaattaatt tattttgacg caaattgata ggggggccaa    5280
gtaagcccca tatgcttaat gatcagctga tgaataatca tctcctagca acataactca    5340
atctaatgct aaggtaccca caagatggca aggctgatca aagtcgtcat ggaatcctgc    5400
aaccaaaagc catgggaatt tggaagccct caaatcccat tcctaatctg atgagtctat    5460
ggaccaattt gtggaggaca gtagattaaa tagatctgat ttttgccatc aatgtaagga    5520
ggataaaaac ttgcatacca attgtacacc cttgcaaaat ctttctctga tgttggagaa    5580
aatgggccag tgagatcatg gatatagaag tacagtcaat gttcagctgt accctcccac    5640
aatcccactt ccttcctcaa cacaattcaa acaaatagac tcagactgtt tcaggctcca    5700
ggacaggaag tgcagtgtag gcaaaattgc aaaaattgag ggcacagggg tggaggtggg    5760
ggggttgaat aacaagctgt gctaaataat tacgtgtaaa tatatttttt catttttaaa    5820
aattgatttc ttttgcacat tccatgacaa tatatgtcac attttttaaa taaatgcaaa    5880
gaagcataca tccaaaaaaa aaaaaaaaaa                                     5910

<210> SEQ ID NO 6
<211> LENGTH: 860
<212> TYPE: DNA
<213> ORGANISM: Homo sapiens

<400> SEQUENCE: 6
ccagccttca gccggagaac cgtttactcg ctgctgtgcc catctatcag caggctccgg      60
gctgaagatt gcttctcttc tctcctccaa ggtctagtga cggagcccgc gcgcggcgcc     120
accatgcggc agaaggcggt atcgcttttc ttgtgctacc tgctgctctt cacttgcagt     180
ggggtggagg caggtgagaa tgcgggtaag gatgcaggta agaaaaagtg ctcggagagc     240
tcggacagcg gctccgggtt ctggaaggcc ctgaccttca tggccgtcgg aggaggactc     300
gcagtcgccg gctgcccgc gctgggcttc accggcgccg gcatcgcggc caactcggtg     360
gctgcctcgc tgatgagctg gtctgcgatc ctgaatgggg gcggcgtgcc cgccgggggg     420
ctagtggcca cgctgcagag cctcgggggct ggtggcagca gcgtcgtcat aggtaatatt     480
ggtgccctga tgggctacgc cacccacaag tatctcgata gtgaggagga tgaggagtag     540
ccagcagctc ccagaacctc ttcttccttc ttggcctaac tcttccagtt aggatctaga     600
actttgcctt tttttttttt tttttttttt tgagatgggt tctcactata ttgtccaggc     660
tagagtgcag tggctattca cagatgcgaa catagtacac tgcagcctcc aactcctagc     720
ctcaagtgat cctcctgtct caacctccca agtaggatta caagcatgcg ccgacgatgc     780
ccagaatcca gaactttgtc tatcactctc cccaacaacc tagatgtgaa aacagaataa     840
acttcaccca gaaaacactt                                                 860

<210> SEQ ID NO 7
<211> LENGTH: 2012
```

<212> TYPE: DNA
<213> ORGANISM: Homo sapiens

<400> SEQUENCE: 7

```
gagacgaaac ttcccgtccc ggcggctctg cacccaggg tccggcctgc gccttcccgc      60
caggcctgga cactggttca acacctgtga cttcatgtgt gcgcgccggc cacacctgca    120
gtcacacctg tagcccctc tgccaagaga tccataccga ggcagcgtcg gtggctacaa    180
gccctcagtc cacacctgtg gacacctgtg cacctggcc acgacctg tggccgcggc      240
ctggcgtctg ctgcgacagg agcccttacc tccctgtta taacacctga ccgccaccta    300
actgccctg cagaaggagc aatggccttg gctcctgaga ggtaagagcc cggcccaccc    360
tctccagatg ccagtcccg agcgccctgc agccggccct gactctccgc ggccgggcac    420
ccgcagggca gccccacgcg tgctgttcgg agagtggctc cttggagaga tcagcagcgg    480
ctgctatgag gggctgcagt ggctggacga ggcccgcacc tgtttccgcg tgccctggaa    540
gcacttcgcg cgcaaggacc tgagcgagcg cgacgcgcgc atcttcaagg cctgggctgt    600
ggcccgcggc aggtggccgc ctagcagcag gggaggtggc ccgcccccg aggctgagac    660
tgcggagcgc gccggctgga aaccaacatt ccgctgcgca ctgcgcagca cgcgtcgctt    720
cgtgatgctg cgggataact cggggggaccc ggccgacccg cacaaggtgt acgcgctcag    780
ccgggagctg tgctggcgag aaggcccagg cacggaccag actgaggcag aggccccgc    840
agctgtccca ccaccacagg gtgggccccc agggccattc ctggcacaca cacatgctgg    900
actccaagcc ccaggcccc tccctgcccc agctggtgac aagggggacc tcctgctcca    960
ggcagtgcaa cagagctgcc tggcagacca tctgctgaca gcgtcatggg gggcagatcc   1020
agtcccaacc aaggctcctg gagagggaca agaagggctt cccctgactg gggcctgtgc   1080
tggaggccca gggctccctg ctggggagct gtacgggtgg gcagtagaga cgaccccag    1140
ccccgggccc cagcccgcgg cactaacgac aggcgaggcc gcggcccag agtccccgca   1200
ccaggcagag ccgtacctgt caccctcccc aagcgcctgc accgcggtgc aagagcccag   1260
cccaggggcg ctggacgtga ccatcatgta caagggccgc acggtgctgc agaaggtggt   1320
gggacacccg agctgcacgt tcctatacgg ccccccagac ccagctgtcc gggccacaga   1380
ccccagcag gtagcattcc ccagccctgc cgagctcccg gaccagaagc agctgcgcta   1440
cacgaggaa ctgctgcggc acgtggcccc tgggttgcac ctggagcttc gggggccaca    1500
gctgtgggcc cggcgcatgg gcaagtgcaa ggtgtactgg gaggtgggcg accccagg    1560
ctccgccagc ccctccaccc cagcctgcct gctgcctcgg aactgtgaca cccccatctt    1620
cgacttcaga gtcttcttcc aagagctggt ggaattccgg gcacggcagc gccgtggctc    1680
cccacgctat accatctacc tgggcttcgg gcaggacctg tcagctggga ggcccaagga    1740
gaagagcctg gtcctggtga agctggaacc ctggctgtgc cgagtgcacc tagagggcac    1800
gcagcgtgag ggtgtgtctt ccctggatag cagcagcctc agcctctgcc tgtccagcgc    1860
caacagcctc tatgacgaca tcgagtgctt ccttatggag ctggagcagc ccgcctagaa    1920
cccagtctaa tgagaactcc agaaagctgg agcagcccac ctagagctgg ccgcggccgc    1980
ccagtctaat aaaaagaact ccagaacacg ta                                   2012
```

<210> SEQ ID NO 8
<211> LENGTH: 3177
<212> TYPE: DNA
<213> ORGANISM: Homo sapiens -continued

```
<400> SEQUENCE: 8
agagccgctt ccccctcctc cctgtgctgt ctgcaccgag gagagcggcc tgccggaagt      60
gggccaccat atctggaaac tacagtctat gctttgaagc gcaaaaggga ataaacattt     120
aaagactccc ccggggacct ggaggatgga cttttccatg gtggccggag cagcagctta     180
caatgaaaaa tcaggtagga ttacctcgct ctcactcttg tttcagaaag tctttgctca     240
gatctttcct cagtggagaa agggaatac agaagaatgt ctcccctaca agtgctcaga      300
gactggtgct cttggagaaa actatagttg gcaaattccc attaaccaca atgacttcaa     360
aattttaaaa ataatgagc gtcagctgtg tgaagtcctc cagaataagt ttggctgtat      420
ctctaccctg gtctctccag ttcaggaagg caacagcaaa tctctgcaag tgttcagaaa     480
aatgctgact cctaggatag agttatcagt ctggaaagat gacctcacca cacatgctgt     540
tgatgctgtg gtgaatgcag ccaatgaaga tcttctgcat gggggaggcc tggccctggc     600
cctggtaaaa gctggtggat ttgaaatcca agaagagagc aaacagtttg ttgccagata     660
tggtaaagtg tcagctggtg agatagctgt cacgggagcg gggaggcttc cctgcaaaca     720
gatcatccat gctgttgggc ctcggtggat ggaatgggat aaacagggat gtactggaaa     780
gctgcagagg gccattgtaa gtattctgaa ttatgtcatc tataaaaata ctcacattaa     840
gacagtagca attccagcct tgagctctgg gattttcag ttccctctga atttgtgtac      900
aaagactatt gtagagacta tccggggtag tttgcaaggg aagccaatga tgagtaattt     960
gaaagaaatt cacctggtga gcaatgagga ccctactgtt gctgccttta agctgcttc    1020
agaattcatc ctaggaaga gtgagctggg acaagaaacc accccttctt tcaatgcaat    1080
ggtcgtgaac aacctgaccc tccagattgt ccagggccac attgaatggc agacggcaga    1140
tgtaattgtt aattctgtaa acccacatga tattacagtt ggacctgtgg caaagtcaat    1200
tctacaacaa gcaggagttg aaatgaaatc ggaatttctt gccacaaagg ctaaacagtt    1260
tcaacggtcc cagttggtac tggtcacaaa aggatttaac ttgttctgta atatatata    1320
ccatgtactg tggcattcag aatttcctaa acctcagata ttaaaacatg caatgaagga    1380
gtgtttggaa aaatgcattg agcaaaatat aacttccatt tcctttcctg cccttgggac    1440
tggaaacatg gaaataaaga aggaaacagc agcagagatt ttgtttgatg aagttttaac    1500
atttgccaaa gaccatgtaa aacaccagtt aactgtaaaa tttgtgatct ttccaacaga    1560
tttggagata tataaggctt tcagttctga atggcaaag aggtccaaga tgctgagttt    1620
gaacaattac agtgtccccc agtcaaccag agaggagaaa agagaaaatg ggcttgaagc    1680
tagatctcct gccatcaatc tgatgggatt caacgtggaa gagatgtatg aggcccacgc    1740
atggatccaa agaatcctga gtctccagaa ccaccacatc attgagaata atcatattct    1800
gtaccttggg agaaaggaac atgacatttt gtctcagctt cagaaaactt caagtgtctc    1860
catcacagaa attatcagcc caggaaggac agagttagag attgaaggag cccgggctga    1920
cctcattgag gtggttatga acattgaaga tatgctttgt aaagtacagg aggaaatggc    1980
aaggaaaaag gagcgaggcc tttggcgctc gttaggacag tggactattc agcaacaaaa    2040
aacccaagac gaaatgaaag aaaatatcat atttctgaaa tgtcctgtgc ctccaactca    2100
agagcttcta gatcaaaaga aacagtttga aaatgtggt ttgcaggttc taaaggtgga    2160
gaagatagac aatgaggtcc ttatggctgc cttcaaaga aagaagaaaa tgatggaaga    2220
aaaactgcac aggcaacctg tgagcccatag gctgtttcag caagtcccat accagttctg    2280
caatgtggta tgcagagttg gctttcaaag aatgtactcg acaccttgcg atccaaaata    2340
```

| | | |
|---|---|---|
| cggagctggc atatacttca ccaagaacct caaaaacctg gcagagaagg ccaagaaaat | 2400 |
| ctctgctgca gataagctga tctatgtgtt tgaggctgaa gtactcacag gcttcttctg | 2460 |
| ccagggacat ccgttaaata ttgttccccc accactgagt cctggagcta tagatggtca | 2520 |
| tgacagtgtg gttgacaatg tctccagccc tgaaacctt gttattttta gtggcatgca | 2580 |
| ggctataccct cagtatttgt ggacatgcac ccaggaatat gtacagtcac aagattactc | 2640 |
| atcaggacca atgagaccct ttgcacagca tccttggagg ggattcgcaa gtggcagccc | 2700 |
| tgttgattaa tctctacatc attttaacag ctggtatggc cttaccttgg gtgaactaac | 2760 |
| caaataatga ccatcgatgg ctcaaagagt ggcttgaata tatcccatgg gttatctgta | 2820 |
| tggactgact gggttattga aggactagc cacatactag catcttagtg cctttatctg | 2880 |
| tctttatgtc ttggggttgg ggtaggtaga taccaaatga aacactttca ggaccttcct | 2940 |
| tcctcttgca gttgttcttt aatctccttt actagaggag ataaatattt tgcatataat | 3000 |
| gaagaaattt ttctagtata taacgcaggc ctttttattt ctaaaatgat gatagtataa | 3060 |
| aaatgttagg ataacagaat gattttagat tttccagaga atattataaa gtgctttagg | 3120 |
| tatgaaaata aatcatcttt gtctgattaa ctggctctga aaaaaaaaaa aaaaaaa | 3177 |

```
<210> SEQ ID NO 9
<211> LENGTH: 2228
<212> TYPE: DNA
<213> ORGANISM: Homo sapiens

<400> SEQUENCE: 9
```

| | | |
|---|---|---|
| caccggacaa acgtctctgg agtctctcca atgagcaaga aagcaagtcg ggggtagggg | 60 |
| agggggcctca caccaggggg tgggcgcagt ccctcctcca gctccttcac cctccagtag | 120 |
| tctcgtgggt ccccgagcgc cagcgcggga accgggaaaa ggaaaccgtg ttgtgtacgt | 180 |
| aagattcagg aaacgaaacc aggagccgcg ggtgttggcg caaaggttac tcccagaccc | 240 |
| ttttccggct gacttctgag aaggttgcgc agcagctgtg cccggcagtc tagaggcgca | 300 |
| gaagaggaag ccatcgcctg gccccggctc tctggacctt gtctcgctcg ggagcggaaa | 360 |
| cagcggcagc cagagaactg ttttaatcat ggacaaacaa aactcacaga tgaatgcttc | 420 |
| tcacccggaa acaaacttgc cagttgggta tcctcctcag tatccaccga cagcattcca | 480 |
| aggacctcca ggatatagtg gctaccctgg gccccaggtc agctacccac cccaccagc | 540 |
| cggccattca ggtcctggcc cagctggctt tcctgtccca aatcagccag tgtataatca | 600 |
| gccagtatat aatcagccag ttggagctgc aggggtacca tggatgccag cgccacagcc | 660 |
| tccattaaac tgtccaccctg gattagaata tttaagtcag atagatcaga tactgattca | 720 |
| tcagcaaatt gaacttctgg aagttttaac aggttttgaa actaataaca aatatgaaat | 780 |
| taagaacagc tttggacaga gggtttactt tgcagcggaa gatactgatt gctgtacccg | 840 |
| aaattgctgt gggccatcta gacctttac cttgaggatt attgataata tgggtcaaga | 900 |
| agtcataact ctggagagac cactaagatg tagcagctgt tgttgtccct gctgccttca | 960 |
| ggagatagaa atccaagctc ctcctggtgt accaataggt tatgttattc agacttggca | 1020 |
| cccatgtcta ccaaagttta caattcaaaa tgagaaaaga gaggatgtac taaaaataag | 1080 |
| tggtccatgt gttgtgtgca gctgttgtgg agatgttgat tttgagatta aatctcttga | 1140 |
| tgaacagtgt gtggttggca aaattttccaa gcactggact ggaattttga gagaggcatt | 1200 |
| tacagacgct gataactttg gaatccagtt ccctttagac cttgatgtta aaatgaaagc | 1260 |

| | |
|---|---|
| tgtaatgatt ggtgcctgtt tcctcattga cttcatgttt tttgaaagca ctggcagcca | 1320 |
| ggaacaaaaa tcaggagtgt ggtagtggat tagtgaaagt ctcctcagga aatctgaagt | 1380 |
| ctgtatattg attgagacta tctaaactca tacctgtatg aattaagctg taaggcctgt | 1440 |
| agctctggtt gtatactttt gcttttcaaa ttatagttta tcttctgtat aactgattta | 1500 |
| taaaggtttt tgtacatttt ttaatactca ttgtcaattt gagaaaaagg acatatgagt | 1560 |
| ttttgcattt attaatgaaa cttcctttga aaaactgctt tgaattatga tctctgattc | 1620 |
| attgtccatt ttactaccaa atattaacta aggccttatt aattttata taaattatat | 1680 |
| cttgtcctat taaatctagt tacaatttat ttcatgcata agagctaatg ttattttgca | 1740 |
| aatgccatat attcaaaaaa gctcaaagat aattttcttt actattatgt tcaaataata | 1800 |
| ttcaatatgc atattatctt taaaaagtta atgttttttt taatcttcaa gaaatcatgc | 1860 |
| tacacttaac ttctcctaga agctaatcta taccataata ttttcatatt cacaagatat | 1920 |
| taaattacca attttcaaat tattgttagt aaagaacaaa atgattctct cccaaagaaa | 1980 |
| gacacatttt aaatactcct tcactctaaa actctgtat tataactttt gaaagttaat | 2040 |
| atttctacat gaaatgttta gctcttacac tctatccttc ctagaaaatg gtaattgaga | 2100 |
| ttactcagat attaattaaa tacaaatca tatatatatt cacagagtat aaacctaaat | 2160 |
| aatgatctat tagattcaaa tatttgaaat aaaaacttga tttttttgta aaaaaaaaa | 2220 |
| aaaaaaaa | 2228 |

<210> SEQ ID NO 10
<211> LENGTH: 7166
<212> TYPE: DNA
<213> ORGANISM: Homo sapiens

<400> SEQUENCE: 10

| | |
|---|---|
| gcttctcaac tggcactctg acacaccctc agaaagtcag agtactggga gaacagaaga | 60 |
| cttcacaatt taatgcctca gttttttaaaa aaggatcctt acacttcatg tctcctagcc | 120 |
| atcagaagag gaatgagaca gcaaaagttc aaatggcctg tttcaagttt ctgatataaa | 180 |
| acgatgacat tttcaggaaa atcctgcatt tccagagaga gactggctgg ttaaatttct | 240 |
| gaaagaggac accagctaaa agaaggtatt gcatctcacc cgagcagact gtgtctgtgg | 300 |
| aaagtgtaag ccccttgcca gaagagcagc ttcccagcaa aggcagaggg tgaaaacagc | 360 |
| aaaggtctta agacactggg gacctagagt caaaagggac ctcctccagg gaaaacgctg | 420 |
| tgtgagaaat ggcctcattc ggtgactgtg agtgacacag cagaaagttg ggtcattccg | 480 |
| gctgcttttt tgagaagtcc ctgaagagat caataacagc aagagggaac ctggcaagga | 540 |
| agctattcct ataatccagg aaagagatga ggaaggcttg gaccaggtgg tagtggtgtc | 600 |
| aggtagtcaa atgctgggta tattttgaag atacacccca taggatttgc tccacattga | 660 |
| atgtggaatg ctggaagaga gataaagtgt acctgtcaca tactttttga gttttatta | 720 |
| ttttcttaga agtaagtaca caaagagatg ctacctagga gaagggtatt ctttcacta | 780 |
| ttctttcaaa ttttctgtat gttcaaacat tttcatagta gaaagttggg gggaaaatct | 840 |
| gtttcataaa catttcctca gcagcagtcc agtctattgc attttaattg ttgtgtatat | 900 |
| cattgtttta tgcaatacgt tctcaacaag tatatcctcc ggcaaactga acaaggacca | 960 |
| agtctgttct gcctacagct ctgcttcctc atagctgctt tccagaacgt gactcttgca | 1020 |
| aattatcaag aaaggggaac taatctaagg gatccagatc aaacagcctc atgaagactt | 1080 |
| attttatgtt tctaatataa agatagaagt tttcagaaaa gccctgctac acagaggatc | 1140 |

```
agagcagggg tgggcctgct gggctgcagc tgggattctg agcatccttt cccggaggca   1200
cggaaagtga gtgagtgagc ccagtgagga agaagttgaa gctttgatat gagtaaacaa   1260
gtatctctac ctgaaatgat taaagactgg accaaagagc atgtgaaaaa atgggtaaat   1320
gaagacctta agattaatga gcaatacggg caaattctgc tcagtgaaga agtaacagga   1380
ttagtcctgc aggaattaac tgagaaggac cttgtagaaa tggggctacc atggggtcca   1440
gcacttttga taaaacgttc atacaacaaa ttgaatagta agtcccctga aagtgacaat   1500
catgatccgg gacaattaga taattcaaaa ccgtccaaaa cagaacacca gaaaaatcca   1560
aaacacacca aaaaggaaga agaaaattca atgtcatcta atattgatta tgatcccaga   1620
gagatcagag atatcaaaca agaagaatca attcttatga aagaaaatgt gttagatgaa   1680
gtagcaaatg ctaaacacaa gaaaaagggt aagctaaaac ctgaacaatt gacttgtatg   1740
ccatatcctt ttgatcagtt ccatgacagc catcgctaca tagaacatta tactctacaa   1800
cctgaaacag gagcactcaa tctcattgat ccaatacatg agttcaaagc tctcacaaac   1860
acagaaacag ccacggaagt ggacattaag atgaaattca gcaatgaagt cttccgattt   1920
gcatcagctt gtatgaattc acgcaccaat ggcaccatcc attttggagt caaggacaaa   1980
ccccatggag aaaattgttg gtgtgaaaatc accagtaagg ctgccttcat tgaccacttc   2040
aatgtaatga tcaaaaagta ttttgaagaa agtgagatca tgaagccaa gaagtgtatt   2100
cgggagccaa ggtttgtgga agtccttctg cagaacaata caccatctga cagatttgtc   2160
attgaagttg atactattcc aaaacactct atatgtaatg ataagtattt ctacattcag   2220
atgcaaattt gtaaagataa aatatggaaa caaaaccaaa atctttcact gtttgtaaga   2280
gaaggggcta gctctaggga tatcctggcc aattccaagc aacgggatgt agatttcaag   2340
gcattttttac aaaatttaaa gtcactggta gcatctagaa aagaggctga agaagagtat   2400
ggaatgaagg caatgaagaa ggagagtgaa ggactaaagc tggttaaaact tctcatagga   2460
aaccgagact cactggataa ttcatactat gactggtaca ttcttgtaac aaataaatgc   2520
catccaaacc aaataaagca cttagatttt taaaagaaa ttaaatggtt tgctgtgttg   2580
gagtttgatc ctgaatctat gatcaatgga gtggtcaaag cttacaaaga aagtcgggtg   2640
gcaaaccttc actttccaaa tcaatatgaa gacaagacaa ctaacatgtg ggagaagatt   2700
tctactctta atctttacca acagcccagc tggattttct gcaacggcag atcagacctg   2760
aaaagcgaga catataaacc tctagaacca catttatggc agagagaaag agcttcagaa   2820
gtcaggaaac taatttttatt tctcacagat gaaaatataa tgacaagagg aaaattttttg   2880
gtagtgtttc tattactctc ttcagtggaa agcccaggag atccactcat tgaaactttc   2940
tgggcttttct atcaagctct caaggaatg gaaaatatgt tgtgtatctc tgtaaactca   3000
catatttatc aacgatggaa agatctacta caaacaagaa tgaagatgga agatgaacta   3060
acaaaccaca gtatttccac tttaaatata gaactggtaa acagcactat ccttaaacta   3120
aaatcggtga ctcggtcatc aagaaggttt ttgcccgccc gtggatcttc ttcagttatc   3180
ctagagaaaa agaaagagga tgtcttgact gcactggaaa tcctctgtga aaatgagtgt   3240
acagagacag acatcgagaa agacaaatct aaattcctgg agtttaagaa atcaaaagaa   3300
gaacactttt atcgaggtgg caaagtatcc tggtggaact tctatttttc ttctgaaaac   3360
tattcttcag attttgttaa agggacagt tatgaaaagc ttaaagattt aatacactgc   3420
tgggcagagt ctcctaaacc aatatttgca aaaatcatca atctttatca tcatccaggc   3480
```

```
tgtggaggta ccacactggc tatgcatgtt ctctgggact taaagaaaaa cttcagatgt   3540
gctgtgttaa aaaacaagac aactgatttt gcagaaattg cagagcaagt gatcaatctg   3600
gtcacctata gggcaaagag ccatcaggat tacattcctg tgcttctcct tgtggatgat   3660
tttgaagaac aagaaaatgt ctactttcta caaaatgcca tccattccgt tttagcagaa   3720
aaggatttgc gatatgaaaa acattggta attatcttaa actgcatgag atcccggaat   3780
ccagatgaaa gtgcaaaatt ggcagacagt attgcactaa attaccaact tcttccaag    3840 gaacaaagag cttttggtgc caaactgaag gaaattgaaa agcagcacaa gaactgtgaa   3900 aactttatt ccttcatgat catgaaaagc aattttgatg aaacatatat agaaaatgta    3960
gtcaggaata tcctaaaagg acaggatgtt gacagcaagg aagcacaact catttccttc   4020
ctggctttac tcagctctta tgttactgac tctacaattt cagtttcaca gtgtgaaata   4080
tttttgggaa tcatatacac tagtacaccc tgggaacctg aaagcttaga agacaagatg   4140
ggaacttatt ctacacttct aataaaaaca gaagttgcag aatatgggag atacacaggt   4200
gtgcgtatca ttcaccctct gattgccctg tactgtctaa agaactgga agaagctat    4260 cacttggata aatgtcaaat tgcattgaat atattagaag agaatttatt ctatgattct   4320
ggaataggaa gagacaaatt tcaacatgat gttcaaactc ttctgcttac aagacagcgc   4380
aaggtgtatg gagatgaaac agacactctg ttttcccccat taatggaagc tttacagaat  4440
aaagacattg aaaaggtctt gagtgcagga agtagacgat tcccacaaaa tgcattcatt   4500
tgtcaagcct tagcaagaca tttctacatt aaagagaagg actttaacac agctctggac   4560
tgggcacgtc aggccaaaat gaaagcacct aaaaattcct atatttcaga tacactaggt   4620
caagtctaca aaagtgaaat caaatggtgg ttggatggga acaaaaactg taggagcatt   4680
actgttaatg acctaacaca tctcctagaa gctgcggaaa aagcctcaag agcttttcaaa  4740 gaatcccaaa ggcaaactga tagtaaaaac tatgaaaccg agaactggtc accacagaag   4800
tcccagagac gatatgacat gtataacaca gcttgtttct tgggtgaaat agaagttggt   4860
ctttacacta tccagattct tcagctcact ccctttttcc acaaagaaaa tgaattatcc   4920
aaaaaacata tggtgcaatt tttatcagga aagtggacca ttcctcctga tcccagaaat   4980
gaatgttatt tggctcttag caagttcaca tcccacctaa aaaatttaca atcagatctg   5040
aaaaggtgct ttgactttt tattgattat atggttcttc tgaaaatgag gtataccccaa  5100 aaagaaattg cagaaatcat gttaagcaag aaagtcagtc gttgtttcag gaaatacaca   5160
gaacttttct gtcatttgga tccatgtcta ttacaaagta agagagtca attactccag   5220 gaggagaatt gcaggaaaaa gctagaagct ctgagagcag ataggtttgc tggactcttg   5280
gaatatctta atccaaacta caaagatgct accaccatgg aaagtatagt gaatgaatat   5340
gccttcctac tgcagcaaaa ctcaaaaaag cccatgacaa atgagaaaca aaattccatt   5400
ttggccaaca ttattctgag ttgtctaaag cccaactcca agttaattca accacttacc   5460
acgctaaaaa aacaactccg agaggtcttg caatttgtag gactaagtca tcaatatcca   5520 ggtcccttatt tcttggcctg cctcctgttc tggccagaaa atcaagagct agatcaagat   5580
tccaaactaa tagaaaagta tgtttcatcc ttaaatagat ccttcagggg acagtacaag   5640
cgcatgtgca ggtccaagca ggcaagcaca cttttctatc tgggcaaaag gaagggtcta   5700
aacagtattg ttcacaaggc caaaatagag cagtactttg ataaagcaca aaatacaaat   5760
tccctctggc acagtgggga tgtgtggaaa aaaaatgaag tcaaagacct cctgcgtcgt   5820
ctaactggtc aggctgaagg caagctaatc tctgtagaat atggaacaga ggaaaaaata   5880
```

-continued

```
aaaataccag taatatctgt ttattcaggt ccactcagaa gtggtaggaa catagaaaga    5940
gtgtctttct acctaggatt ttccattgaa ggccctctgg catatgatat agaagtaatt    6000
taagacaata catcacctgt agttcaaata cgtttattta tatctttatg attttattct    6060
ctctctctat tctcatggca cttttcataac attatggcta acctctaatt acagattttg    6120
cttttgcctc cctgaatgaa ttacaagcct ttttaagata tgaaatatgc ctacccgcag    6180
agcttggcac aaagtggagt caatctttta atgttttaaa tatgcatttt cagactcaaa    6240
taattaagaa gtttcattga tatccactgg tcacatcata actgtctata gggcaataaa    6300
atctgtgtta aactcaattg cttttataag ttttctaaat tatttcttca ctgtgacagc    6360
aaagatttaa ataagatgaa tgtaaaagag aaagcttatt ggactcaaac ccacagatcc    6420
acaccagagt tctatttacc tcatcttggt atcaataaaa acttatgtgg aaggtaaata    6480
tattgttccc catccaccac ataacactct ccccaacaca cacacacaca cacacacaca    6540
cacacacaca cacacacact ccttgtaccc cttgcccttc tcccagctca ttgctccagg    6600
agagagaaga gttcaaaaaa taaagtaatc ataaacttga actctctcca ttctcttgtt    6660
cccatttaca ggtgaatctc ttcctttaag ccatttttgt ctcctgtgaa tacagcctta    6720
tctccacctg tttcttagat cccatctccc ctggcttatt ttttccattc attaccctct    6780
ttgttccctt tacttctcaa cctgtgctat atacatgctg ttctctctgt tgagattgcc    6840
ttatttccat ctaacattct ctctcctgct attctgattt gtcattcaca actgatttca    6900
agagtcacct tcaccaggaa gtcttccttg accaccatca ttcctgcctg attagagggc    6960
ttcctcatgg taatatgtgt tctcaagttt tcagtgtcaa ggaatgccat cccagaagct    7020
cattctcaga tgcacaacag ccagaacagt ctcaagcagc attctagagc ttggaattta    7080
agaactacgc attgcctata aagtgaaaca taggctaata tagattaaat tgaatattga    7140
ataaaaaata tatttattta tccaca                                         7166
```

```
<210> SEQ ID NO 11
<211> LENGTH: 8
<212> TYPE: PRT
<213> ORGANISM: Artificial Sequence
<220> FEATURE:
<223> OTHER INFORMATION: HCDR1 of an antibody that binds IFN-I

<400> SEQUENCE: 11

Gly Tyr Ser Phe Thr Ser Tyr Trp
1               5

<210> SEQ ID NO 12
<211> LENGTH: 8
<212> TYPE: PRT
<213> ORGANISM: Artificial Sequence
<220> FEATURE:
<223> OTHER INFORMATION: HCDR2 of an antibody that binds IFN-I

<400> SEQUENCE: 12

Ile Asp Pro Ser Asp Ser Asp Thr
1               5

<210> SEQ ID NO 13
<211> LENGTH: 14
<212> TYPE: PRT
<213> ORGANISM: Artificial Sequence
<220> FEATURE:
<223> OTHER INFORMATION: HCDR3 of an antibody that binds IFN-I
```

<400> SEQUENCE: 13

Ala Arg His Pro Gly Leu Asn Trp Ala Pro Asp Phe Asp Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: LCDR1 of an antibody that binds IFN-I

<400> SEQUENCE: 14

Gln Ser Ile Asp Asn Ser Tyr
1               5

<210> SEQ ID NO 15
<211> LENGTH: 172
<212> TYPE: PRT
<213> ORGANISM: Homo sapiens

<400> SEQUENCE: 15

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Lys Gly Ser Gln Leu
            35                  40                  45

Gln Lys Ala His Val Met Ser Val Leu His Glu Met Leu Gln Gln Ile
        50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170

<210> SEQ ID NO 16
<211> LENGTH: 9
<212> TYPE: PRT
<213> ORGANISM: Artificial Sequence
<220> FEATURE:
<223> OTHER INFORMATION: LCDR3 of an antibody that binds IFN-I

<400> SEQUENCE: 16

Gln Gln Gly Tyr Asp Phe Pro Leu Thr
1               5

<210> SEQ ID NO 17
<211> LENGTH: 121
<212> TYPE: PRT
<213> ORGANISM: Artificial Sequence
<220> FEATURE:
<223> OTHER INFORMATION: VH of an antibody that binds IFN-I

```
<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Gly Leu Asn Trp Ala Pro Asp Phe Asp Tyr Trp Gly
            100                 105                 110

Gln Gly Thr Leu Val Thr Val Ser Ser
            115                 120

<210> SEQ ID NO 18
<211> LENGTH: 108
<212> TYPE: PRT
<213> ORGANISM: Artificial Sequence
<220> FEATURE:
<223> OTHER INFORMATION: VL of an antibody that binds IFN-I

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
                85                  90                  95

Leu Thr Phe Gly Gln Gly Thr Lys Val Glu Ile Lys
            100                 105

<210> SEQ ID NO 19
<211> LENGTH: 451
<212> TYPE: PRT
<213> ORGANISM: Artificial Sequence
<220> FEATURE:
<223> OTHER INFORMATION: HC of an antibody that binds IFN-I

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Pro Gly Leu Asn Trp Ala Pro Asp Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450

<210> SEQ ID NO 20
<211> LENGTH: 215

```
<212> TYPE: PRT
<213> ORGANISM: Artificial Sequence
<220> FEATURE:
<223> OTHER INFORMATION: LC of an antibody that binds IFN-I

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 5
<212> TYPE: PRT
<213> ORGANISM: Homo sapiens

<400> SEQUENCE: 21

Asn Tyr Trp Ile Ala
1               5

<210> SEQ ID NO 22
<211> LENGTH: 17
<212> TYPE: PRT
<213> ORGANISM: Homo sapiens

<400> SEQUENCE: 22

Ile Ile Tyr Pro Gly Asp Ser Asp Ile Arg Tyr Ser Pro Ser Phe Gln
1               5                   10                  15

Gly

<210> SEQ ID NO 23
<211> LENGTH: 8
<212> TYPE: PRT
<213> ORGANISM: Homo sapiens
```

```
<400> SEQUENCE: 23

His Asp Ile Glu Gly Phe Asp Tyr
1               5

<210> SEQ ID NO 24
<211> LENGTH: 12
<212> TYPE: PRT
<213> ORGANISM: Homo sapiens

<400> SEQUENCE: 24

Arg Ala Ser Gln Ser Val Ser Ser Ser Phe Phe Ala
1               5                   10

<210> SEQ ID NO 25
<211> LENGTH: 7
<212> TYPE: PRT
<213> ORGANISM: Homo sapiens

<400> SEQUENCE: 25

Gly Ala Ser Ser Arg Ala Thr
1               5

<210> SEQ ID NO 26
<211> LENGTH: 9
<212> TYPE: PRT
<213> ORGANISM: Homo sapiens

<400> SEQUENCE: 26

Gln Gln Tyr Asp Ser Ser Ala Ile Thr
1               5

<210> SEQ ID NO 27
<211> LENGTH: 117
<212> TYPE: PRT
<213> ORGANISM: Homo sapiens

<400> SEQUENCE: 27

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Gly Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
        115

<210> SEQ ID NO 28
<211> LENGTH: 108
<212> TYPE: PRT
<213> ORGANISM: Homo sapiens

<400> SEQUENCE: 28

Glu Ile Val Leu Thr Gln Ser Pro Gly Thr Leu Ser Leu Ser Pro Gly
```

```
1               5                   10                  15
Glu Arg Ala Thr Leu Ser Cys Arg Ala Ser Gln Ser Val Ser Ser Ser
                20                  25                  30

Phe Phe Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Leu Ser
        50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys
                100                 105
```

<210> SEQ ID NO 29
<211> LENGTH: 447
<212> TYPE: PRT
<213> ORGANISM: Homo sapiens

<400> SEQUENCE: 29

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
                20                  25                  30

Trp Ile Ala Trp Val Arg Gln Met Pro Gly Lys Gly Leu Glu Ser Met
                35                  40                  45

Gly Ile Ile Tyr Pro Gly Asp Ser Asp Ile Arg Tyr Ser Pro Ser Phe
        50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 30
<211> LENGTH: 215
<212> TYPE: PRT
<213> ORGANISM: Homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215
```